(12) United States Patent  
Kobayashi et al.

(10) Patent No.: US 9,011,404 B2
(45) Date of Patent: Apr. 21, 2015

(54) PULL-ON ABSORBENT ARTICLE AND METHOD OF MAKING THE SAME

(75) Inventors: Kenji Kobayashi, Tochigi (JP); Ryoichi Yamamoto, Tochigi (JP); Kenji Ando, Tochigi (JP); Takuo Yanashima, Tochigi (JP); Akio Morita, Tochigi (JP)

(73) Assignee: Kao Corporation, Tokyo (JP)

( * ) Notice: Subject to any disclaimer, the term of this patent is extended or adjusted under 35 U.S.C. 154(b) by 636 days.

(21) Appl. No.: 13/377,765

(22) PCT Filed: Jun. 28, 2010

(86) PCT No.: PCT/JP2010/060991
§ 371 (c)(1),
(2), (4) Date: Dec. 12, 2011

(87) PCT Pub. No.: WO2011/001944
PCT Pub. Date: Jan. 6, 2011

(65) Prior Publication Data
US 2012/0095429 A1 Apr. 19, 2012

(30) Foreign Application Priority Data

| | | |
|---|---|---|
| Jul. 1, 2009 | (JP) | 2009-157272 |
| Jul. 1, 2009 | (JP) | 2009-157273 |
| Aug. 17, 2009 | (JP) | 2009-188340 |
| Apr. 15, 2010 | (JP) | 2010-094365 |
| Apr. 15, 2010 | (JP) | 2010-094366 |

(51) Int. Cl.
*A61F 13/15* (2006.01)
*B32B 37/00* (2006.01)
(Continued)

(52) U.S. Cl.
CPC ..... *A61F 13/15804* (2013.01); *A61F 13/49011* (2013.01); *A61F 13/4902* (2013.01); *A61F 13/496* (2013.01); *D04H 3/04* (2013.01)

(58) Field of Classification Search
USPC ............. 604/385.22, 385.23, 385.24, 385.29, 604/385.3, 385.27, 385.26
See application file for complete search history.

(56) References Cited

U.S. PATENT DOCUMENTS

| | | |
|---|---|---|
| 2004/0010241 A1 | 1/2004 | Sanders et al. |
| 2005/0107763 A1 | 5/2005 | Matsuda et al. |

(Continued)

FOREIGN PATENT DOCUMENTS

| | | |
|---|---|---|
| JP | 62-199808 A | 9/1987 |
| JP | 8-038546 A | 2/1996 |

(Continued)

OTHER PUBLICATIONS

International Search Report, dated Apr. 3, 2012, for International Application No. PCT/JP2011/079841.

(Continued)

*Primary Examiner* — Jacqueline F. Stephens
(74) *Attorney, Agent, or Firm* — Birch, Stewart, Kolasch & Birch, LLP

(57) ABSTRACT

A pull-on absorbent article including a front outer cover to be worn around a wearer's front side, a rear outer cover to be worn around the wearer's rear side, and an absorbent assembly fixed to the front and the rear outer cover so as to bridge them and having a pair of side seals. The length of each of the front and the outer cover in the longitudinal direction of the article is uniform in the lateral direction and larger than that of the side seals so that the front and the outer cover have extension portions that extend downward from the side seals. The extension portions of the front and/or the rear outer cover have an elasticized region extensible in the lateral direction in a region located laterally outward of each side edge of the absorbent assembly.

20 Claims, 26 Drawing Sheets

(51) Int. Cl.
*A61F 13/49* (2006.01)
*A61F 13/496* (2006.01)
*D04H 3/04* (2012.01)

(56) References Cited

U.S. PATENT DOCUMENTS

| | | | |
|---|---|---|---|
| 2005/0126689 A1 | 6/2005 | Thorson et al. | |
| 2005/0131374 A1 | 6/2005 | Otsubo et al. | |
| 2005/0131379 A1 | 6/2005 | Otsubo et al. | |
| 2006/0244166 A1 | 11/2006 | Wada et al. | |
| 2009/0143757 A1* | 6/2009 | Hornung et al. | 604/385.29 |
| 2009/0157035 A1* | 6/2009 | Ponomarenko et al. | 604/385.24 |
| 2010/0059168 A1 | 3/2010 | Endo et al. | |
| 2010/0106123 A1 | 4/2010 | Fukae | |
| 2011/0098668 A1 | 4/2011 | Thorson et al. | |
| 2011/0106039 A1 | 5/2011 | Saito et al. | |
| 2012/0310193 A1 | 12/2012 | Ostertag | |
| 2013/0046266 A1 | 2/2013 | Kawakami | |
| 2013/0060219 A1 | 3/2013 | Mukai et al. | |
| 2013/0165890 A1 | 6/2013 | Glaug et al. | |
| 2013/0289513 A1 | 10/2013 | Takino | |

FOREIGN PATENT DOCUMENTS

| | | |
|---|---|---|
| JP | 10-137288 A | 5/1998 |
| JP | 2002/273808 A | 9/2002 |
| JP | 2003-38556 A | 2/2003 |
| JP | 2005-279077 A | 10/2005 |
| JP | 2007-509725 A | 4/2007 |
| JP | 2008-508082 A | 3/2008 |
| JP | 2008-131968 A | 6/2008 |
| JP | 2008-132023 A | 6/2008 |
| JP | 2008-136793 A | 6/2008 |
| JP | 2008-142341 A | 6/2008 |
| JP | 2008-161514 A | 7/2008 |
| JP | 2008-178682 A | 8/2008 |
| JP | 2008-194160 A | 8/2008 |
| JP | 2008-307272 A | 12/2008 |
| JP | 2009-106666 A | 5/2009 |
| JP | 2009-153841 A | 7/2009 |
| JP | 2009-160128 A | 7/2009 |
| JP | 2009-195647 A | 9/2009 |
| JP | 2010-158590 A | 7/2010 |
| JP | 2011-25006 A | 2/2011 |
| JP | 4659109 B2 | 3/2011 |
| RU | 2 358 701 C2 | 6/2009 |
| WO | WO 2004/054490 A1 | 7/2004 |
| WO | WO 2006/017718 A1 | 2/2006 |
| WO | WO 2008/108270 A1 | 9/2008 |
| WO | WO 2009/122803 A1 | 10/2009 |

OTHER PUBLICATIONS

International Preliminary Report on Patentability and Translation of the Written Opinion of the International Searching Authority, dated Feb. 23, 2012, for corresponding International Application No. PCT/JP2010/060991.
International Search Report, PCT/JP2010/060991, Sep. 28, 2010.
Notice of Allowance dated Jan. 13, 2015, for copending U.S. Appl. No. 13/976,847.

* cited by examiner

PULL-ON ABSORBENT ARTICLE AND METHOD OF MAKING THE SAME

TECHNICAL FIELD

The present invention relates to a pull-on (pants type) absorbent article, such as a pull-on disposable diaper, and a method of making the same.

BACKGROUND ART

A pull-on absorbent article is known, which includes an hourglass-shaped outer cover having a front portion, a crotch portion, and a rear portion adapted to be applied to the front side, crotch, and rear side, respectively, of a wearer and an absorbent assembly fixed to the inner side of the outer cover, with both the lateral side edges of the outer cover in the front portion and those in the rear portion being joined together to form a waist opening and a pair of leg openings.

Continuous production of such pull-on absorbent articles generally includes the steps of making through-holes or cutouts in a continuous length of outer cover to form leg openings (trimming step) and removing the unnecessary parts (trimmings).

Conventional pull-on absorbent articles include those in which the outer cover is separated into a front side outer cover to be worn around the front side of a wearer and a rear side outer cover to be worn around the rear side of the wearer, and the absorbent assembly is fixed to bridge the front side outer cover and the rear side outer cover, with both lateral side edges of the front side outer cover and those of the rear side outer cover being joined together so that the front and the rear side outer cover are connected to make a loop. An example of this type of pull-on absorbent articles is the disposable pull-on garment disclosed in patent literature 1 (see below), which has a ring-like elastic belt composed of a front belt portion and a back belt portion and an absorbent main body, the back belt portion (i.e., rear side outer cover) having a larger length in the longitudinal direction than the front belt portion (i.e., front side outer cover) in the longitudinal direction.

Another example is the disposable pull-on diaper disclosed in patent literature 2 (see below), which includes a cylindrical below-waist portion foamed of a front outer cover sheet and a rear outer cover sheet and an absorbent assembly, wherein the rear outer cover sheet includes a main portion and a rear extension portion extending downward from the main portion. The rear extension portion includes a buttock covering subportion on both sides thereof, and second elastic members disposed in the buttock covering subportions have a higher stretch ratio than the first elastic members disposed in the middle part and the lower end part of the main portion of the rear outer cover.

Patent literature 3 (see below) describes a garment, which is not of the type having an outer cover separated into a front outer cover and a rear outer cover, having auxiliary elastic members between an outer and an inner sheet of the outer cover, wherein the auxiliary elastic member has both ends thereof secured to the outer and inner sheets at opposite sides of the below-waist portion of the garment, with a middle portion between the two ends being not secured to either the outer sheet or the inner sheet.

Patent literature 4 (see below) describes a disposable diaper, which is not of the type having an outer cover separated into a front outer cover and a rear outer cover, in which elastic members disposed between sheets of an exterior laminate (outer cover) are cut in a region overlapping the front portion of the absorbent assembly to provide a non-elasticized region, the non-elasticized region having a gradually increasing width from its end closer to the waist opening edge of the front portion to the middle thereof and a uniform width from the middle to the opposite end closer to the longitudinal center of the diaper.

The assignee common to this application previously proposed absorbent articles, like a disposable diaper, including an absorbent assembly and an outer cover, in which the outer cover has a specifically configured composite stretch panel forming a below-waist gather in the below-waist portion thereof (see patent literatures 5 and 6 below). The composite stretch panel used in these absorbent articles is composed of an outer sheet and an inner sheet bonded to each other at bonds discretely arranged in the stretch direction and a direction perpendicular to the stretch direction. Elastic members are disposed at positions other than the bonds and not fixed to either the outer sheet or the inner sheet at other than their opposite ends so that each of the outer sheet and the inner sheet may form a plurality of folds continuously extending across a plurality of the elastic members.

Patent literature 7 below discloses a pull-on article having an outer cover composed of two sheets discretely bonded to each other at bonds formed by embossing and elastic members passing between the bonds. Separately from the bonds formed by embossing, the outer cover has fixing points arranged along the curving edge forming each leg opening where one end each of elastic members is fixed.

CITATION LIST

Patent Literature

Patent literature 1: WO2006/017718
Patent literature 2: JP 2008-178682A
Patent literature 3: JP 2003-38556A
Patent literature 4: JP 2002-273808A
Patent literature 5: JP 2008-132023A
Patent literature 6: JP 2008-131968A
Patent literature 7: JP 2008-161514A

SUMMARY OF INVENTION

Technical Problem

A pull-on absorbent article of the type in which the outer cover is separated into two parts: a front outer cover worn around the front side of a wearer and a rear outer cover worn around the back side of the wearer, is advantageous in that the need to trim a continuous length of outer cover may be eliminated, or the size of cutouts may be reduced but, in turn, disadvantageous in that it tends to slide down unless provided with an increased constrictive force around the waist opening and/or the leg openings.

The pull-on garment of patent literature 1 provides improved coverage on wearer's buttocks because of the longer length of the back belt portion than the front belt portion (i.e., front outer cover). Nevertheless, this article still has the sliding down problem unless provided with an increased constrictive force around the waist opening and/or the leg openings.

The pull-on diaper of patent literature 2 is designed to prevent the rear extension portion of the rear outer cover from bulging or turning outward by adjusting the stretch ratio of the elastic members disposed in the rear extension portion. Patent literature 2 discloses an embodiment in which the front outer cover also has a front main portion forming a cylindrical below waist portion and a front extension portion extending downward from the main portion. However, the outer cover of the pull-on diaper of patent literature 2 has a decreasing width in its extension portion toward the crotch portion. That is, complete elimination of the need to trim is not accomplished.

Accordingly, the present invention relates to, in its first aspect, a pull-on absorbent article which is of the type wherein the outer cover is separated into a front outer cover adapted to be worn around the front of a wearer and a rear outer cover adapted to be worn around the rear of the wearer and is yet successfully prevented from sliding down.

Although pull-on absorbent articles of the type having independent front and rear side outer covers offer the advantage of removing the need to trim a continuous length of outer cover or reducing the size of unnecessary parts to be trimmed off, they frequently look like out-of-date loincloth while worn, which does not suit many consumers' preference.

The pull-on garment of patent literature 1 provides improved coverage on wearer's buttocks because of the longer length of the back belt portion than the front belt portion (i.e., front outer cover). However, the pull-on garment of patent literature 1 does not look good either, particularly when seen from the front.

The inventors of the present invention studied pull-on absorbent articles in which each of the front and the rear outer cover has an extension portion extending downward from the lower end of side seals. They found as a result that a mere extension looks unattractive, while the appearance like loincloth is gotten rid of.

Patent literature 3 gives no suggestion about the appearance problem associated with absorbent articles, such as diapers, having independent front and rear outer covers.

Accordingly, the invention relates to, in a second aspect, a pull-on absorbent article which is of the type wherein the outer cover is separated into a front outer cover adapted to be worn around the front of a wearer and a rear outer cover adapted to be worn around the rear of the wearer and is yet excellent in appearance.

As stated, although pull-on absorbent articles of the type having independent front and rear side outer covers offer the advantage of removing the need to trim a continuous length of outer cover or reducing the size of unnecessary parts to be trimmed away, there still is a room for improvement on appearance around the crotch portion and body fit. This applies to the pull-on garment of patent literature 1.

The disposable diaper described in patent literature 4 is not of the type having independent front and rear outer covers and neither does contemplate improvements on appearance around the crotch portion and body fit.

Accordingly, the invention relates to, in a third aspect, a pull-on absorbent article which is of the type wherein the outer cover is separated into a front outer cover adapted to be worn around the front of a wearer and a rear outer cover adapted to be worn around the rear of the wearer and yet provides improved appearance and/or fit around the crotch portion.

The absorbent articles described in patent literatures 5 and 6 have a below-waist gather formed by the specifically configured composite stretch panel in the below-waist portion thereof. The outer cover contains vacant spaces defined by the folds of the outer sheet and the oppositely facing folds of the inner sheet so that when, in particular, the inner sheet is an air-permeable sheet, the absorbent articles provide excellent protection against skin overhydration. There still is, however, a demand for a technique to stably manufacture absorbent articles with further improved protection against skin overhydration as well as good appearance. The pull-on article of patent literature 7 requires precise positional control in forming the fixing points for fixing one end of the individual elastic members.

As stated, although pull-on absorbent articles of the type having independent front and rear outer covers offer the advantage of removing the need to trim a continuous length of outer cover or reducing the size of unnecessary parts to be trimmed away, conventional pull-on absorbent articles of this type, for example, the pull-on garment of patent literature 1 leaves room for improvement in the prevention of skin overhydration.

Accordingly, the invention relates to a method for efficiently producing a pull-on absorbent article that provides a good appearance, good protection against skin overhydration, and wearer comfort.

Solution to Problem

The invention provides, in its first aspect, a pull-on absorbent article including a front outer cover adapted to be worn around applied to a wearer's front side, a rear outer cover adapted to be worn around the wearer's rear side, and an absorbent assembly fixed to the front and the rear outer cover so as to bridge them. The article has a pair of side seals formed by joining the front outer cover and the rear outer cover along their lateral side edges extending in the longitudinal direction of the article. Each of the front and the outer cover is longer than the side seals in the longitudinal direction of the absorbent article and has an extension portion extending downward from the side seals. The extension portion of the front outer cover and/or the extension portion of the rear outer cover has extensibility and contractibility in the lateral direction of the absorbent article.

The invention also provides a method of making the above described pull-on absorbent article. The method includes the steps of fixing an absorbent assembly to a continuous front outer cover and a continuous rear outer cover so as S to bridge them while continuously advancing the continuous front outer cover and the continuous rear outer cover at a predetermined distance therebetween to make a continuous-form diaper, folding the continuous-form diaper in two, forming side seals extending short of the whole width of each of the front and the rear outer cover of continuous form in the folded continuous-form diaper, and cutting the continuous form diaper having the side seals into individual diapers.

The invention also provides, in its second aspect, a pull-on absorbent article including a front outer cover adapted to be worn around a wearer's front side, a rear outer cover adapted to be worn around the wearer's rear side, and an absorbent assembly fixed to the front outer cover and the rear outer cover so as to bridge them. The article has a pair of side seals formed by joining the front outer cover and the rear outer cover along their lateral side edges extending in the longitudinal direction of the article. Each of the front and the outer cover is longer than the side seals in the longitudinal direction of the absorbent article and has an extension portion extending downward from the side seals. The extension portion of the front outer cover includes two sheets and at least one elastic member between the two sheets. The at least one elastic member is fixed to the two sheets at an end fixing part provided at or near each side edge of the front outer cover and not fixed to either of the two sheets between the end fixing parts. The two sheets of the extension region of the front outer cover are bonded to each other in a region that overlaps the absorbent assembly at a linear bond extending in the diaper lateral direction.

The invention provides, in its third aspect, a pull-on absorbent article including a front outer cover adapted to be worn around the wearer's front, a rear outer cover adapted to be worn around the wearer's rear, and an absorbent assembly fixed to the front outer cover and the rear outer cover so as to bridge them, the front outer cover and the rear outer cover being connected to each other to make a loop. The front and/or the rear outer cover has/have a first elasticized region extensible in the lateral direction of the absorbent article and located closer to the crotch portion of the absorbent article than the respective longitudinal ends of the absorbent assembly and a second elasticized region extensible in the lateral direction of the absorbent article and located closer to the crotch portion than the first elasticized region. Each of the first and the second elasticized region includes two sheets and an elastic member disposed therebetween in its stretched state and has a non-elasticized subregion formed by cutting the elastic member in an area overlapping the absorbent assembly and a pair of elasticized subregions located one on each side of the non-elasticized subregion. The non-elasticized subregion of the first elasticized region and the non-elasticized subregion of the second elasticized region have different lengths in the lateral direction of the absorbent article.

The invention also provides a method of producing the above described pull-on absorbent article. The method includes the steps of superposing two continuous sheets, one as a precursor of the front outer cover and the other as a precursor of the rear outer cover, with elastic members disposed therebetween, introducing the superposed continuous sheets between a roller having, on its peripheral surface, projections for cutting elastic members and a facing roller to cut the elastic members at positions within an area corresponding to the non-elasticized subregions of the first and the second elasticized region in each of the front and the rear outer cover, and, after the step of cutting the elastic members, cutting the two continuous sheets into the front outer cover and the rear outer cover.

The invention also provides, in its fourth embodiment, a method for producing a pull-on absorbent article comprising a front outer cover adapted to be worn around a wearer's front side, a rear outer cover adapted to be worn around the wearer's rear side, and an absorbent assembly fixed to the front outer cover and the rear outer cover so as to bridge them, the article having a pair of side seals formed by joining the front outer cover and the rear outer cover along their lateral side edges. The method includes the steps of superposing two continuous sheets with a plurality of elastic members disposed therebetween, bonding the continuous sheets to each other in parts to make a composite sheet by forming bonds such that the bonds are discretely arranged in the machine direction to make at least three rows of bonds and that every elastic member is sandwiched between adjacent two of the rows of bonds, cutting the composite sheet in half to obtain two narrower continuous sheets in a way that every bond making up one of the rows of bonds is cut in two in the cross-machine direction, fixing an adsorbent assembly to the narrower continuous sheets so as to bridge them while advancing the narrower continuous sheets at a predetermined distance from each other to make a continuous-form absorbent article, folding the continuous-form absorbent article in two, and forming side seals in the continuous-form absorbent article and cutting the continuous-form absorbent article to obtain individual pull-on absorbent articles.

BRIEF DESCRIPTION OF DRAWINGS

FIG. 1(a), FIG. 1(b), and FIG. 1(c) each illustrate a disposable pull-on diaper according to an embodiment of the invention while in use (while worn), of which FIG. 1(a) is a view from the front of a wearer, FIG. 1(b) is a side view, and FIG. 1(c) is a view from the rear of a wearer.

FIG. 4(a) and FIG. 4(b) each show a lateral cross-section of an elasticized extension region in the disposable pull-on diaper shown in FIGS. 1(a) to 1(c), of which FIG. 4(a) represents a state in which elastic members 24 are straightened up to unfold the elasticized extension region, and FIG. 4(b) represents a state in which the elastic members 24 contract to form folds 29.

FIG. 10(a), FIG. 10(b), and FIG. 10(c) each illustrate a disposable pull-on diaper according to an embodiment of the invention while in use (while worn), of which FIG. 1(a) is a view from the front of a wearer, FIG. 1(b) is a side view, and FIG. 1(c) is a view from the rear of a wearer.

FIG. 14(a) and FIG. 4(b) each show a lateral cross-section of an elasticized extension region in the disposable pull-on diaper shown in FIGS. 10(a) to 10(c), of which FIG. 14(a) represents a state in which elastic members 24 are straightened up to unfold the elasticized extension region, and FIG. 14(b) represents a state in which elastic members 24 contract to form folds 29.

FIG. 17(a), FIG. 17(b), and FIG. 17(c) each present a disposable pull-on diaper according to an embodiment of the invention while in use (while worn), of which FIG. 17(a) is a view from the front, FIG. 17(b) is a side view, and FIG. 17(c) is a view from the rear.

FIG. 21(a) and FIG. 21(b) each show a lateral cross-section of the rear elasticized extension region of the disposable pull-on diaper shown in FIGS. 17(a) to 17(c), of which FIG. 21(a) represents a state in which elastic members 24 are straightened up to unfold the elasticized extension region, and FIG. 21(b) represents a state in which the elastic members 24 contract to form folds 29.

DESCRIPTION OF EMBODIMENTS

Figure 1:
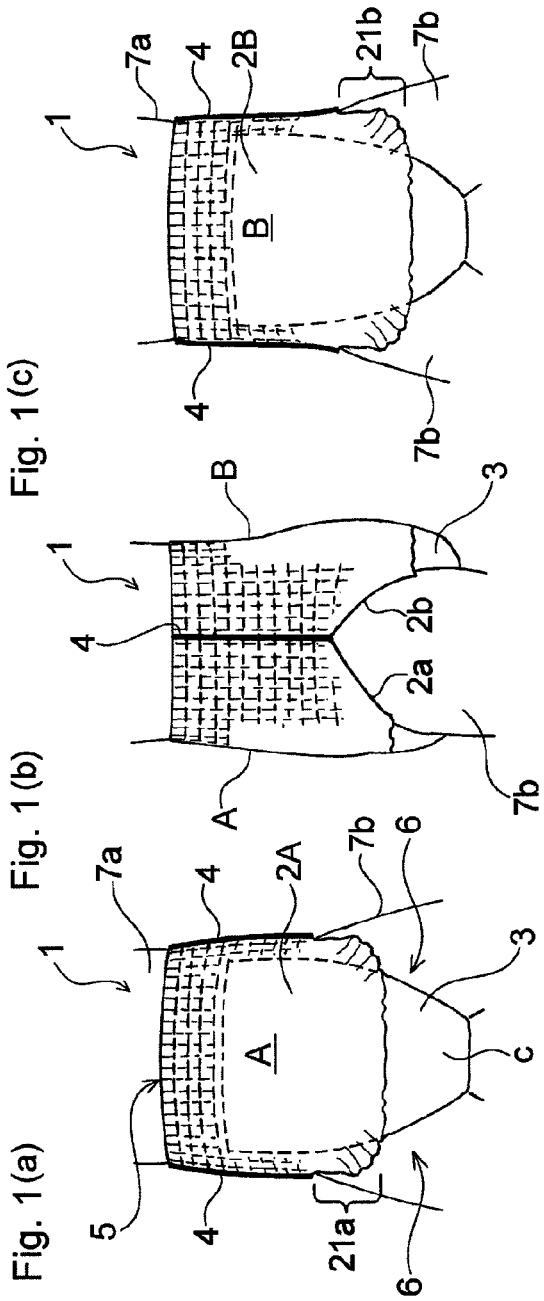

The invention will be described based on its preferred embodiments with reference to the accompanying drawings.

A disposable pull-on diaper 1 according to a first embodiment of the invention (one embodiment of the first aspect of the invention), hereinafter simply referred to as a diaper 1, includes a front outer cover 2A adapted to be worn around the wearer's front, a rear outer cover 2B adapted to be worn around the wearer's rear, and an absorbent assembly 3 fixed to the front outer cover 2A and the rear outer cover 2B so as to bridge them. Lateral side edges 2a and 2a of the front outer cover 2A and the lateral side edges 2b and 2b of the rear outer cover 2B are joined together, respectively, to form a pair of opposite side seals 4 and 4.

The front outer cover 2A and the rear outer cover 2B have a length La and Lb, respectively, greater than the length L4 of the side seals 4 in the longitudinal direction of the absorbent article. That is, the front outer cover 2A and the rear outer cover 2B have extension portions 21a and 21b, respectively, that extend downward from the side seals 4. The part of the extension portion 21a of the front outer cover 2A that is laterally outward from each lateral side edge of the absorbent assembly 3 has extensibility and contractibility in the lateral direction (direction Y) of the absorbent article. As used herein, the phrase "to have extensibility in the lateral direction of an absorbent article" is intended to mean that the part may have extensibility only in the lateral direction (direction Y), in both the lateral direction (direction Y) and the longitudinal direction (direction X), or in any planar direction.

The diaper 1 will be described in detail. As shown in FIGS. 1(a) through 1(c) and FIG. 2 the diaper 1 has a front portion A worn around the wearer's front, a rear portion B worn around the wearer's rear, and a crotch portion C located between the front portion A and the rear portion B and worn around the wearer's crotch while worn. The diaper 1 (absorbent article) in its flat-out, uncontracted state (see FIG. 2) has a longitudinal direction (direction X in FIG. 2) extending from the front portion A through the crotch portion C to the rear portion B or vice versa and a lateral direction (direction Y in FIG. 2) perpendicular to the longitudinal direction.

Figure 2:
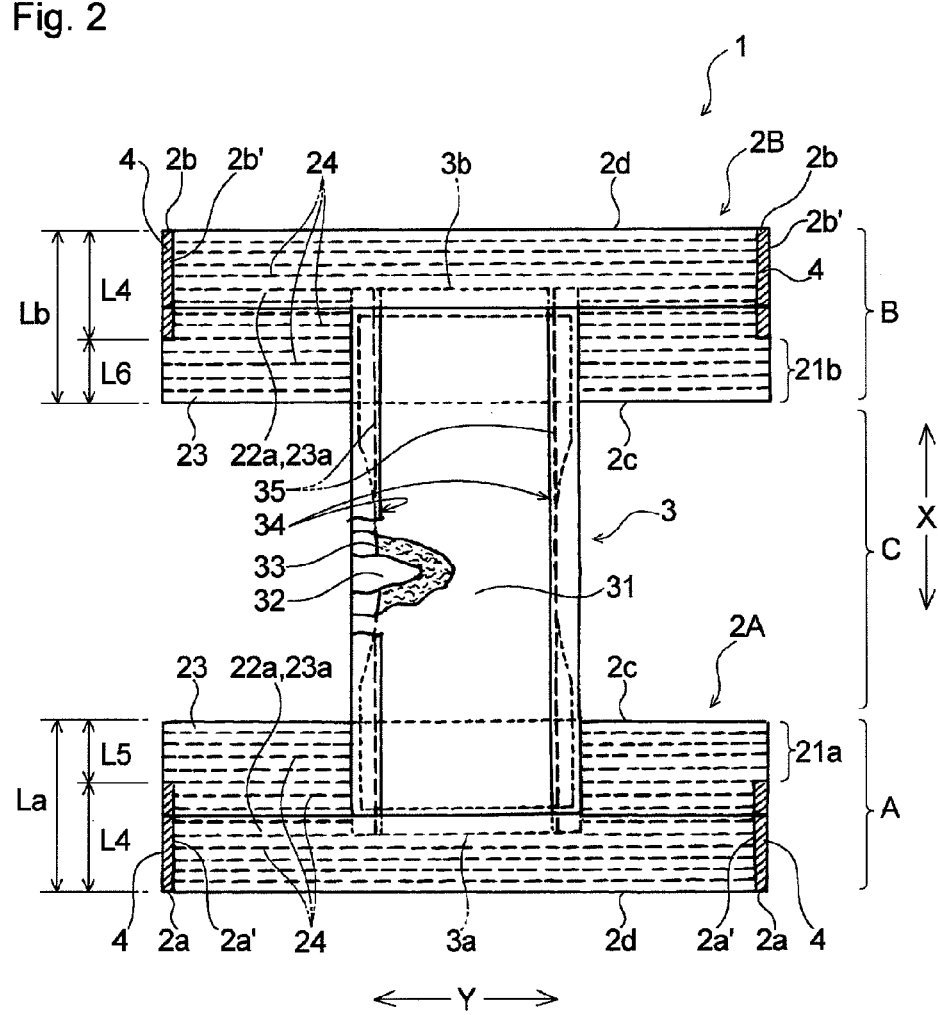
FIG. 2 is a plan of the disposable pull-on diaper shown in FIGS. 1(a) to 1(c) in its flat-out, uncontracted state with a part cut away. As used herein, the term "flat-out, uncontracted state" means a state in which a pull-on absorbent article is opened by tearing the side seals apart and with every elastic member straightened up to its design dimension (the dimension of an article in a flat-out configuration with any influences of elastic members eliminated).

As shown in FIG. 2, the absorbent assembly 3 of the diaper 1 has a rectangular shape longer in direction X and includes a liquid permeable topsheet 31, a liquid impermeable backsheet 32, and a liquid retentive absorbent core 33 interposed between the two sheets 31 and 32.

A pair of side cuffs 34 and 34 formed of a liquid resistant or water repellent and breathable material are disposed one along each lateral side edge of the absorbent assembly 3. Each side cuff 34 has an elastic member 35 provided along its free edge in a stretched state. While the diaper 1 is worn, the elastic member 35 contracts to raise the side cuff 34 to block a lateral flow of a body fluid. The topsheet 31, backsheet 32, and absorbent core 33 may be made of any material commonly used in this type of absorbent articles. Outside of the absorbent assembly 3 are provided outer covers made of, for example, nonwoven fabric or film. The outer cover may be integral with the backsheet 32.

The diaper 1 being in a flat-out, uncontracted state (see FIG. 2), the front outer cover 2A has a rectangular shape longer in the lateral direction and has opposite lateral side edges 2a and 2a extending in the diaper longitudinal direction (direction X) and opposite longitudinal end edges 2c and 2d extending in the diaper lateral direction (direction Y). Similarly, the rear outer cover 2B has a rectangular shape longer in the lateral direction, opposite lateral side edges 2b and 2b extending in the diaper longitudinal direction (direction X), and opposite longitudinal end edges 2c and 2d extending in the diaper lateral direction (direction Y). As depicted in FIG. 2, the length of each of the front outer cover 2A and the rear outer cover 2B in the diaper longitudinal direction or direction X is uniform in the diaper lateral direction (direction Y).

The front outer cover 2A and the rear outer cover 2B are bonded together along a part 2a' of each side edge 2a of the former and a part 2b' of each side edge 2b of the latter, whereby the diaper 1 has a pair of side seals 4 and 4, a waist opening 5, and a pair of leg openings 6 and 6. Bonding the front and the rear outer cover is achieved by, for example, heat sealing, high frequency sealing, ultrasonic sealing, or adhesive application. In FIGS. 1(a) through 1(c) are shown the waist opening 5 and the leg openings 6 and 6 through which the torso 7a and legs 7b and 7b of a child extend, respectively.

The absorbent assembly 3 is fixed at one longitudinal end portion thereof (the portion overlapping the front outer cover 2A) to the lateral (direction Y) middle portion of the front outer cover 2A with an adhesive, with the opposite end portion (the portion overlapping the rear outer cover 2B) being fixed to the lateral (direction Y) middle portion of the rear outer cover 2B with an adhesive.

In the cases where the front outer cover 2A and the rear outer cover 2B form a gather by the contraction of the elastic members 24 having been secured in their stretched state, they are preferably rectangular, longer in the lateral direction, with their elastic members 24 stretched, as shown in FIG. 2. In the cases where extensibility and contractibility are exerted by elastic filaments and the like having been secured in their substantially unstretched state to extensible nonwoven fabric as in a third embodiment of the invention hereinafter described, the front and the rear outer cover 2A and 2B are preferably rectangular, longer in the lateral direction, in their substantially unstretched state.

In the cases where the front or the rear outer cover is prepared by bonding an extensible sheet (such as obtained by fixing elastic filaments between two sheets of nonwoven fabric and passing the resulting composite sheet through the nip of intermeshing corrugated members to make the sheet extensible) in its stretched state to an inextensible sheet, the outer cover is preferably rectangular, longer in the lateral direction, with its extensible sheet stretched up to the length of the inextensible sheet.

As shown in FIG. 2, the side seal 4 is shorter than either the length La of the front outer cover 2A or the length Lb of the rear outer cover 2B. That is, the front and the rear outer cover 2A and 2B have extension portions 21a and 21b, respectively, that extend downward (while worn, downward in FIGS. 1(a) to 1(c)) from the side seal 4.

The front and the rear outer cover 2A and 2B of the diaper 1 each include an outer sheet 22 that defines the exterior of the diaper, an inner sheet 23 laid on the inner side of the outer sheet 22, and a plurality of elastic members 24 of thread form arranged between the two sheets 22 and 23 and have an elasticized waist region G1, an elasticized below-waist region G2, and an elasticized extension region G3.

The elasticized waist region G1 is outward from the respective longitudinal ends 3a and 3b of the absorbent assembly 3 in the diaper longitudinal direction (direction X). The elasticized extension region G3 is in the extension portion 21a of the front outer cover 2A and the extension portion 21b of the rear outer cover 2B. The elasticized below-waist region G2 is between the elasticized waist region G1 and the elasticized extension region G3 along direction X in each of the front and the rear outer cover 2A and 2B. The elasticized below-waist region G2 and the elasticized extension region G3 show extensibility in at least the region located laterally outward from each lateral side edge of the absorbent assembly 3. The position where the absorbent assembly 3 is placed is indicated by the long dashed double-dotted line in FIG. 3.

The outer and the inner sheet 22 and 23 are bonded to each other at discretely arranged bonds 26 in the elasticized waist region G1, elasticized below-waist region G2, and elasticized extension region G3. Specifically, bonds 26 are discretely arranged in lines extending in the diaper longitudinal direction (direction X), which are longitudinally spaced and laterally disposed. The positions in direction X of the bonds of a line coincide with those of the bonds of adjacent lines.

A plurality of elastic members 24 are arranged to pass between bonds 26 adjacent in the longitudinal direction in each of the elasticized regions G1 to G3. Each elastic member 24 is not fixed to either the outer sheet 22 or the inner sheet 23 at other than the fixing parts hereinafter described (an end fixing part 27 or an absorbent assembly-side end fixing part 28).

Figure 3:
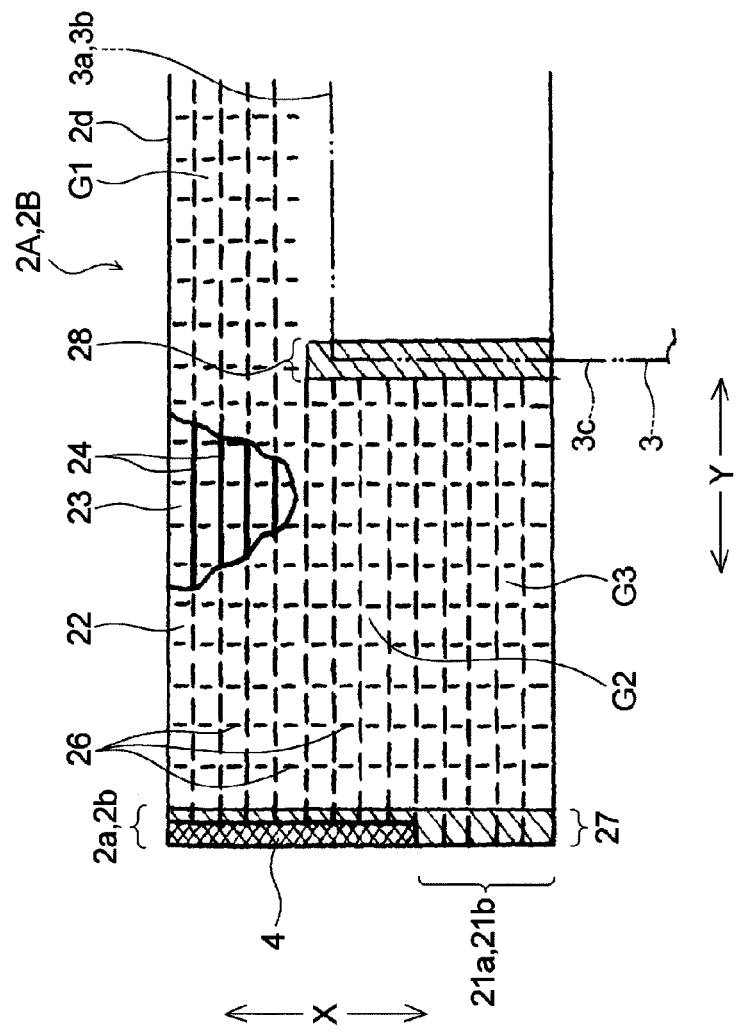
FIG. 3 is an enlarged fragmentary view of the front or the rear outer cover of the disposable pull-on diaper shown in FIGS. 1(a) to 1(c).

The elasticized waist region G1 in the front outer cover 2A has, along the lateral side edges 2a and 2a of the front outer cover 2A, an opposite pair of end fixing parts 27 in which the outer and the inner sheet 22 and 23 are bonded to each other with an adhesive (see FIG. 3). Each of the elastic members 24 disposed in the elasticized waist region G1 is secured between the sheets 22 and 23 at the opposite pair of the end fixing parts 27, while not being fixed to either the sheet 22 or the sheet 23 between the opposite end fixing parts 27. The same configuration applies to the elasticized waist region G1 in the rear outer cover 2B.

The elasticized below-waist region G2 and the elasticized extension region G3 in the front outer cover 2A each have, along the lateral side edge of the front outer cover 2A, an end fixing part 27 where the outer sheet 22 and the inner sheet 23 are bonded with an adhesive and an absorbent assembly-side fixing part 28 near the side edge 3c of the absorbent assembly 3 where the outer sheet 22 and the inner sheet 23 are bonded with an adhesive. Each of the elastic members 24 disposed in the elasticized below-waist region G2 and the elasticized extension region G3 is secured between the sheets 22 and 23 at the end fixing part 27 and at the absorbent assembly-side fixing part 28, while not being fixed to either the sheet 22 or the sheet 23 between the end fixing part 27 and the absorbent assembly-side fixing part 28. The same configuration applies to the elasticized below-waist region G2 and the elasticized extension region G3 in the rear outer cover 2B.

The absorbent assembly-side fixing part 28 may be formed to straddle the side edge 3c of the absorbent assembly 3 as is depicted in FIG. 3 or may be formed to entirely overlap the absorbent assembly 3. When the entire fixing part 28 overlaps the absorbent assembly 3, the outboard edge of the absorbent assembly-side fixing part 28 may be coincident with the side edge 3c of the absorbent assembly 3 or inboard of the side edge 3c of the absorbent assembly 3 at a prescribed distance.

Otherwise, the absorbent assembly-side fixing part 28 may be formed outboard of the side edge 3c of the absorbent assembly 3.

Figure 4:
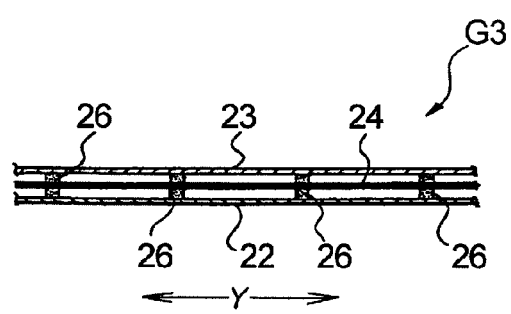
Figure 4:
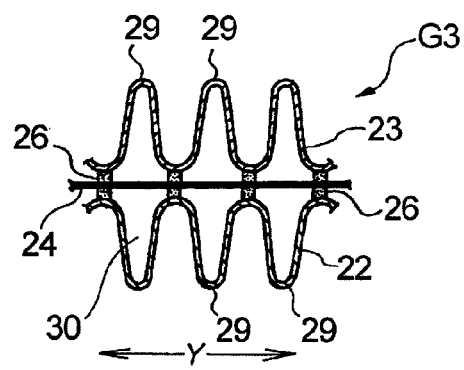

On contraction of the elastic members 24 in the elasticized waist region G1, elasticized below-waist region G2, and elasticized extension region G3, each of the sheets 22 and 23 is deformed to bulge outward to form folds 29 between every pair of adjacent lines of bonds. At the same time, vacant spaces 30 are formed between the sheets 22 and 23, being defined by every fold 29 of the sheet 22 and every fold 29 of the sheet 23 (see FIG. 4(b)). The folds 29 and the vacant spaces 30 provide improved softness of the front outer cover 2A and the rear outer cover 2B, which leads to improved feel to the touch. Furthermore, air flows easily through the valleys between the folds 29 on the skin-facing side to provide good protection against skin overhydration. When, in particular, the inner sheet 23 is formed of an air-permeable sheet, like nonwoven fabric, the humid air inside the diaper 1 escapes outside more easily.

Since the diaper 1 of the present embodiment has the extension portions 21a and 21b in the front and the rear outer cover 2A and 2B, on putting the diaper 1 on a wearer, the side edge 2a of the extension portion 21a of the front outer cover 2A and the side edge 2b of the extension portion 21b of the rear outer cover 2B on each side of the diaper 1 separate from each other toward the front and the rear in the shape of an inverted letter Y to form a downward concave edge line along the circumference of the wearer's leg 7b as shown in FIG. 1(b). Furthermore, since the extension portions 21a and/or 21b of the front and/or the rear outer cover 2A, 2B have the elasticized extension region G3, the extension portions 21a and 21b exhibits extensibility and contractibility in the diaper lateral direction so that the edges of the extension portions 21*a* and 21*b* softly apply to the upper part of the leg 7*b* to effectively prevent the diaper 1 from sliding down.

In addition, while the diaper 1 is worn, the extension and contraction stress of the elasticized extension region G3 functions to enhance the body constrictive, extension and contraction stress of the elasticized waist region G1 and the elasticized below-waist region G2 to thereby provide a better body fit.

The diaper 1 is thus successfully prevented from sliding down without excessively increasing the constrictive force around the waist opening 5 and the leg openings 6.

Since the extension portions 21*a* and 21*b* have a portion extending laterally outward from both side edges of the absorbent assembly 3, and the laterally extending portion contracts moderately, the edges 2*a* and 2*b* form the periphery of the leg opening as a unit with the absorbent assembly 3. As a result, the diaper 1 has a good appearance and does not bring a feeling of insecurity with respect to leakage.

The presence of the extension portions 21*a* and 21*b* in the front outer cover 2A and the rear outer cover 2B helps the side seals 4 to maintain relative straightness thereby to impart well-balanced and uniform constrictive force to the front and the rear portion A and B of the diaper 1.

In the diaper 1, not only the extension portion 21*a* of the front outer cover 2A but the extension portion 21*b* of the rear outer cover 2B are elasticized in the diaper lateral direction. This configuration brings about further improved effect on prevention of sliding down.

In the diaper 1, the elastic members 24 in the elasticized extension region G3 are not fixed to either the sheet 22 or 23 at other than the end fixing part 27 and the absorbent assembly-side fixing part 28. Therefore, the elastic members 24 contract with no hindrance to stably form folds, and the end fixing part 27 is pulled toward the absorbent assembly to easily form the downward concave edge line in conformity to the circumference of the leg 7*b* as shown in FIG. 1(*b*) without excessively increasing the stretch ratio of the elastic members 24.

Not being fixed at the bonds 26, each elastic member 24 is free to expand and contract over a wide range along its longitudinal direction without any restraint and also able to move in the diaper longitudinal direction (direction X) between the bonds 26 adjacent in the diaper longitudinal direction. Therefore, when the absorbent assembly having gained in weight due to absorption of discharged urine sags, the elastic members 24 are slightly slanted down to develop a pulling force toward the wearer's waist. In order for the elastic members 24 to easily move in the diaper longitudinal direction between the bonds 26, it is preferable that the distance between the bonds adjacent in the diaper longitudinal direction be 2 to 100 times, more preferably 5 to 50 times, the width (or the diameter in the case of an elastic member having a circular cross-section) of the elastic member 24 present therebetween in the diaper longitudinal direction.

Instead of being fixed between the sheets 22 and 23 at the end fixing part 27 and the absorbent assembly-side fixing part 28, the elastic members 24 in the elasticized extension region G3 may be fixed at both the opposite end fixing parts 27, not being fixed to either the sheet 22 or 23 between the end fixing parts 27. In this modification, too, the same effects are obtained.

The extensibility of each of the extension portions 21*a* and 21*b* in the diaper lateral direction is preferably such that the length of the part of each of the extension portions 21*a* and 21*b* outboard of the corresponding side edge 3*c* of the absorbent assembly in the diaper lateral direction in a relaxed state (contracted state) is 15% to 90%, more preferably 20% to 60%, even more preferably 25% to 50%, of that in a flat-out, uncontracted stated.

To further ensure one or more of the aforementioned effects, it is preferred that the extension length L5 of the extension portion 21*a* and the extension length L6 of the extension portion 21*b* of the front and the rear outer cover 2A and 2B, respectively, be in the range of from 5% to 150%, more preferably 25% to 70%, of the length L4 of the side seal 4.

For the same purpose, it is preferred that the extension length L5 of the extension portion 21*a* in the front outer cover 2A be in the range of from 5% to 60%, more preferably 20% to 40%, of the length La of the front outer cover 2A and that the extension length L6 of the extension portion 21*b* in the rear outer cover 2B be in the range of from 5% to 60%, more preferably 20% to 40%, of the length Lb of the rear outer cover 2B.

The extension lengths L5 and L6 of the extension portions 21*a* and 21*b*, respectively, are preferably 10 mm or more, more preferably 20 mm or more.

For use by children, the extension lengths L5 and L6 of the extension portions 21*a* and 21*b*, respectively, are preferably 10 to 100 mm, more preferably 20 to 70 mm. For use by adults, the extension lengths L5 and L6 of the extension portions 21*a* and 21*b*, respectively, are preferably 10 to 150 mm, more preferably 20 to 100 mm.

From the viewpoint of easing the insecurity feeling about leakage by reducing the skin exposure observed from the wearer's front, it is preferred that the extension length L5 of the extension portion 21*a* and the extension length L6 of the extension portion 21*b* be substantially equal. As used herein, the expression "substantially equal" is intended to mean that the difference in length between L5 of the extension portion 21*a* in the front outer cover 2A and L6 of the extension portion 21*b* in the rear outer cover 2B is within 5 mm.

It is also preferred that the front and the rear outer cover 2A and 2B both have the extension portions 21*a* and 21*b*, respectively, and that the extension length L6 of the extension portion 21*b* in the rear outer cover 2B be greater than the extension length L5 of the extension portion 21*a* in the front outer cover 2A. A pull-on absorbent article according to this embodiment provides coverage over the wearer's buttocks to prevent excessive skin exposure while covering the front of the wearer's crotch to some extent and thereby has a good appearance. From this point of view, the extension length L6 is more preferably 1.1 to 2.5 times the extension length L5.

In view of improvement on fit and appearance of the rear side, it is also a preferred embodiment for the pull-on absorbent article of which the extension portion 21*b* in the rear outer cover 2B is longer than the extension portion 21*a* of the front outer cover 2A to have extensibility in the extension portion 21*b* of the rear outer cover 2B but no extensibility in the extension portion 21*a* of the front outer cover 2A.

The outer sheet 22 and the inner sheet 23 are folded along the waist opening edge, i.e., the diaper end edges 2*d* over the inner sheet 23 to form folded-over panels 22*a* and 23*a*, respectively. The folded-over panels 22*a* and 23*a* are bonded to the facing inner sheet 23 at the side seals 4 and to the topsheet side of the facing absorbent assembly 3 with an adhesive.

The outer sheet 22 and the inner sheet 23 may be of any sheet material conventionally used in this type of articles but are preferably formed of nonwoven fabric. In view of softness and the like, a single sheet or a laminate of two or more sheets of nonwoven fabric, such as air-through nonwoven, heat-rolled nonwoven, hydroentangled nonwoven, spun bonded nonwoven, and melt blown nonwoven fabrics, is particularly preferred. A nonwoven fabric integrally laminated with film is also useful. The molding material of the elastic members 24 is not particularly limited and may be any of known elastic materials of various kinds that have been used in absorbent articles, such as disposable diapers and sanitary napkins. Examples of such elastic materials include synthetic rubbers, such as styrene-butadiene, butadiene, isoprene, and neoprene, natural rubber, EVA, stretch polyolefins, and polyurethane. Forms of the elastic members preferably include a thread with a rectangular, square, circular or polygonal section, tape, or multifilamentous yarn.

A preferred method for making the disposable pull-on diaper 1 of the first embodiment will then be described with reference to FIG. 5. The method according to this embodiment is a method for producing the diaper 1 in a continuous manner.

Figure 5:
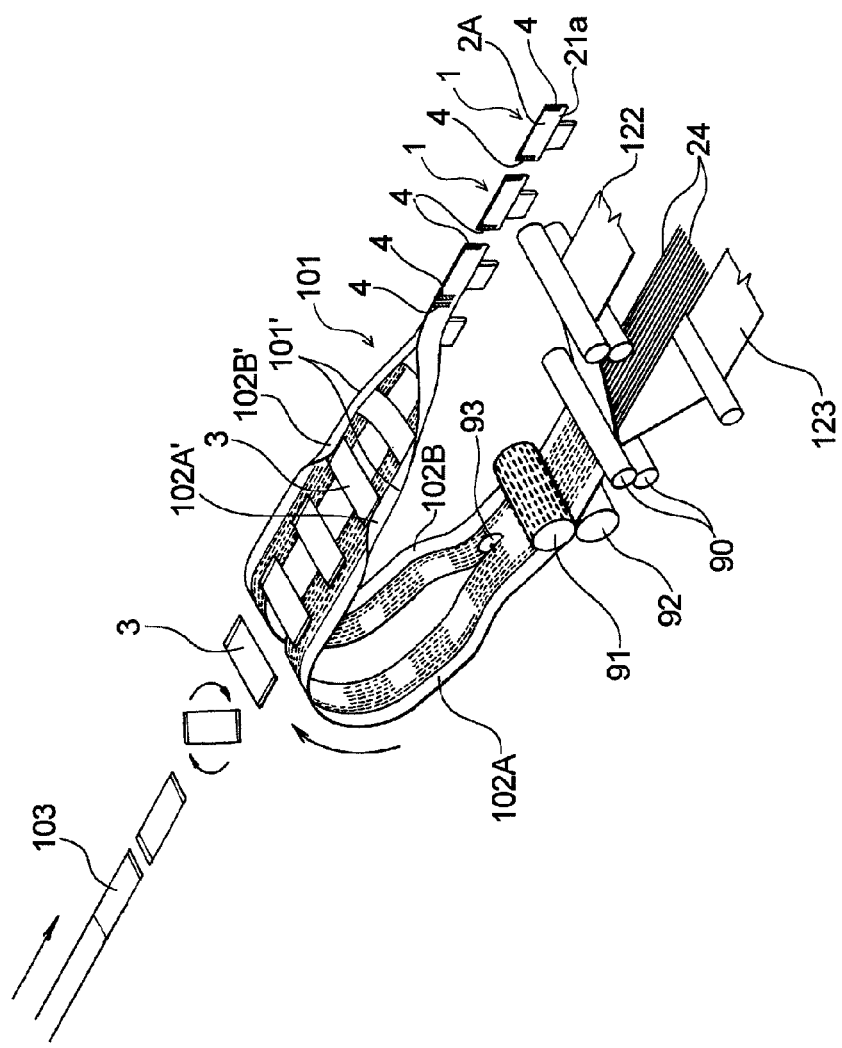
FIG. 5 illustrates a preferred method of making the disposable pull-on diaper shown in FIGS. 1(a) to 1(c).

As shown in FIG. 5, a wide continuous sheet 122 as an outer sheet precursor and a wide continuous sheet 123 as an inner sheet precursor are superposed on each other with elastic members 24 inserted therebetween in their stretched state. Before the continuous sheets 122 and 123 are superposed, an adhesive for the formation of end fixing parts 27 and absorbent assembly-side fixing parts 28 is intermittently applied to the continuous sheet 122 and/or the continuous sheet 123 by means of an unshown adhesive applicator. The two continuous sheets are pressed between a pair of nip rollers 90 to fix the elastic members 24 between the continuous sheets 122 and 123 at the fixing parts 27 and 28.

The superposed continuous sheets 122 and 123 are then introduced between a pressure roller 91 and a facing anvil roller 92 to be pressed in parts with heat. The pressure roller 91 has, on its peripheral surface, projections for forming bonds 26 and projections for cutting the elastic members 24. As a result, a large number of bonds 26 are formed, and the elastic members 24 are cut in a region where an absorbent assembly 3 is to be disposed.

The laminate of the continuous sheets 122 and 123 with the elastic members 24 therebetween is then cut by a cutting unit 93 into two continuous sheets: one as a continuous front outer cover 102A and the other as a continuous rear outer cover 102B. The continuous front outer cover 102A has a structure generally corresponding to contiguously connected front outer covers 2A of a plurality of diapers 1. The continuous rear outer cover 102B has a structure generally corresponding to contiguously connected rear outer covers 2B of a plurality of diapers 1.

The cutting unit may be a known cutting device for continuously cutting a sheet material, for example, a cutter having a cutting blade on its upstream side, a cylindrical or disc-shaped cutter having an annular blade around its peripheral surface or edge, a laser cutter, or a water jet cutter. Cutting the sheet using a cutting unit is advantageous in that the axial length of the rollers, such as the pressure roller 91, is minimized.

While the continuous front outer cover 102A and the continuous rear outer cover 102B are advanced at a predetermined distance therebetween, an adsorbent assembly 3 is fixed to the continuous front outer cover 102A and the continuous rear outer cover 102B so as to bridge the two outer covers. To achieve this, an adhesive is previously applied to the backsheet side of the adsorbent assembly 3 and/or the facing surface of the continuous outer covers 102A and 102B. In the present embodiment, side portions 102A' and 102B' along the moving edge of the continuous front and the outer cover 102A and 102B, respectively, are folded over and fixed to the respective end portions of the absorbent assembly 3.

The continuous-form diaper 101 thus obtained is then folded in two, followed by forming side seals 4 and 4 by heat sealing, ultrasonic sealing, high frequency sealing, adhesive application, or a combination of such means. The side seals 4 and 4 are preferably formed using an unshown sealing unit having a pair of sealing rollers. The continuous-form diaper 101 is folded in two with edges (i.e., the folded edges 101' resulting from folding the side portions 102A' and 102B' of the continuous front and the rear outer cover 102A and 102B) even.

After the formation of the side seals 4 and 4, the continuous-form diaper 101 is cut to size using a known cutting means (not shown) to obtain individual disposable pull-on diapers 1 having the aforementioned structure. The side seals 4 and 4 should be formed not to extend over the whole width of the continuous front outer cover 102A and the continuous rear outer cover 102B so that the diaper 1 may have the above-described extension portions 21$a$ and 21$b$ in the front and the rear outer cover 2A and 2B thereof, respectively.

In carrying out the method of the present embodiment, the undescribed details are the same as those in conventional production of disposable pull-on diapers in what we call a lateral feed system. For instance, the absorbent assembly 3 that is to be disposed on the continuous front outer cover 102A and the continuous rear outer cover 102B is obtained by making a continuous-form absorbent assembly 103 having absorbent assemblies contiguously connected end-to-end in a known manner and cutting the continuous form to provide an absorbent assembly for each diaper. The resulting individual absorbent assemblies 3 may be turned 90° and spacedly disposed on the continuous front outer cover 102A and the continuous rear outer cover 102B.

Thus, the diaper 1 of the first embodiment can be produced without trimming the outer cover-forming continuous sheets 122 and 123 to form the leg openings. Therefore, the steps associated with removal and recycling of trimmings are unnecessary, and the diaper 1 is produced efficiently and economically. To produce no trimmings is environmentally friendly.

A second and a third embodiment of the invention (embodiments of the first aspect of the invention) will be described.

Description of the disposable pull-on diapers of the second and the third embodiment will generally be confined to the differences from the first embodiment, with the details in common omitted. The description of the first embodiment applies to the second and the third embodiment with the exceptions noted hereunder. The elements or members of the second and the third embodiment common to the first embodiment are identified with the same reference numerals as in the first embodiment.

In the disposable pull-on diaper of the second embodiment, each of the elasticized waist region G1, the elasticized below-waist region G2, and the elasticized extension region G3 in each of the front outer cover 2A and the rear outer cover 2B has a structure composed of an outer sheet 22 that defines the exterior of the diaper and an inner sheet 23 on the inner side of the outer sheet 22 bonded to each other over the entire area with elastic members 24 secured between the two sheets 22 and 23 over the entire area. The elastic members 24 are secured between the sheets 22 and 23 in their stretched state in the diaper manufacturing.

In the second embodiment, each of the elasticized waist region G1, the elasticized below-waist region G2, and the elasticized extension region G3 forms irregular creases or folds by the contraction of the elastic members 24 but does not form such vacant spaces as in the first embodiment.

In the second embodiment, the front and the rear outer cover 2A and 2B each have an extension portion 21a and 21b below the side seals 4, and the part of the extension portion 21a of the front outer cover 2A that does not overlap the absorbent assembly 3 is elasticized in the diaper lateral direction. As a result, the disposable pull-on diaper of the second embodiment exhibits the same effects as of the first embodiment.

The disposable pull-on diaper of the second embodiment can be produced in the same manner as for the diaper 1 with the following exceptions. An adhesive is applied to the wide continuous sheet 122 as an outer sheet precursor and/or the wide continuous sheet 123 as an inner sheet precursor in other than the area where the absorbent assembly 3 is to be placed before they are joined. The continuous sheets 122 and 123 are pressed under a pressure roller 91 having only projections for cutting the elastic members 24 so that the elastic members 24 are cut in the area where the absorbent assembly 3 is to be placed.

In the disposable pull-on diaper of the third embodiment, each of the front and the rear outer cover 2A and 2B is an extensible sheet obtained by fixing a number of elastic filaments in a parallel configuration to extensible nonwoven fabric in their substantially unstretched state over their whole length. A suitable example of such an extensible sheet is described in JP 2008-179128A. The extensible sheet is preferably composed of two sheets of nonwoven fabric, which may be the same or different, and the elastic filaments therebetween. The elastic filaments may be synthetic or natural rubber threads or filaments obtained by dry spinning (e.g., melt spinning) or wet spinning. It is preferable that the elastic filaments obtained by melt spinning are directly fed onto the nonwoven fabric without being once taken-up or stocked. An extensible sheet in which elastic filaments, either continuous or staple, are randomly arranged may also be useful.

The extensible sheet for use in the third embodiment is preferably, for example, an extensible sheet composed of two sheets of nonwoven fabric: a first nonwoven fabric and a second nonwoven fabric and a number of elastic filaments sandwiched between the two sheets. The first and the second nonwoven fabric may be the same or different. When the two nonwoven fabrics are said to be "the same", this means that they are totally equal in all the attributes including production process, material, thickness and length of constituent fibers, thickness, and basis weight. Two nonwoven fabrics different in any one of these attributes are regarded to be different. Both the first and the second nonwoven fabric are extensible. The term "extensible" as used herein with respect to nonwoven fabrics is contemplated to include not only a nonwoven fabric whose constituent fibers per se are extensible but also a nonwoven fabric whose constituent fibers are not per se extensible but which shows extensibility as a whole as a result of debonding of constituent fibers that have been bonded at their intersections, structural change of a three-dimensional structure formed of a plurality of fibers bonded to one another, breaks of the constituent fibers, or straightening out of slack fibers. The nonwoven fabrics may have extensibility or be made extensible before the elastic filaments are bonded thereto (in the form of stock roll). Alternatively, the nonwoven fabrics may be inextensible before the elastic filaments are bonded thereto and, after being joined with the elastic filaments, be subjected to processing to be made extensible. Methods for making a nonwoven fabric extensible include heat treatment, stretching between spaced pairs of rollers, stretching by a bite between corrugating members (such as gears), and stretching by a tenter. It is preferred that the nonwoven fabrics not be extensible in the form of stock roll so that they may be conveyed stably during fusion bonding the elastic filaments to the nonwoven fabrics.

In the third embodiment, too, the front and the rear outer cover 2A and 2B each have an extension portion 21a and 21b below the side seals 4, and the parts of the extension portion 21a of the front outer cover 2A that do not overlap the absorbent assembly 3 are elasticized in the diaper lateral direction. Therefore, the disposable pull-on diaper of the third embodiment exhibits the same effects as of the first embodiment.

The disposable pull-on diaper of the third embodiment can be produced by, for example, the method shown in FIG. 5, except that, instead of the continuous front outer sheet 102A and the continuous rear outer sheet 102B, two continuous extensible sheets, such as those described in JP 2008-179128A, are fed to the zone where the absorbent assembly 3 is fixed. The machine direction of the extensible sheets is preferably coincident with the extending direction of the elastic filaments.

Fourth to sixth embodiments of the invention (embodiments of the first aspect of the invention) will then be described. Description of the disposable pull-on diapers of the fourth to sixth embodiments will generally be confined to the differences from the first embodiment, with the details in common omitted. The description of the first embodiment applies to the fourth to sixth embodiments with the exceptions noted hereafter. The elements or members of the forth to sixth embodiments common to the first embodiment are identified with the same reference numerals as in the first embodiment.

Figure 6:
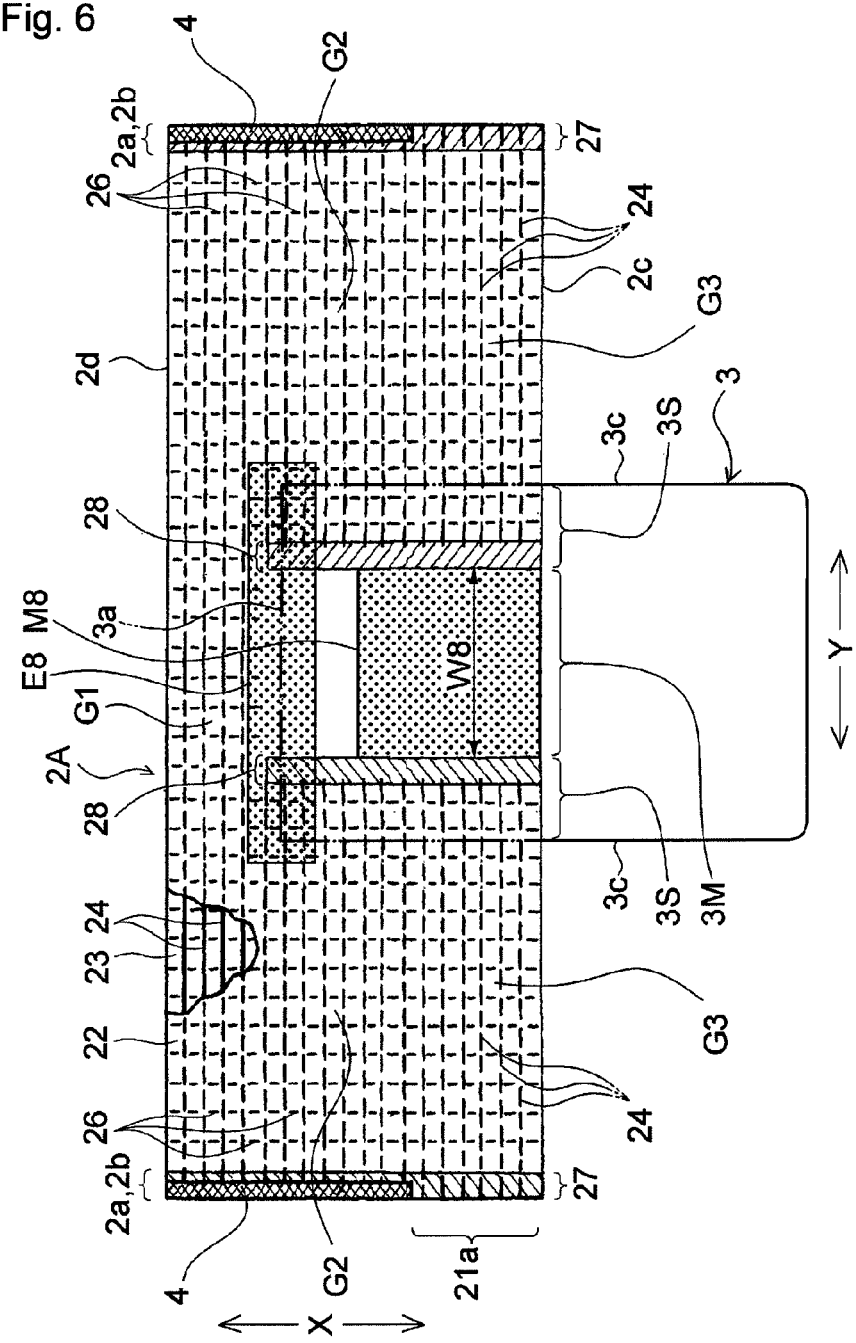
FIG. 6 is a plan of a disposable pull-on diaper according to another embodiment of the invention, seen from the front outer cover side, with a part cut away.

In the disposable pull-on diaper of the fourth embodiment, as shown in FIG. 6, two sheets 22 and 23 that make the extension portion 21a of the front outer cover 2A are bonded at end fixing parts 27, absorbent assembly-side fixing parts 28, and a number of discretely formed bonds 26. In the elasticized extension region G3, each elastic member 24 is fixed between the sheets 22 and 23 at the end fixing part 27 and the absorbent assembly-side fixing part 28 while not being fixed to either the sheet 22 or 23 between the end fixing part 27 and the absorbent assembly-side fixing part 28.

As shown in FIG. 6, the absorbent assembly-side fixing part 28 in the extension portion 21a of the front outer cover wholly overlaps the absorbent assembly 3, and the elastic members 24 having been fixed in their stretched state retract to contract both the sheets 22 and 23 in the area overlapping the absorbent assembly 3 as well as in the other area of the elasticized extension region G3.

Not being segmented by the bonds 26, each elastic member 24 is free to expand and contract over a wide range along its longitudinal direction. Not being fixed at the bonds 26, each elastic member 24 is also able to move in the diaper longitudinal direction (direction X) between the bonds 26 adjacent in the diaper longitudinal direction. Therefore, when the absorbent assembly having gained in weight due to absorption of discharged urine sags, the elastic members 24 are slightly slanted down to develop a pulling force toward the wearer's waist. In order for the elastic members 24 to easily move in the diaper longitudinal direction between bonds 26 adjacent in the diaper longitudinal direction, it is preferable that the distance between the bonds adjacent in the diaper longitudinal direction be 2 to 100 times, more preferably 5 to 50 times, the width (or a diameter in the case of an elastic member having a circular cross-section) of the elastic member 24 present therebetween in the diaper longitudinal direction.

The region of the absorbent assembly 3 that overlaps the extension portion 21a of the front outer cover has a fixed middle portion 3M located in the lateral middle of the absorbent assembly 3, more specifically between the opposite absorbent assembly-side fixing parts 28. In the fixed middle portion 3M, the absorbent assembly 3 is bonded to the front outer cover 2A by means of, e.g., an adhesive. The region of the absorbent assembly 3 that overlaps the extension portion 21a also has a non-fixed side portion 3S located outboard of each side edge of the fixed middle portion 3M. In the non-fixed side portions 3S and 3S, the absorbent assembly 3 is not bonded to, and thereby separate from, the front outer cover 2A. The absorbent assembly 3 is also bonded in the vicinity of its longitudinal end 3a to the front outer cover 2A over its whole width. In detail, the inner sheet 23 has an adhesive applied to an adhesion region E8 in the vicinity of the area where the longitudinal end 3a of the absorbent assembly 3 is to be bonded. The adhesion region E8 is wider than the absorbent assembly 3. After the absorbent assembly 3 is disposed, the outer sheet 22 and the inner sheet 23 are folded along the waist opening edge, i.e., the end edge 2d onto the longitudinal end 3a of the absorbent assembly 3, whereby the longitudinal end edge 3a of the absorbent assembly 3 is covered with and bonded to the folded-over panels 22a and 23a. In FIG. 6, E8 and M8 indicate bonded regions where the absorbent assembly 3 is bonded to the front outer cover 2A.

Because the elasticized extension region G3 contracts on both sides of the absorbent assembly 3, especially in the area corresponding to the non-fixed side portions 3S, the lower part of the outer cover 2A is pulled more strongly toward the lateral middle (the absorbent core) of the absorbent assembly 3. As a result, the diaper looks even better.

In the fourth embodiment, the geometry of the bonded region between the absorbent assembly 3 and the front outer cover 2A is different from that between the absorbent assembly 3 and the rear outer cover 2B. Specifically, the bonded region between the extension portion 21a of the front outer cover and the absorbent assembly 3 is smaller than that between the extension portion 21b and the absorbent assembly 3 in both width and area. More specifically, the absorbent assembly 3 is fixed to the extension portion 21a of the front outer cover 2A in its lateral middle portion having a width indicated by W8 in FIG. 6, while it is fixed to the extension portion 21b of the rear outer cover 2B in a bonded region whose width is greater than the width W8, for example, over the entire width between the opposite absorbent assembly-side fixing parts 28 and 28 (see FIG. 3) that are located at almost the same positions as the side edges of the absorbent assembly 3 or over the entire width thereof. The rear end portion near the end 3a of the absorbent assembly 3 is fixed to the rear outer cover over its whole width similarly to the front end portion.

According to the fourth embodiment, since the width of the bonded region between the absorbent assembly 3 and the extension portion 21a of the front outer cover is smaller than that between the absorbent assembly 3 and the extension portion 21b of the rear outer cover, the same effects as in the first embodiment are produced. The fourth embodiment additionally offers the following effects. The extension portion 21b of the rear outer cover is prevented from turning outward while avoiding reduction in coverage on wearer's buttocks. The extension portion 21a of the front outer cover is made to contract largely to some extent in the diaper lateral direction (direction Y) to be deformed in conformity to the leg circumference. As a result, a body fit improves, and the gap between the extension portion 21a and the wearer's body decreases to lessen the feeling of insecurity about leakage.

Figure 7:
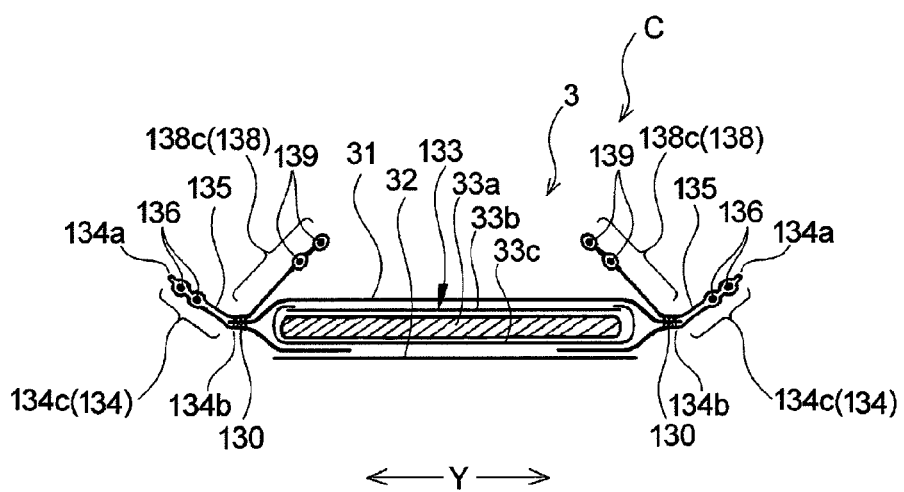
FIG. 7 is a cross-section of the crotch portion of a disposable pull-on diaper according to still another embodiment of the invention.
Figure 8:
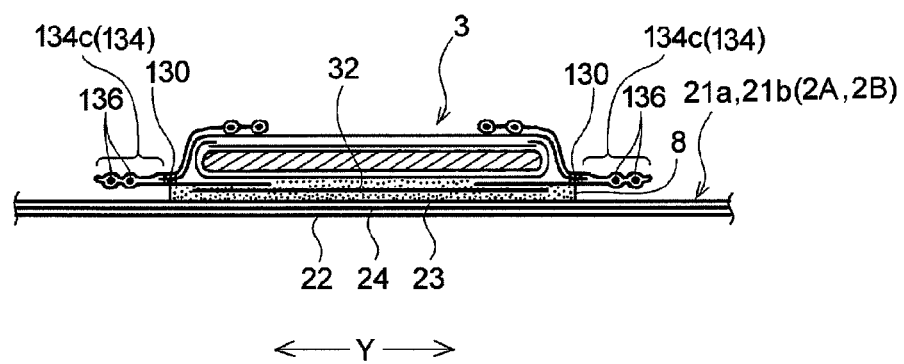
FIG. 8 is a cross-section of the extension portion of the rear or the front outer cover of the disposable pull-on diaper shown in FIG. 7.

The disposable pull-on diaper according to the fifth embodiment has, as shown in FIGS. 7 and 8, a side edge portion extending in the diaper (absorbent article) longitudinal direction and an elastic member 136 in the side edge portion. As shown in FIG. 8, each of the side edge portions of the absorbent assembly 3 where the elastic member 136 is provided is not bonded to the extension portion 21a and/or the extension portion 21b of the front outer cover 2A and/or the rear outer cover 2B. More specifically, the absorbent assembly 3 of the fifth embodiment has on each lateral side thereof a side sheet portion 134 that is located laterally outward from the side edge of the absorbent member 133 and forms a side gather 134c in the crotch portion C.

The side sheet portion 134 extends over the whole length of the absorbent assembly 3 and includes a liquid resistant or water repellent sheet 135 and elastic members 136 and 136 fixed in their stretched state to the sheet 135 as shown FIGS. 7 and 8. Two or more (two in the case illustrated) elastic members 136 are provided along each side of the absorbent assembly 3, more concretely, near along the side edge 134a of the side sheet portion 134. Each elastic member 136 is fixed in its stretched state to the crotch portion C and the extension portions 21a and 21b of the front and rear outer cover 2A and 2B to form a side gather 134c in the crotch portion C and the extension portions 21a and 21b. The side gather 134c is a result of the contraction of the elastic members 136 provided in the side sheet portion 134. On contraction of the elastic members 136, the sheet 135 forming the side sheet portion 134 gathers or is deformed into a wavy cross-section to form the side gather 134c. It suffices that the side gather 134c be formed while the diaper is in a relaxed state and/or during wear. The part of each side sheet portion 134 that is located near each of the longitudinal ends 3a and 3b of the absorbent assembly 3 is fixed in its laterally outwardly lying position to the main portion of the front and rear outer cover (the main portion of the front or the rear outer cover is the portion located between the opposite side seals 4 and 4). The part of the side gathers 134c that are located on the extension portions 21a an 21b of the front and the rear outer cover are not fixed to the extension portions 21a and 21b as shown in FIG. 8. In FIG. 8, the numeral 8 indicates an adhesive.

In the fifth embodiment, since the side edge portions of the absorbent assembly 3 having the elastic members 136 are not fixed to the extension portions 21a and 21b of the front and the rear outer cover, the same effects as in the first embodiment are produced. In addition, the diaper of the fifth embodiment provides an improved fit and improved prevention of the sliding down. The side gathers 134c fit the wearer's leg circumference while the diaper 1 is worn.

The absorbent assembly 3 used in the fifth embodiment additionally has along its sides a pair of standing gather-forming portions 138 extending in the longitudinal direction of the absorbent assembly 3. Each standing gather-forming portion 138 includes a sheet 135 and a standing gather-forming elastic member 139 fixed to the sheet 135. The standing gather-forming portion 138 forms a standing gather 138c in at least the crotch portion C. The standing gather 138c rises toward the wearer's skin while the diaper 1 is worn to block a lateral flow of a fluid. The part of each standing gather-forming portion 138 that is located between the opposite side seals 4 and 4 is fixed in its inwardly lying position to the main portion of the front and the rear outer cover. A linear bond 130 is provided along each side edge of the rectangular absorbent member 133 over the whole length of the absorbent assembly 3 as well as the absorbent member 133 in direction X. The linear bond 130 is preferably a continuous straight line but may be a dotted line. The linear bond 130 may be formed by various known methods, such as heat sealing, ultrasonic sealing, high frequency sealing, or application of an adhesive. The absorbent member 133 used in the fifth embodiment includes an absorbent core 33a formed of a fiber aggregate of pulp fiber, etc. with or without a superabsorbent polymer and core wrap sheets 33b and 33c wrapping the absorbent core 33a. The absorbent core 33a and the core wrap sheets 33b and 33c may be of any materials conventionally used in this type of absorbent articles. To provide an improved feel to the touch, an outer cover made of nonwoven fabric may preferably be provided on the part of the garment-facing side of the backsheet 32 that is located in the crotch portion C.

The structure of the absorbent assembly and the bonded region geometry of the absorbent assembly to the front and the rear outer cover in the disposable pull-on diaper of the fifth embodiment are applicable to the other embodiments of the disposable pull-on diaper of the invention. In such applications, the same effects as described will be obtained. The number of the elastic members 136 provided in each side sheet portion 134 may be one or more than two. The elastic member 136 that forms the side gather may be fixed between an extended part of the topsheet and an extended part of the backsheet each laterally extending outward from the side edge of the absorbent member 133.

While the first aspect of the invention has been described with respect to some preferred examples, the first aspect of the invention is not construed as being limited thereto, and various changes and modifications can be added thereto, for example, as follows.

It may be only one of the extension portion 21a of the front outer cover 2A and the extension portion 21b of the rear outer cover 2B that is elasticized in the lateral direction of the absorbent article in the regions outboard of the side edges 3c of the absorbent assembly 3.

Figure 9:
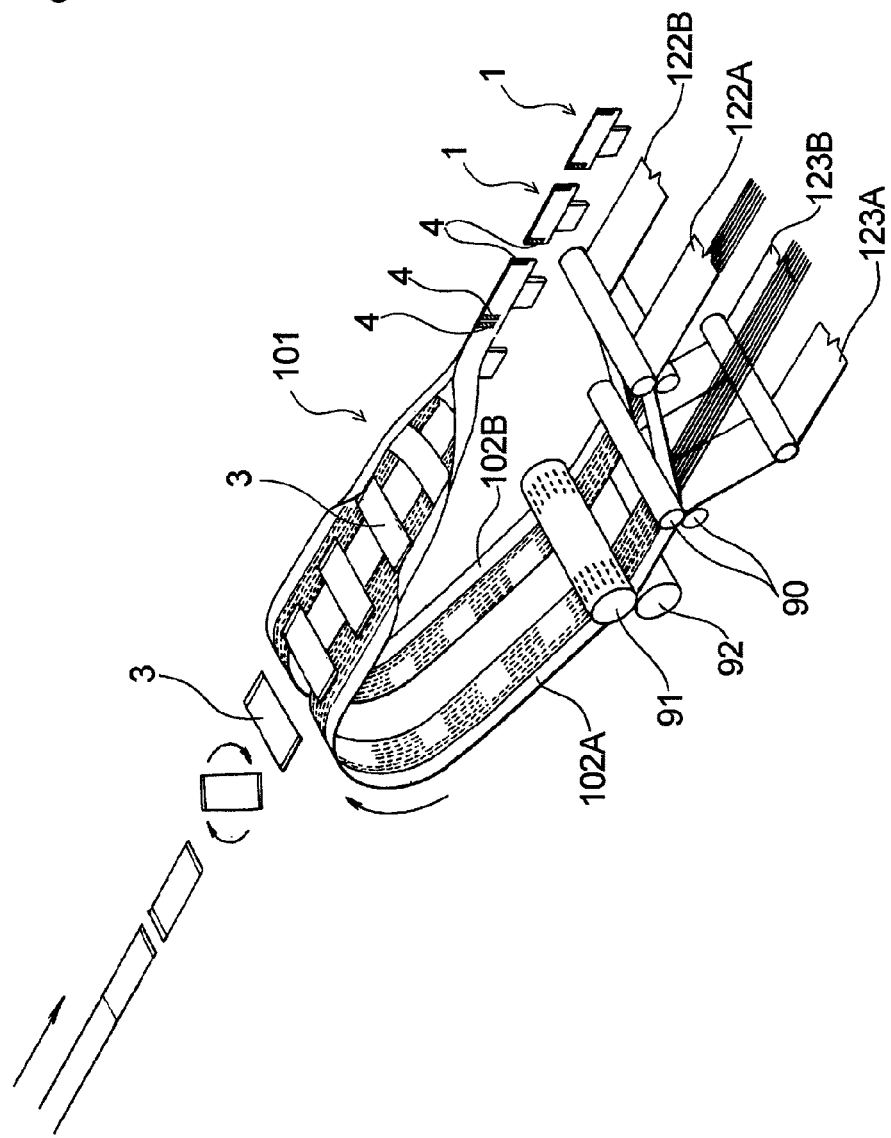
FIG. 9 illustrates another preferred method for making the disposable pull-on diaper shown in FIGS. 1(a) to 1(c).

In the method of producing the diaper 1 shown in FIG. 5, a wide continuous sheet 122 as an outer sheet precursor and a wide continuous sheet 123 as an inner sheet precursor are bonded to each other and then cut by the cutting means 93 to obtain a continuous front outer cover 102A and a continuous rear outer cover 102B. This may be changed to the manner shown in FIG. 9. That is, a pair of a continuous outer sheet 122A and a facing continuous inner sheet 123A for the formation of a front outer cover 2A and a pair of a continuous outer sheet 122B and a facing continuous inner sheet 123B for the formation of a rear outer cover 2B are separately supplied to the respective joining zones to obtain a continuous front outer cover 102A and a continuous rear outer cover 102B, respectively. In this modification, the outer sheets 122A and 122B may be fed from the respective rolls or may be obtained by cutting an unshown wider outer sheet precursor upstream from FIG. 9. Likewise, the inner sheets 123A and 123B may be fed from the respective rolls or may be obtained by cutting an unshown wider outer sheet precursor upstream.

The extensible sheet used in the disposable pull-on diaper of the third embodiment may be used as an outer sheet and/or an inner sheet to make a laminate as a front outer cover 2A and a rear outer cover 2B.

The side portion 102A' and/or the side portion 102B' of the continuous front outer cover 102A and/or the continuous rear outer cover 102B may be folded over as shown in FIG. 5, or the continuous front outer cover 102A and/or the continuous rear outer cover 102B may be cut into individual front and rear outer cover 2A and 2B without folding.

A disposable pull-on diaper 1A (hereinafter simply referred to as a diaper 1A) according to a sixth embodiment of the invention (an embodiment of the first and second aspect of the invention) will be described by referring to FIGS. 10 through 14. The disposable pull-on diaper 1A of the sixth embodiment has a basic structure shown in FIG. 11, which is the same as that of the diaper 1 of the first embodiment, except that the length of each of the front and the rear outer cover of the absorbent article according to the second aspect of the invention in the diaper longitudinal direction does not need to be uniform in the diaper lateral direction.

Description of the disposable pull-on diaper of the sixth embodiment will generally be confined to the differences from the first embodiment, with the details in common omitted. The description of the first embodiment applies to the sixth embodiment with the exceptions noted hereafter. The elements or members of the sixth embodiment common to the first embodiment are identified with the same reference numerals as in the first embodiment.

Figure 10:
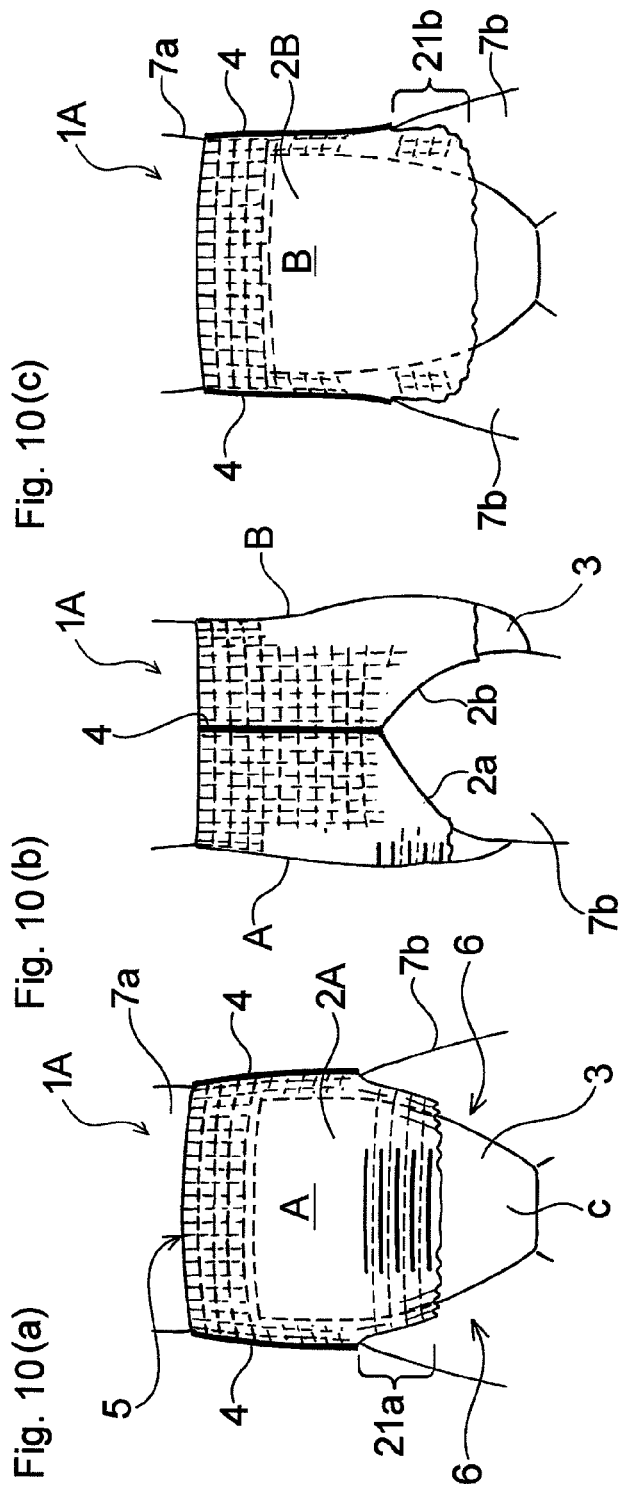
Figure 11:
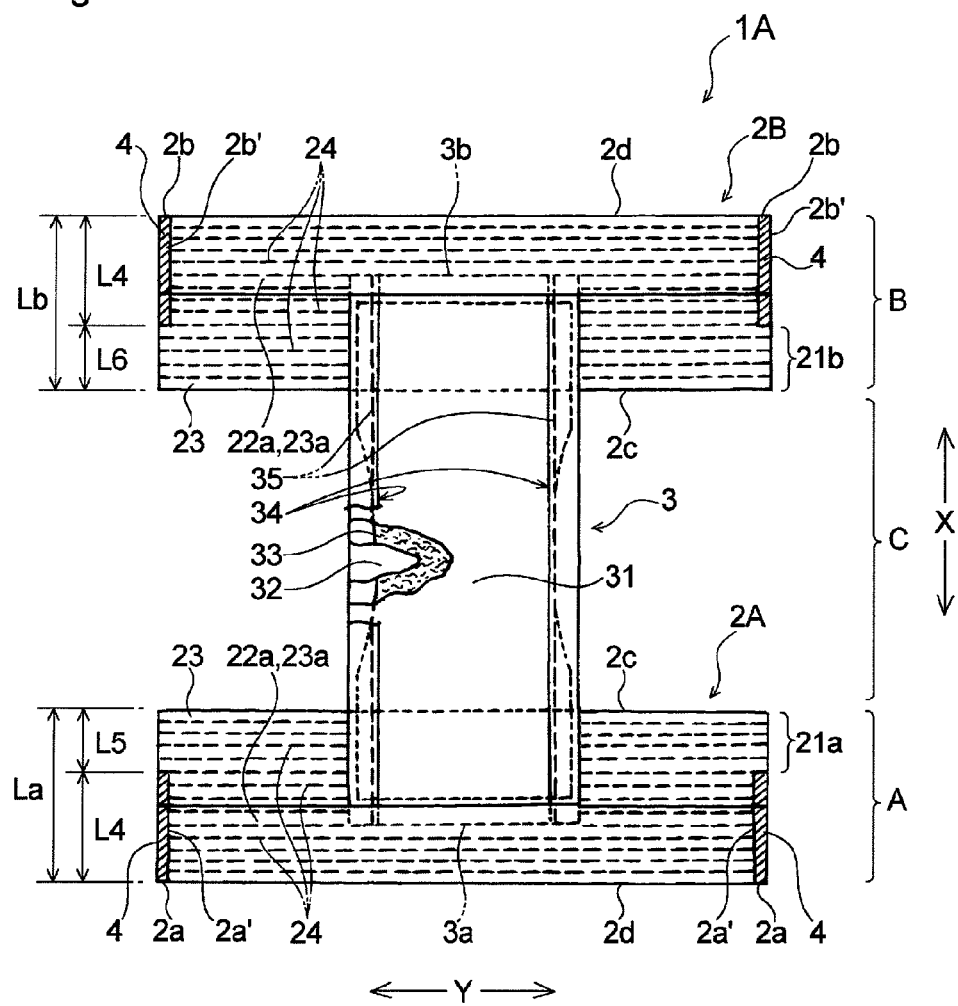
FIG. 11 is a plan of the disposable pull-on diaper shown in FIGS. 10(a) to 10(c) in its flat-out, uncontracted state with a part cut away. As used herein, the term "flat-out, uncontracted state" means a state in which a pull-on absorbent article is opened by tearing the side seals apart and with every elastic member straightened up to its design dimension (the dimension of an article in a flat-out configuration with any influences of elastic members eliminated).

As shown in FIGS. 10 and 11, the diaper 1A of the sixth embodiment includes a front outer cover 2A adapted to be worn around a wearer's front side, a rear outer cover 2B adapted to be worn around the wearer's rear side, and an absorbent assembly fixed to the front outer cover 2A and the rear outer cover 2B so as to bridge them. The diaper 1A has side seals 4 along opposite side edges 2a of the front outer cover 2A and opposite side edges 2b of the rear outer cover 2B where the front outer cover 2A and the rear outer cover 2B are joined. The front and the outer cover 2A and 2B have extension portions 21a and 21b, respectively, each extending downward from the side seals 4. The diaper (absorbent article) 1A has a longitudinal direction (direction X in FIG. 11) extending from the front portion A through the crotch portion C to the rear portion B or vice versa and a lateral direction (direction Y in FIG. 11) perpendicular to the longitudinal direction.

When the front and the rear outer cover 2A and 2B are elasticized by the elastic members 24 disposed between two sheets in their stretched state as with the case of the diaper 1A of the present embodiment, it is preferred for the opposite side edges 2a and 2a and for the opposite side edges 2b and 2b to be parallel with each other with the elastic members 24 in the stretched state as shown in FIG. 11. It is preferred for both the front and the rear outer cover 2A and 2B to be rectangular, longer in the diaper lateral direction, with the elastic members 24 in their stretched state.

The opposite side edges 2a and 2a do not need to be parallel, and so do the opposite side edges 2b and 2b. For example, the distance between the opposite side edges may increase or decrease from one end edge 2d to the other end edge 2c in the front or the rear outer cover 2A or 2B, or may once increase and then decrease or once decrease and then increase in that direction.

Figure 12:
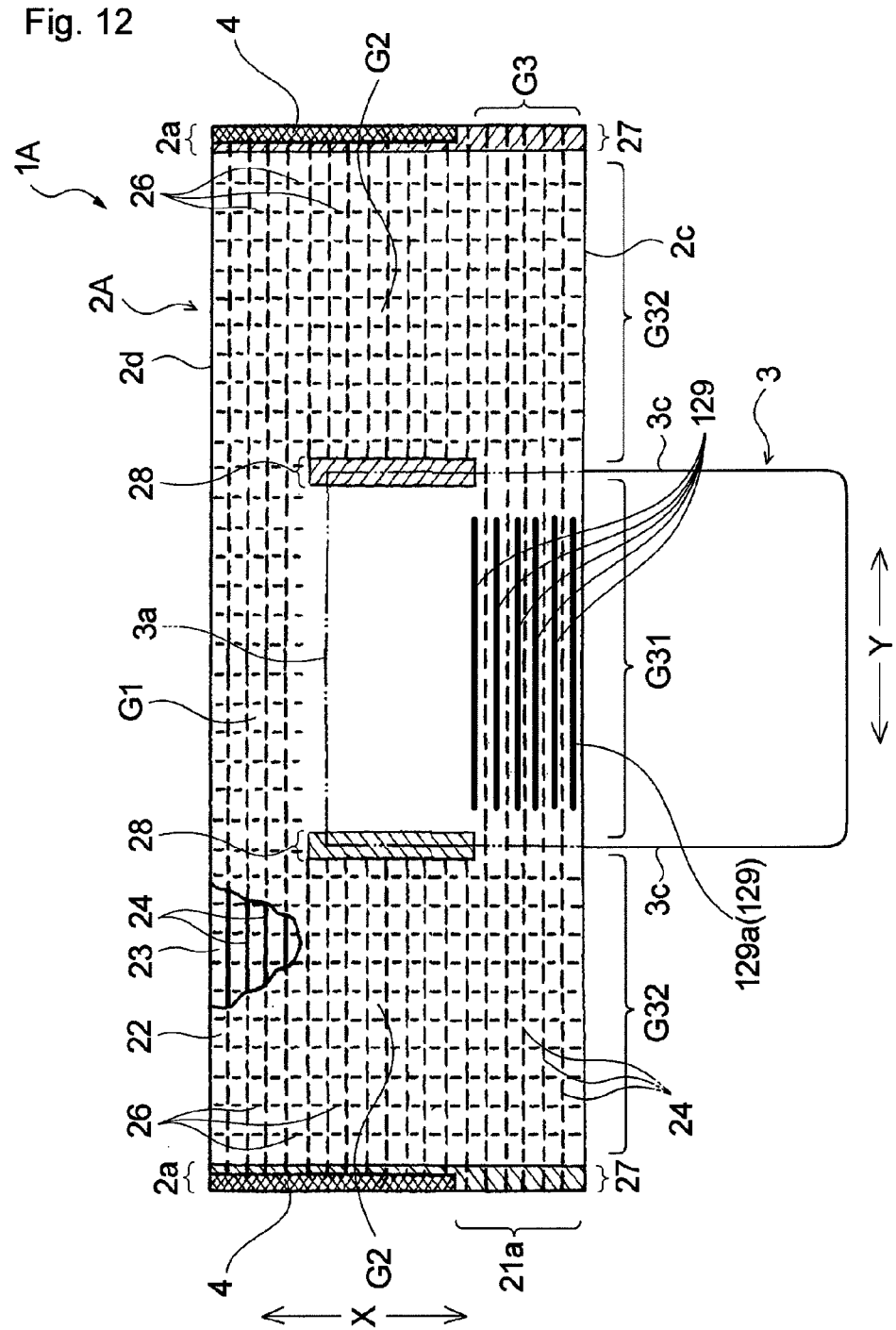
FIG. 12 is an enlarged view of the disposable pull-on diaper shown in FIGS. 10(a) to 10(c) in its uncontracted state, seen from the front, with a part cut away.
Figure 13:
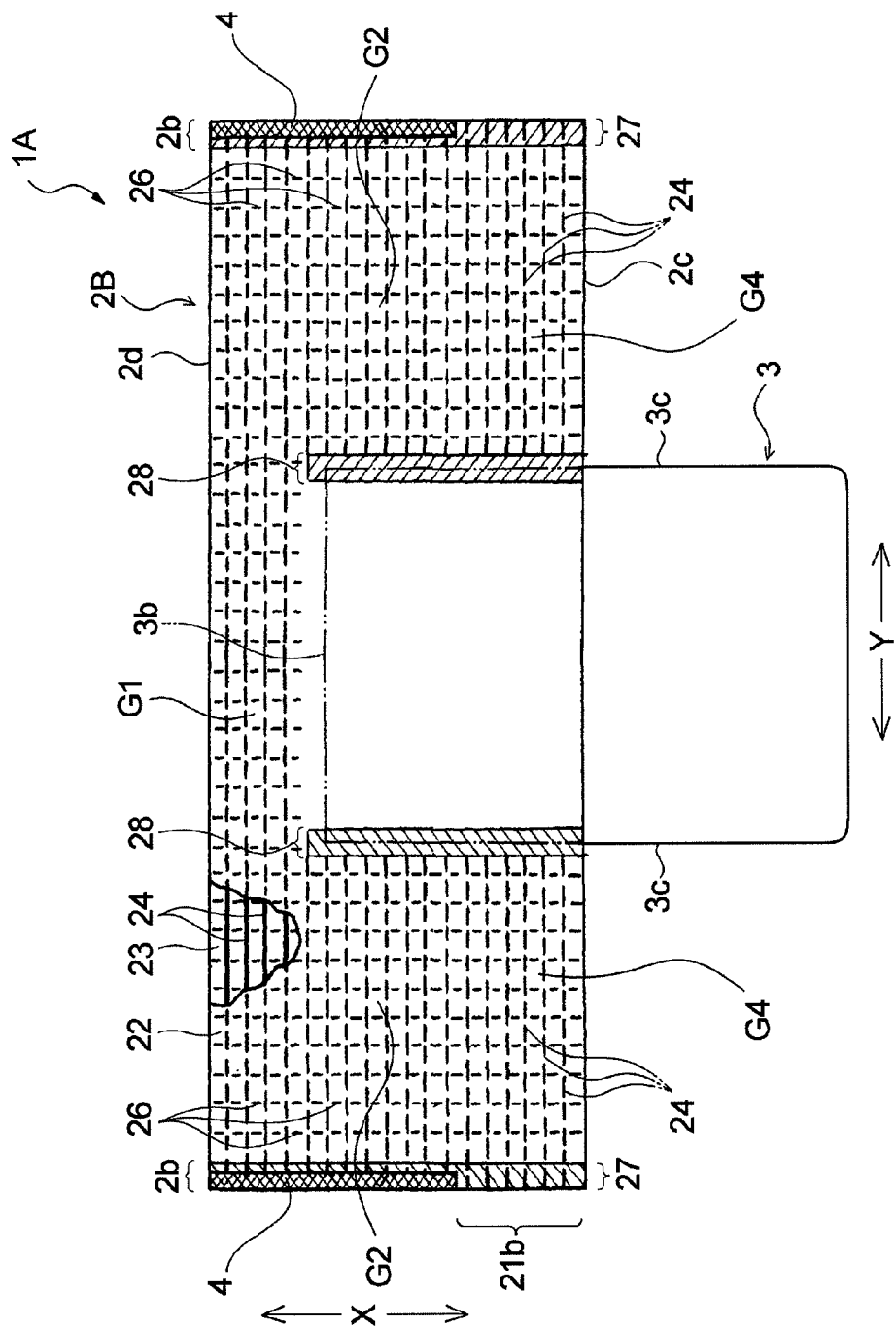
FIG. 13 is an enlarged view of the disposable pull-on diaper shown in FIGS. 10(a) to 10(c) in its uncontracted state, seen from the rear, with a part cut away.
Figure 14:
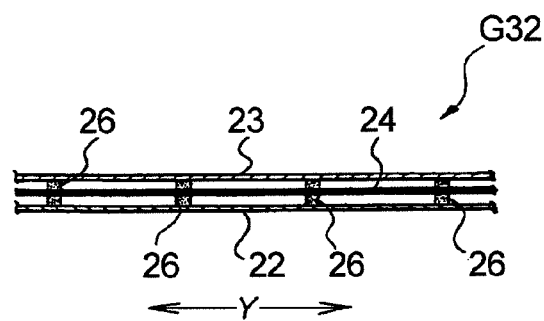
Figure 14:
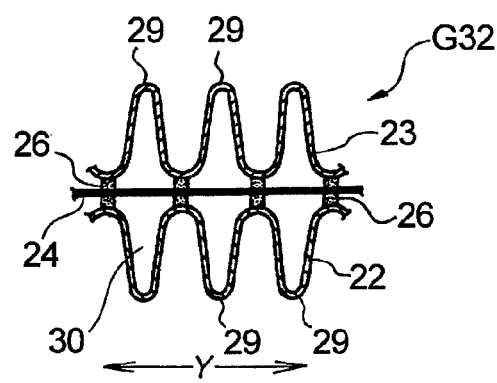

As shown in FIGS. 12 and 13, the front and the rear outer cover 2A and 2B of the diaper 1A each include an outer sheet 22 that defines the exterior of the diaper, an inner sheet 23 laid on the inner side of the outer sheet 22, and a plurality of elastic members 24 of thread form arranged between the two sheets 22 and 23 and have an elasticized waist region G1, an elasticized below-waist region G2, and an elasticized extension region G3 or G4, respectively.

The elasticized waist region G1 is outward from the longitudinal end 3a or 3b of the absorbent assembly 3 in the diaper longitudinal direction (direction X) in each of the front and the rear outer covers 2A and 2B. The elasticized below-waist region G2 is between the elasticized waist region G1 and the extension portion 21a or 21b along direction X in each of the front and the rear outer cover 2A and 2B.

The elasticized extension region G3 is formed in the extension portion 21a of the front outer cover 2A, while the elasticized extension region G4 is formed in the extension portion 21b of the rear outer cover 2B. The elasticized extension region G3 formed in the front outer cover 2A will be referred to as an elasticized front extension region G3, and the elasticized extension region G4 formed in the rear outer cover 2B will be referred to as an elasticized rear extension region G4.

As shown in FIGS. 12 and 13, the elasticized below-waist region G2 and the elasticized rear extension region G4 are divided into two parts, one on each side of the diaper 1A so that the region overlapping the absorbent assembly 3, particularly the region overlapping the lateral middle portion of the absorbent assembly 3 may not be elasticized.

As shown in FIGS. 12 and 13, the elasticized waist region G1 and the elasticized front extension region G3 are formed to exhibit extensibility and contractibility over the entire distance between end fixing parts 27 (hereinafter described) in the front and the rear outer cover 2A and 2B, thereby to have extensibility and contractibility over substantially the whole width (in direction Y) of the diaper 1A.

The outer sheet 22 and the inner sheet 23 are bonded together at a large number of discretely formed bonds 26 in the elasticized waist region G1, the elasticized below-waist region G2, and the elasticized rear extension region G4.

More specifically, bonds 26 are discretely arranged in a row in the diaper lateral direction (direction Y). A plurality of such rows of bonds 26 are arranged in the diaper longitudinal direction (direction X). The positions in direction Y of the bonds of a row coincide with those of the bonds of adjacent rows. That is, the bonds 26 also form lines in the diaper longitudinal direction (direction X). A plurality of such lines of bonds 26 are spacedly arranged in the diaper lateral direction (direction Y).

A plurality of elastic members 24 are arranged to pass between bonds 26 adjacent in the longitudinal direction in each of the elasticized regions G1, G2, and G4. Each elastic member 24 is not fixed to either the outer sheet 22 or the inner sheet 23 at other than the end fixing parts 27 and an absorbent assembly-side end fixing part 28 (hereinafter described).

The elasticized waist region G1 in the front outer cover 2A has, along the lateral side edges 2a and 2a, an opposite pair of end fixing parts 27 in which the outer and the inner sheet 22 and 23 are bonded to each other with an adhesive (see FIG. 12). Each of the elastic members 24 disposed in the elasticized waist region G1 is secured between the sheets 22 and 23 at the opposite pair of the end fixing parts 27, while not being fixed to either the sheet 22 or the sheet 23 between the opposite end fixing parts 27. The same configuration applies to the elasticized waist region G1 in the rear outer cover 2B (see FIG. 13).

The elasticized below-waist region G2 on each side of the front outer cover 2A has an end fixing part 27 along the respective side edge of the front outer cover 2A where the outer sheet 22 and the inner sheet 23 are bonded with an adhesive and an absorbent assembly-side fixing part 28 near the side edge 3c of the absorbent assembly 3 where the outer sheet 22 and the inner sheet 23 are bonded with an adhesive (see FIG. 12). Each of the elastic members 24 disposed in the elasticized below-waist region G2 is secured between the sheets 22 and 23 at the end fixing part 27 and at the absorbent assembly-side fixing part 28, while not being fixed to either the sheet 22 or the sheet 23 between the end fixing part 27 and the absorbent assembly-side fixing part 28. The same configuration applies to the elasticized below-waist region G2 and the elasticized rear extension region G4 in the rear outer cover 2B (see FIG. 13).

The elasticized front extension region G3 of the diaper 1A of the sixth embodiment has end fixing parts 27 along each side edge of the front outer cover 2A where the outer sheet 22 and the inner sheet 23 are bonded with an adhesive. The elasticized front extension region G3 has a plurality of elastic members 24 fixed between the sheets 22 and 23 at the opposing end fixing parts 27 and not fixed to either the sheet 22 or 23 between the opposite end fixing parts 27. The number of the elastic members 24 arranged in the elasticized front extension region G3, which are fixed between the sheets 22 and 23 only at or around their ends located in the end fixing parts 27, is preferably 1 to 30, more preferably about 5 to 15.

The elasticized front extension region G3 includes a middle subregion G31 that overlaps the absorbent assembly 3 and an opposite pair of side subregions G32 located laterally outward of the side edges 3c of the absorbent assembly 3. In FIGS. 12 and 13 are depicted the diaper 1A with the front and the rear outer cover 2A and 2B, respectively, in their stretched state in the diaper lateral direction, i.e., direction Y.

A plurality of linear bonds 129 extending in the diaper lateral direction (direction Y) are formed in the middle subregion G31 of the elasticized front extension region G3 as shown in FIG. 12. The linear bonds 129 are formed by bonding the sheets 22 and 23 by any bonding means, such as heat sealing, ultrasonic sealing, high frequency sealing, adhesive application, or a combination thereof, preferably by heat fusion.

While FIG. 12 illustrates an example in which six linear bonds 129 are formed spacedly in the diaper longitudinal direction, the number of the linear bonds 129 may be one or more than one. In an embodiment having only one linear bond 129, the only one linear bond 129 may be, for example, the linear bond 129a shown in FIG. 12, the closest of the linear bonds 129 to the crotch portion C. The linear bond 129 may be provided at intervals of two or three elastic members 24 or may alternate with the elastic member 24. In the example shown in FIG. 12, the linear bonds 129 alternate with the elastic members 24 in the diaper longitudinal direction such that every elastic member 24 is between vertically adjacent linear bonds 129.

Every elastic member 24 is disposed to avoid an overlap with the linear bonds 129. If the distance between adjacent linear bonds 129 in which an elastic member 24 is disposed is too small relative to the width or thickness of the elastic member 24, the elastic member 24 would be substantially immobilized between the sheets 22 and 23. It is therefore desirable that the linear bonds 129 be spaced from each other at a distance enough to allow the elastic member 24 provided therebetween to slide in direction Y between the sheets 22 and 23.

Each side subregion G32 of the elasticized front extension region G3 has a number of bonds 26 discretely formed in the same manner as in the elasticized waist region G1 and elasticized below-waist region G2 as shown in FIG. 12. More specifically, bonds 26 are discretely arranged in rows extending in the diaper lateral direction (direction Y), which are longitudinally spaced and transversely disposed. An elastic member 24 is disposed between two rows of bonds adjacent in the diaper longitudinal direction.

The bonds 26 in the side subregions G32 of the elasticized front extension region G3 also form a plurality of lines extending in the diaper longitudinal direction (direction X). A plurality of such lines of bonds 26 are spacedly arranged in the diaper lateral direction (direction Y).

On contraction of the elastic members 24, each of the sheets 22 and 23 is deformed to bulge outward to form folds 29 between every pair of adjacent lines of bonds in the elasticized waist region G1, elasticized below-waist region G2, elasticized rear extension region G4, and side subregions G32 of the elasticized front extension region G3. At the same time, vacant spaces 30 are formed between the sheets 22 and 23, being defined by every fold 29 of the sheet 22 and every fold 29 of the sheet 23 (see FIG. 14).

Since the diaper 1A of the present embodiment has the extension portions 21a and 21b in the front and the rear outer cover 2A and 2B, respectively, on putting the diaper 1A on a wearer, the side edge 2a of the extension portion 21a of the front outer cover 2A and the side edge 2b of the extension portion 21b of the rear outer cover 2B on each side of the diaper 1A separate from each other toward the front and the rear in the shape of an inverted letter Y as shown in FIG. 10(b).

Furthermore, the elasticized front extension region G3 of the front outer cover 2A has a plurality of elastic members 24 non-fixed to either the sheet 22 or 23 over the entire distance between the opposite end fixing parts 27. Compared with the arrangement of elastic members 24 in only the regions outboard of the side edges of the absorbent assembly 3 or the arrangement of the elastic members 24 being fixed to the sheets 22 and 23 at the absorbent assembly-side fixing part 28, the arrangement according to the present embodiment allows the amount of contraction (reduction in length) of the elastic members 24 resulting from the contraction over substantially the entire length of the elastic members 24 to act effectively on the portions laterally outward of the opposite ends of the linear bond 129, particularly the portions located laterally outward of both side edges of the absorbent assembly 3.

Thus, the portions of the extension portion 21a of the front outer cover 2A that are laterally outward of both ends of the linear bond 129, particularly the portions located laterally outward of both side edges of the absorbent assembly 3, contracts effectively in the diaper lateral direction.

As a result, the extension portion 21a does not assume a poor appearance like loincloth when seen from the side of the front portion A without turning outward or fluttering. So, it presents a good appearance while worn and is less likely to cause the feeling of insecurity about leakage.

Because the extension portion 21a may be made to contract effectively even in using elastic members having a small extension stress, it is possible to make the extension portion 21a contract efficiently while suppressing the contraction of the absorbent assembly 3 as well as the absorbent core 33 in its lateral direction by employing elastic members having a small extension stress.

Since, in the diaper 1A of the present embodiment, the elasticized front extension region G3 contains the linear bond 129 in its middle subregion G31, the outer sheet 22 is prevented from lifting (bulging away from the inner sheet 23) by the linear bond 129 on contraction of the elastic members 24. As a result, deterioration of the appearance or break of the outer sheet 22 due to the lifting is prevented. In the cases where the outer cover side of the absorbent assembly 3 is decorated with a picture of a character, a pattern, and so on, the decoration would be prevented from becoming less visible due to such lifting.

To prevent lifting or break of the outer sheet 22, it is preferred for at least one, preferably all, of the linear bonds 129 to have a length of at least 1 mm, preferably 10 mm or more. It is also preferred for at least one, preferably all, of the linear bonds 129 to have a length of 5% to 150%, preferably 10% to 100%, relative to the width of the absorbent assembly 3 (in the diaper lateral direction). The width of the linear bond 129 (in the diaper longitudinal direction) is preferably 0.5 to 10 mm, more preferably 1 to 5 mm.

While the linear bond 129 is continuous in the present embodiment, it may be a dotted line. In the case of a dotted line, the term "length of the linear bond 129" in the diaper lateral direction is meant to include the lengths of unbonded regions between adjacent bonded regions, i.e., the term means the total length between the opposite ends of the linear bond 129 in the diaper lateral direction.

The middle subregion G31 of the elasticized front extension region G3 of the diaper 1A is entirely bonded on the side of its inner sheet 23 to the absorbent assembly 3 with an adhesive. The inner sheet 23 and the outer sheet 22 are not bonded together in the middle subregion G31 of the extension portion 21a except at the linear bond 129.

Furthermore, in the diaper 1A of the present embodiment, since the extension portions 21a and 21b of the front and the rear outer cover 2A and 2B have the elasticized extension regions G3 and G4, respectively, the extension portions 21a and 21b are elasticized in the diaper lateral direction so that the edges of the extension portions 21a and 21b softly apply to the upper part of the leg 7b. As a result, the diaper 1A is effectively prevented from sliding down.

While the diaper is worn, the extension and contraction stress of the elasticized extension regions G3 and G4 functions to enhance the body constrictive, extension and contraction stress of the elasticized waist region G1 and the elasticized below-waist region G2 to thereby provide a better body fit.

The diaper 1A is thus successfully prevented from sliding down without excessively increasing the constrictive force around the waist opening 5 and the leg openings 6. The extension portion 21b of the rear outer cover 2B provides moderate coverage over the wearer's buttocks, which prevents such a poor appearance as might be caused by the protrusion of the wearer's buttocks.

The presence of the extension portions 21a and 21b in the front outer cover 2A and the rear outer cover 2B helps the side seals 4 to maintain relative straightness, as shown FIG. 10(b), thereby to impart well-balanced and uniform constrictive force to the front and the rear portion A and B of the diaper 1A.

The diaper 1A exhibits elastic extensibility in not only the extension portion 21a of the front outer cover 2A but also the elasticized rear extension region G4 in the rear outer cover 2B. This configuration brings about further improved effect on prevention of sliding down.

The elasticized front extension region G3 and the elasticized rear extension region G4 being different in structure as described, the contractibility of the regions outboard of each side edge of the absorbent assembly 3 may be varied between the extension portion 21a of the front outer cover 2A and the extension portion 21b of the rear outer cover 2B even when the extension portions 21a and 21b are formed by using elastic members of the same extension stress at the same stretch ratio.

The extension portion 21a of the front outer cover 2A has higher extensibility than the extension portion 21b of the rear outer cover 2B by virtue of the presence of the linear bonds 129 and the elastic members' not being fixed at other than the end fixing parts 27 and 27.

The extensibility of the extension portions 21a and 21b in the diaper lateral direction is preferably such that the length, in the diaper lateral direction, of the portion laterally outward of the side edge 3c of the absorbent assembly 3 in each of the extension portions 21a and 21b with the diaper 1A in a contracted state is 15% to 90%, more preferably 20% to 60%, even more preferably 25% to 50%, relative to the length of the same portion with the diaper 1A in a flat-out, uncontracted state.

To further ensure one or more of the aforementioned effects, it is preferred that the extension length L5 of the extension portion 21a and the extension length L6 of the extension portion 21b of the front and the rear outer cover 2A and 2B, respectively, be in the range of from 5% to 150%, more preferably 25% to 70%, of the length L4 of the side seal 4.

For the same purpose, it is preferred that the length L5 of the extension portion 21a in the front outer cover 2A be in the range of from 5% to 60%, more preferably 20% to 40%, of the length La of the front outer cover 2A and that the length L6 of the extension portion 21b in the rear outer cover 2B be in the range of from 5% to 60%, more preferably 20% to 40%, of the length Lb of the rear outer cover 2B.

Preferred ranges of the extension lengths L5 and L6 of the extension portions 21a and 21b and the reasons for the preference are the same as in the first embodiment.

A preferred method for making the disposable pull-on diaper 1A of the sixth embodiment will then be described with reference to FIG. 15. In carrying out the method, the undescribed details are the same as those described with respect to the production of the diaper according to the first embodiment by way of FIG. 5.

Figure 15:
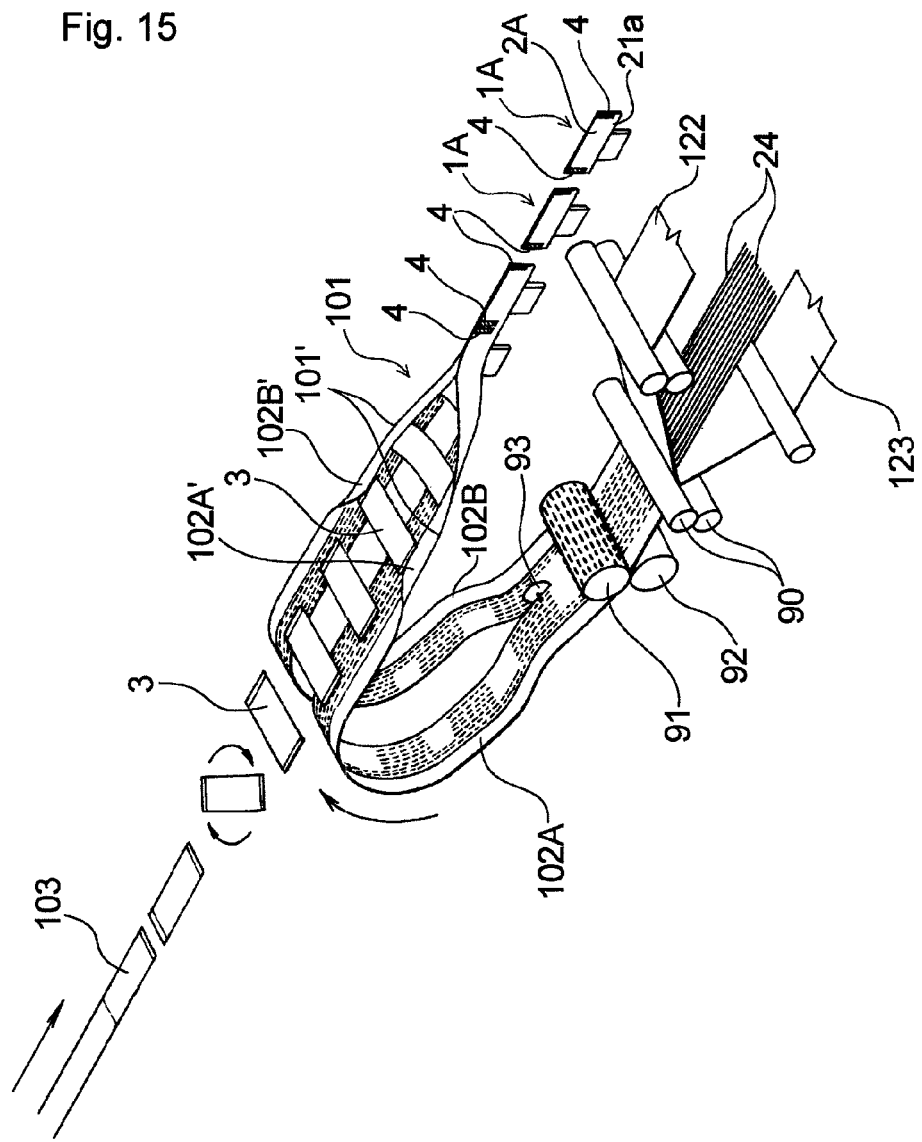
FIG. 15 illustrates a preferred method of making the disposable pull-on diaper shown in FIGS. 10(a) to 10(c).

As shown in FIG. 15, a wide continuous sheet 122 as an outer sheet precursor and a wide continuous sheet 123 as an inner sheet precursor are superposed on each other with the elastic members 24 inserted therebetween in their stretched state. Before the continuous sheets 122 and 123 are superposed, an adhesive for the formation of end fixing parts 27 and absorbent assembly-side fixing parts 28 is intermittently applied to the continuous sheet 122 and/or the continuous sheet 123 by means of an unshown adhesive applicator. The two continuous sheets are pressed between a pair of nip rollers 90 to fix the elastic members 24 between the continuous sheets 122 and 123 at the fixing parts 27 and 28.

The superposed continuous sheets 122 and 123 are then introduced between a pressure roller 91 and a facing anvil roller 92 to be pressed in parts with heat. The pressure roller 91 has, on its peripheral surface, projections for forming bonds 26, projections for forming linear bonds 129, and projections for cutting the elastic members 24. As a result, a large number of bonds 26 and linear bonds 129 are formed, and, at the same time, the elastic members 24 are cut to provide a region where an absorbent assembly 3 is to be disposed. The formation of the bonds 26, formation of the linear bonds 129, and cutting of the elastic members 24 may separately be performed using respective pressure rollers. Otherwise, the formation of the bonds 26 and the cutting of the elastic members 24 may be achieved by the same pressure roller, while the formation of the linear bonds 129 may be effected using another pressure roller.

The laminate of the continuous sheets 122 and 123 with the elastic members 24 therebetween is then cut by a cutting unit 93 into two continuous sheets: 102A and 102B. The operations thereafter are the same as those in the method of producing the diaper of the first embodiment described with reference to FIG. 5.

Thus, the diaper 1A of the sixth embodiment can be produced without trimming the outer cover-forming continuous sheets 112 and 123 to form the leg openings. Therefore, the steps associated with removal and recycling of trimmings are unnecessary, and the diaper 1A can be produced efficiently and economically. To produce no trimmings is environmentally friendly.

A seventh and an eighth embodiment of the invention will then be described.

Description of the disposable pull-on diapers of the seventh and the eighth embodiment will generally be confined to the differences from the sixth embodiment, with the details in common omitted. The description of the first and/or the sixth embodiment applies to the seventh and the eighth embodiment with the exceptions noted hereafter. The elements or members of the seventh and the eighth embodiment common to the first and/or the sixth embodiment are identified with the same reference numerals as in the first and the sixth embodiment.

Figure 16:
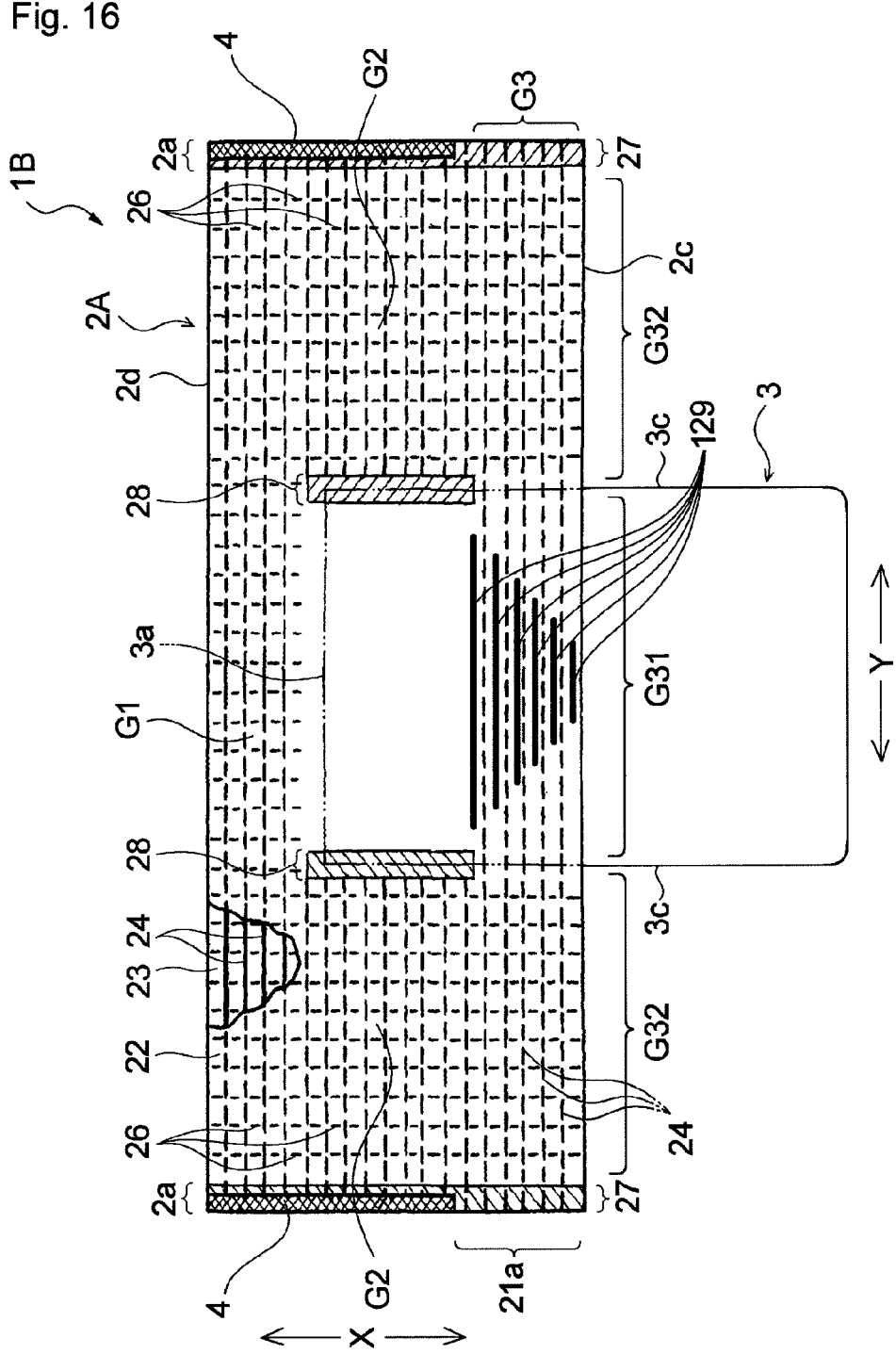
FIG. 16 shows a disposable pull-on diaper according to another embodiment of the invention (equivalent to FIG. 12).

As shown in FIG. 16, a disposable pull-on diaper 1B of the seventh embodiment has a plurality of linear bonds 129 in the middle subregion G31 of the elasticized front extension region G3. The length of the linear bonds 129 gradually decreases from the side of the waist opening 5 toward the crotch portion C.

The contracted region in each side of the extension region 21a spans the length up to the respective ends of the linear bonds 129. The extent of the contracted region getting laterally inward increases from the side of the waist opening 5 toward the crotch portion C. The side edges of the extension region 21a are therefore pulled laterally inward more largely with increasing distance from the waist opening 5 toward the crotch portion C.

As a result, the parts of the front portion A around the wearer's legs look like a high-cut leg garment.

The disposable pull-on diaper of the eighth embodiment has an elasticized region having the same structure as the elasticized front extension region G3 of the diaper 1A according to the sixth embodiment in not only the extension portion 21a of the front outer cover 2A but the extension portion 21b of the rear outer cover 2B.

While the first and the second aspect of the invention have been described with respect to their preferred sixth to eighth embodiments, the sixth to eighth embodiments described are subject to appropriate modifications and alterations, for example, as follows.

The bonds 26 in the side subregions G32 of the elasticized front extension region G3 may be arranged in a staggered pattern in a plan view. The elasticized waist region G1, the elasticized below-waist region G2, and the like may be formed of a laminate composed of two sheets entirely bonded to each other with elastic members fixed therebetween. The extension region of the rear outer cover 2B may have extensibility in the diaper lateral direction based on a different structure from that of the diaper 1A of the sixth embodiment. As used herein, the phrase "to have extensibility in the diaper lateral direction" is intended to mean that the region may have extensibility only in the lateral direction (direction Y), in both the lateral direction (direction Y) and the longitudinal direction (direction X), or in any planar direction. A disposable pull-on diaper 1D according to a ninth embodiment of the invention (an embodiment of the third aspect of the invention) (hereinafter also referred simply to "diaper 1D") will be described with reference to FIGS. 17 through 21. The basic structure of the disposable pull-on diaper 1D of the ninth embodiment is illustrated in FIG. 18, which is the same as that of the diaper 1 of the first embodiment, except that the front outer cover and/or the rear outer cover used in the third aspect of the invention do/does not always need to have an extension region and that the length of each of the front and the rear outer cover in the diaper longitudinal direction does not need to be uniform in the diaper lateral direction.

Description of the disposable pull-on diaper 1D of the ninth embodiment will generally be confined to the differences from the first embodiment, with the details in common omitted. The description of the first embodiment applies to the ninth embodiment with the exceptions noted hereafter. The elements or members of the ninth embodiment common to the first embodiment are identified with the same reference numerals as in the first embodiment.

Figure 18:
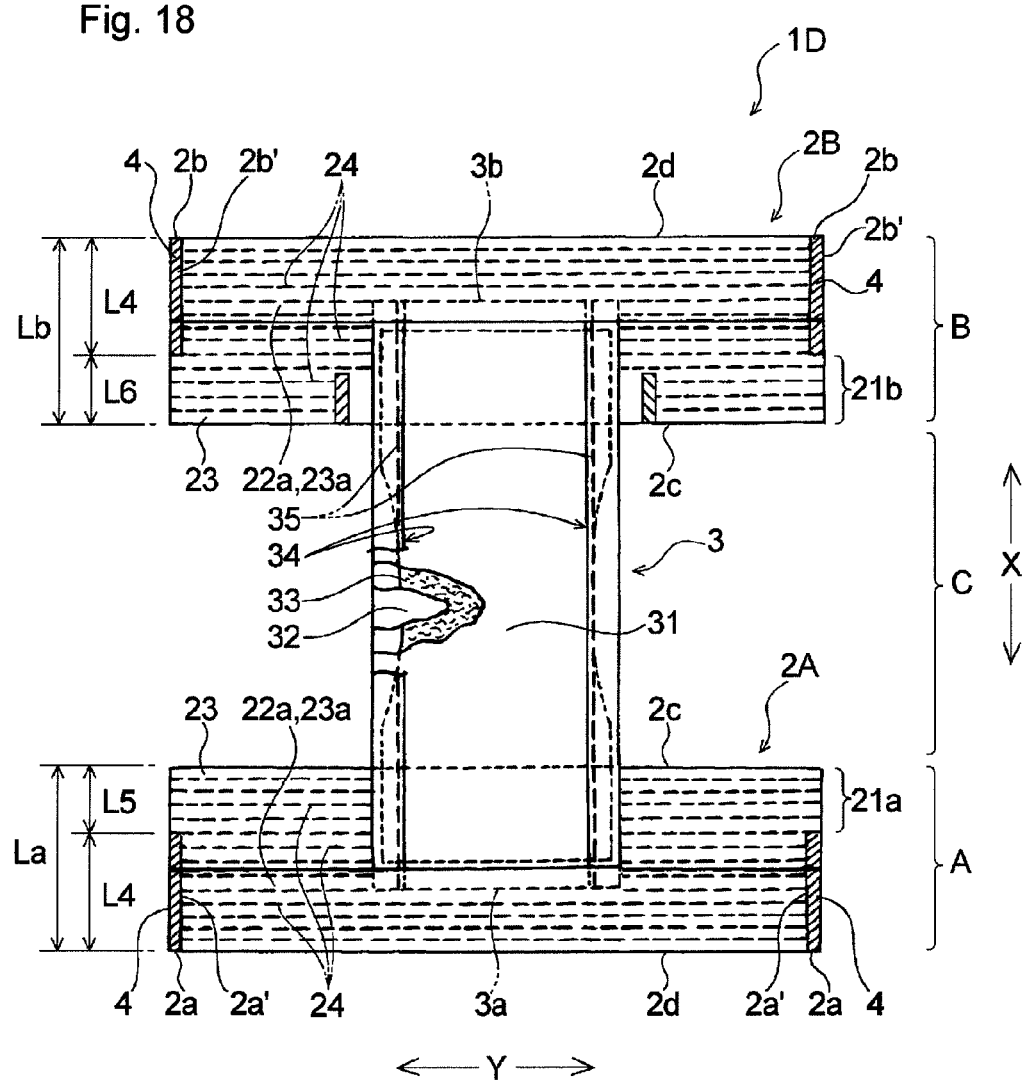
FIG. 18 is a schematic plan of the disposable pull-on diaper shown in FIGS. 17(a) to 17(c) in its flat-out, uncontracted state with a part cut away. As used herein, the term "flat-out, uncontracted state" means a state in which a pull-on absorbent article is opened by tearing the side seals apart and with every elastic member straightened up to its design dimension (the dimension of an article in a flat-out configuration with any influences of elastic members eliminated).

As shown in FIG. 18, the diaper 1D according to the ninth embodiment includes a front outer cover 2A adapted to be worn around the wearer's front, a rear outer cover 2B adapted to be worn around the wearer's rear, and an absorbent assembly 3 fixed to the front outer cover 2A and the rear outer cover 2B so as to bridge them. The diaper 1D is of pull-on type having the front outer cover 2A and the rear outer cover 2B connected to each other to make a loop.

The diaper 1D has a pair of opposite side seals 4 along the lateral side edges 2a and 2b of the front and the rear outer cover 2A and 2B formed by joining the front and the rear outer cover 2A and 2B.

As shown in FIG. 18, the front outer cover 2A has a length La greater than the length L4 of the side seals in the longitudinal direction of the absorbent article. That is, the front outer cover 2A has an extension portion 21a extending downward from the side seals 4. Similarly, the rear outer cover 2B has a length Lb greater than the length L4 of the side seals in the longitudinal direction of the absorbent article. That is, the rear outer cover 2B has an extension portion 21b extending downward from the side seals 4.

The diaper (absorbent article) 1D has a longitudinal direction (direction X in FIG. 18) extending from the front portion A through the crotch portion C to the rear portion B or vice versa and a lateral direction (direction Y in FIG. 18 perpendicular to the longitudinal direction.

It is preferred for the opposite side edges 2a and 2a and for the opposite side edges 2b and 2b to be parallel with each other with the elastic members 24 in the stretched state as shown in FIG. 18. It is preferred for both the front and the rear outer cover 2A and 2B to be rectangular, longer in the diaper lateral direction, with the elastic members 24 in their stretched state.

The opposite side edges 2b and 2b do not need to be parallel. For example, the distance between the opposite side edges may increase or decrease from one end edge 2d to the other end edge 2c in the front or the rear outer cover 2A or 2B, or may once increase and then decrease or once decrease and then increase in that direction.

As shown in FIG. 18, the length of the side seals 4 is smaller than either the length La of the front outer cover 2A or the length Lb of the rear outer cover 2B. That is, the front and the rear outer cover 2A and 2B have a front extension region 21a and a rear extension region 21b, respectively, both extending downward (vertically downward while worn) from the side seals 4.

Figure 19:
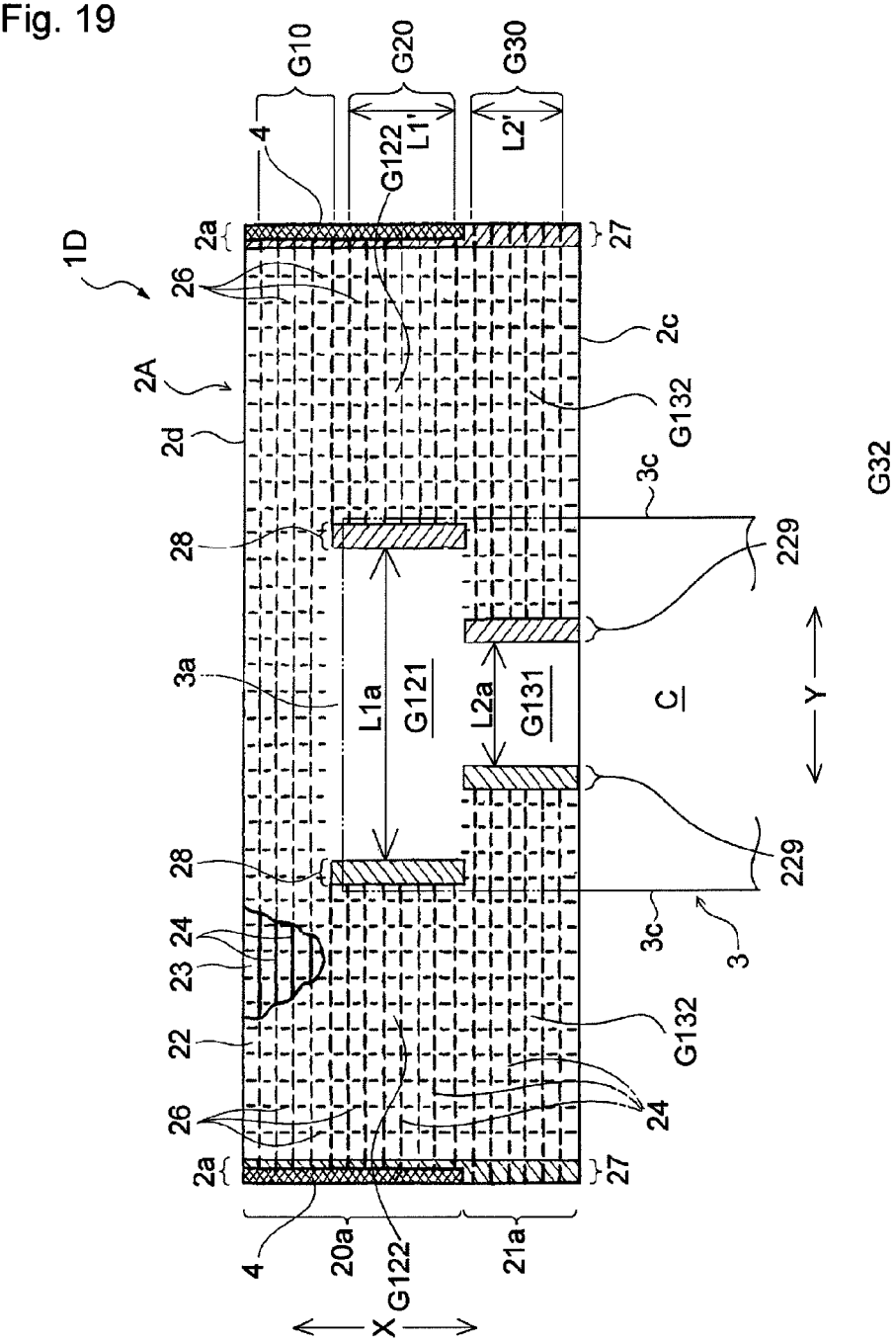
FIG. 19 is an enlarged view of the disposable pull-on diaper shown in FIGS. 17(a) to 17(c) in its uncontracted state, seen from the front, with a part cut away.
Figure 20:
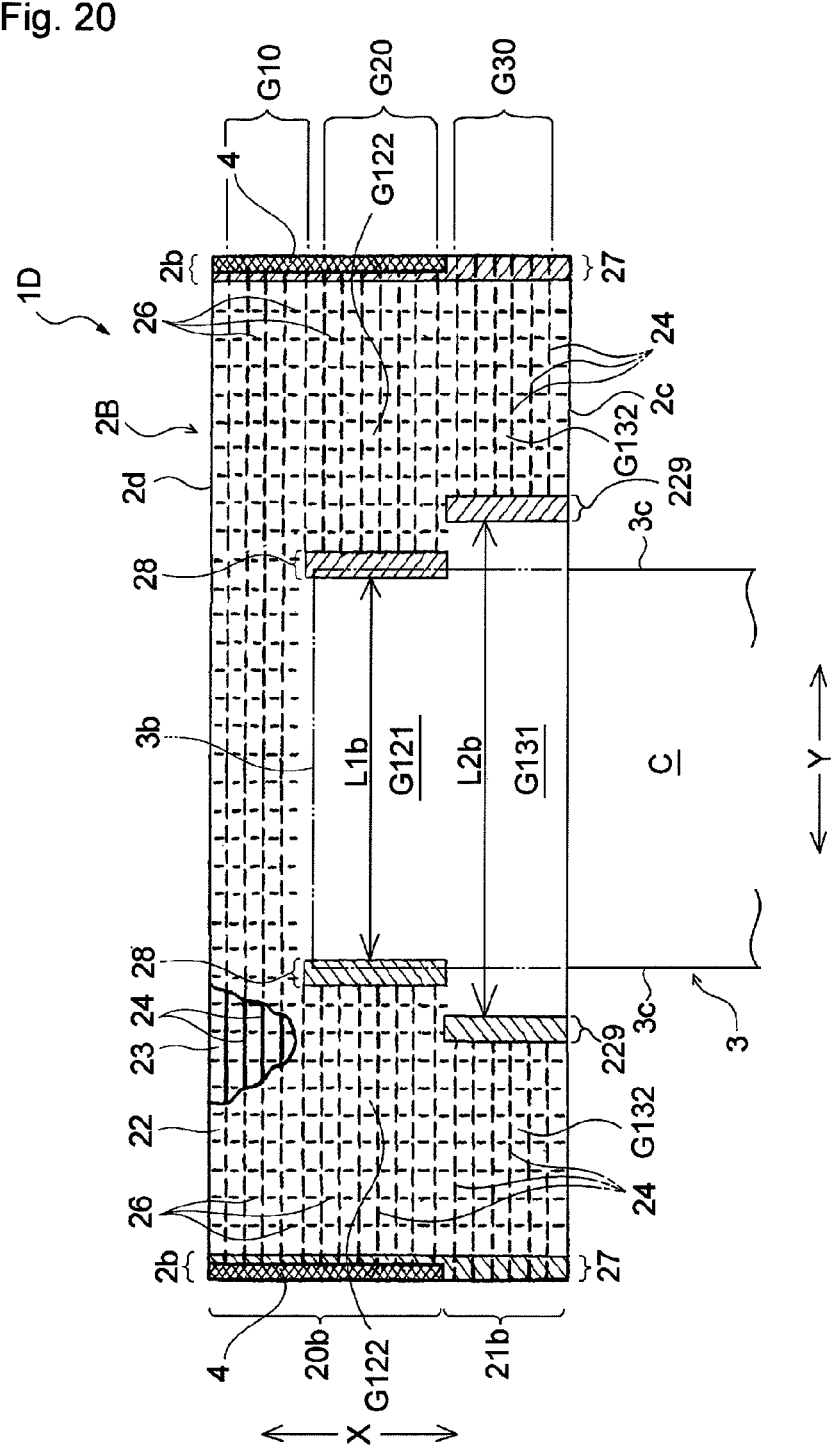
FIG. 20 is an enlarged view of the disposable pull-on diaper shown in FIGS. 17(a) to 17(c) in its uncontracted state, seen from the rear, with a part cut away.

Each of the front and the rear outer cover 2A and 2B of the diaper 1D includes, as shown in FIGS. 19 and 20, an outer sheet 22 defining the exterior of the diaper, an inner sheet 23 laid on the inner side of the outer sheet 22, and a plurality of elastic members 24 of thread form disposed in their stretched state between the two sheets 22 and 23 to extend in the diaper lateral direction (direction Y). Each of the front and the rear outer cover 2A and 2B has an elasticized waist region G10, a first elasticized region G20, and a second elasticized region G30.

The elasticized waist region G10 in each of the front and the rear outer cover 2A and 2B is located outward from the respective longitudinal end 3a or 3b of the absorbent assembly 3 in the diaper longitudinal direction (direction X), namely closer to the waist opening edge than the end 3a or 3b of the absorbent assembly 3. Both the first elasticized region G20 and the second elasticized region G30 are located closer to the crotch portion C than the end 3a or 3b of the absorbent assembly 3 in the diaper longitudinal direction (direction X). The second elasticized region G30 is closer to the crotch portion C than the first elasticized region G20.

All the elasticized waist region G10, first elasticized region G20, and second elasticized region G30 are extensible and contractible in the diaper lateral direction (direction Y) by the action of the elastic members 24.

The front outer cover 2A has a pair of end fixing parts 27 along the opposite side edges 2a and 2a extending in the diaper longitudinal direction (direction X), where the outer and the inner sheet 22 and 23 are bonded to each other (see FIG. 19). Likewise, the rear outer cover 2B has a pair of end fixing parts 27 along the opposite side edges 2b and 2b extending in the diaper longitudinal direction (direction X), where the outer and the inner sheet 22 and 23 are bonded to each other with an adhesive (see FIG. 20).

As shown in FIGS. 19 and 20, each of the front and the rear outer cover 2A and 2B has, between the end fixing parts 27, a pair of first assembly-side fixing parts 28 and a pair of second assembly-side fixing parts 229, in both of which the outer and the inner sheet 22 and 23 are bonded to each other with an adhesive. The first assembly-side fixing parts 28 and 28 are formed generally in the first elasticized region G20. The second assembly-side fixing parts 229 and 229 are formed generally in the second elasticized region G30. All the first and the second assembly-side fixing parts 28 and 229 are closer to the absorbent assembly 3 (the center of the absorbent assembly 3 in direction Y) than the end fixing parts 27 in the diaper lateral direction.

As shown in FIGS. 19 and 20, the elasticized waist region G10 in each of the front and the rear outer cover 2A and 2B is configured to show extensibility over the whole length between the opposite end fixing parts 27 and 27. The elasticized waist region G10 has a plurality of elastic members 24 continuously extending between the opposite end fixing parts 27 and 27. The elasticized waist region G10 may include, in addition to the elastic members 24 continuous over the length between the opposite end fixing parts 27 and 27, an elastic member that is cut at a position between the opposite assembly-side fixing parts 28 and 28 and thereby separated into right and left sides.

The first elasticized region G20 in each of the front and the rear outer cover 2A and 2B is composed of a pair of elasticized subregions G122 and G122 each extensible in the lateral direction of the diaper 1D between the end fixing part 27 on the right or left side of FIGS. 19 and 20 and the first assembly-side fixing part 28. There is created a non-elasticized subregion G121 between the first assembly-side fixing parts 28 by cutting the elastic members 24.

Likewise, the second elasticized region G30 in each of the front and the rear outer cover 2A and 2B is composed of a pair of elasticized subregions G132 and G132 each extensible in the diaper lateral direction between the end fixing part 27 on the right or left side of FIGS. 19 and 20 and the second assembly-side fixing part 229. There is created a non-elasticized subregion G131 between the second assembly-side fixing parts 229 by cutting the elastic members 24.

As shown in FIGS. 19 and 20, the outer sheet 22 and the inner sheet 23 are bonded at a number of discretely arranged bonds 26 in each of the elasticized waist region G10, the elasticized subregions G122 and G122 of the first elasticized region G20, and the elasticized subregions G132 and G132 of the second elasticized region G30. More specifically, bonds 26 are discretely arranged in a row in the diaper lateral direction (direction Y). A plurality of such rows of bonds 26 are spacedly arranged in the diaper longitudinal direction (direction X). The positions in direction Y of the bonds of a row coincide with those of the bonds of adjacent rows. That is, the bonds 26 also form a line in the diaper longitudinal direction (direction X), and a plurality of such lines of bonds 26 are spacedly arranged in the diaper lateral direction (direction Y).

A plurality of elastic members 24 are disposed to pass between bonds 26 adjacent in the longitudinal direction in each of the elasticized waist region G10 and the elasticized subregions G122, G122, G132, and G132. The elastic members 24 disposed in the elasticized waist region G10 and the elasticized subregions G122, G122, G132, and G132 are not fixed to either the sheet 22 or sheet 23 at other than the end fixing parts 27 and the first and the second absorbent assembly-side end fixing parts 28 and 229.

On contraction of the elastic members 24 in the elasticized waist region G10, the elasticized subregions G122 and G122, and the elasticized subregions G132 and G132, each of the sheets 22 and 23 is deformed to bulge outward to form folds 29 between every pair of adjacent lines of bonds. At the same time, vacant spaces 30 are formed between the sheets 22 and 23, being defined by every fold 29 of the sheet 22 and every fold 29 of the sheet 23 (see FIG. 21).

The elastic members 24 disposed in the elasticized subregions G122 and G122 and the elasticized subregions G132 and G132 also exist within the non-elasticized regions G121 and G131 beyond the position of the first or the second assembly-side fixing parts 28 or 229. In the present embodiment, the first and the second assembly-side fixing parts 28 and 229 where the elastic members 24 are secured in their stretched state belong to the elasticized subregions G122 and the elasticized subregions G132, respectively.

The elastic members existing in the non-elasticized subregions G121 and G131 are each disconnected at at least one, preferably two or more positions, between the first assembly-side fixing parts 28 and 28 and between the second assembly-side fixing parts 229 and 229, respectively, to deprive the subregions G121 and G131 of elastic contractibility. The elastic members in the non-elasticized subregions G121 and G131 may be bonded to the sheet 22 and/or the sheet 23 in their unstretched, relaxed state. For example, a segment(s) resulting from cutting an elastic member at two or more positions may be weakly bonded to the sheet 22 and/or 23 in its contracted state.

It is preferred that the unshown elastic members in each of the non-elasticized subregions G121 and G131 be cut at a number of positions discretely distributed in both the longitudinal (direction X) and the lateral direction (direction Y) of the diaper 1D by pressing and/or heating. Thus, the unshown cutting points where the elastic members have been cut leave their marks in a finished diaper 1D (pull-on absorbent article) as fusion bonds of constituent fibers, pressed and densified parts, tiny cuts, and the like, of the sheet 22 and/or 23.

In the diaper 1D of the ninth embodiment, as shown in FIGS. 19 and 20, the first elasticized region G20 in the front and the rear outer cover 2A and 2B is formed in the front outer cover main portion 20a and the rear outer cover main portion 20b, each located between the opposite pair of side seals 4 and 4; and the second elasticized region G30 in the front and the rear outer cover 2A and 2B is formed in the front extension portion 21a and the rear extension portion 21b, each extending downward from the side seals 4 ad 4.

In the diaper 1D of the ninth embodiment, as shown in FIG. 19, the non-elasticized subregion G121 of the first elasticized region G20 and the non-elasticized subregion G131 of the second elasticized region G30 in the front outer cover 2A have different lengths (L1a and L2a) in the diaper (absorbent article) lateral direction (direction Y). The non-elasticized subregion G121 of the first elasticized region G20 and the non-elasticized subregion G131 of the second elasticized region G30 in the rear outer cover 2B have different lengths (L1b and L2b) in the diaper (absorbent article) lateral direction (direction Y).

It is easy to desirably control the contractibility of the first elasticized region G20 and that of the second elasticized region G30 or the relation of contractibility between the first and the second elasticized region G20 and G30 in the front and/or the rear outer cover 2A and/or 2B by adjusting the difference between the lengths L1a and L2a in the front outer cover 2A and/or the difference between the length L1b and L2b in the rear outer cover 2B.

Therefore, the contractibility of the first elasticized region G20 and that of the second elasticized region G30 or the relation of contractibility between the first and the second elasticized region G20 and G30 may be adjusted so as to provide an optimal fit near the crotch portion in accordance with, for example, the weight-, age- (children or adults), or sex-specific differences in body shape. Likewise, the contractibility of the first elasticized region G20 and that of the second elasticized region G30 or the relation of contractibility between the first and the second elasticized region G20 and G30 may be adjusted so as to provide a diaper with a best appearance. Such diaper designing depending on the weight-, age- (children or adults), or sex-specific differences in body shape will be implemented even by disposing elastic members of the same kind in material, thickness, and so on at the same stretch ratio between the two sheets 22 and 23 as well as by changing the material, thickness, and so on between the elastic members for use in the first elasticized region G20 and those for use in the second elasticized region G30.

In the diaper 1D of the ninth embodiment shown in FIG. 20, the second elasticized region G30 is formed in the rear extension portion 21b in the rear outer cover 2B, of which the non-elasticized subregion G131 has a larger length (L2b) than the non-elasticized subregion G121, which has a length L1b, of the first elasticized region G20 in the diaper lateral direction. As a result, the first elasticized region G20 provides a good fit on contracting in direction Y to prevent the diaper 1D from sliding down, while the second elasticized region G30 prevents the rear extension portion 21b from excessively contracting in direction Y whereby the rear extension portion 21 is prevented from turning outward and provides sufficient coverage over the wearer's buttocks.

In the diaper 1D of the ninth embodiment, the length L2b is preferably 105% to 200%, more preferably 110% to 150%, of the length L1b. In the particular example shown in FIG. 20, the length L1b is substantially the same as the width of the absorbent assembly 3, and the length L2b is greater than the width of the absorbent assembly 3. When the length L2b is greater than the width of the absorbent assembly 3, contraction of the absorbent member in direction Y is prevented more effectively to ensure coverage over the buttock side crotch and thereby provide a good protection against urine leakage during sleep.

In the diaper 1D of the ninth embodiment, as shown in FIG. 19, the second elasticized region G30 is formed in the front extension portion 21a of the front outer cover 2A, of which the non-elasticized subregion G131 of the second elasticized region G30 has a smaller length (L2a) than the non-elasticized subregion G121, which has a length L1a, of the first elasticized region G20 in the diaper lateral direction.

Figure 17:
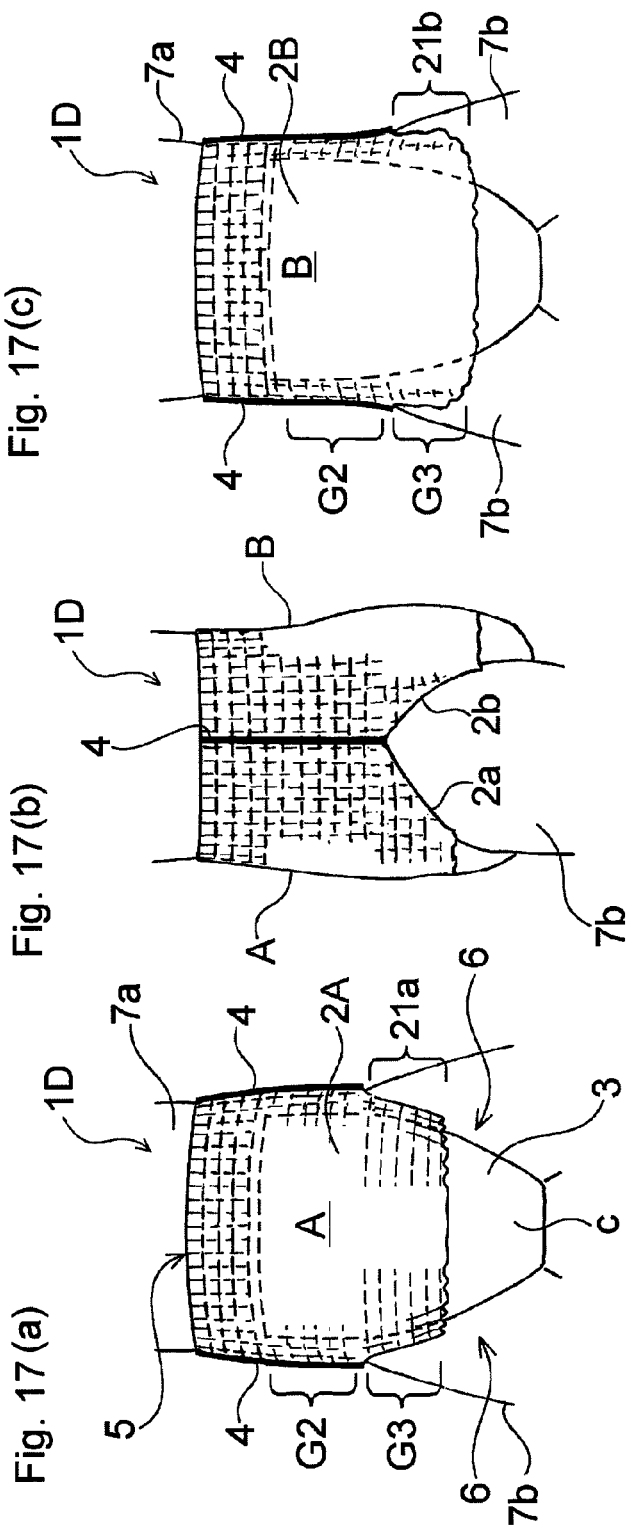

Thus, the rear extension portion 21b maintains sufficient coverage over the wearer's buttocks while being prevented from turning outward, and, on the other hand, the front extension portion 21a is made to contract somewhat largely in the diaper lateral direction (direction Y) to be deformed in conformity to the leg's circumference as depicted in FIG. 17. As a result, an improved fit is provided, and the feeling of insecurity about leakage is eliminated because the gap between the extension 21a and the wearer's body is thus reduced.

In the diaper 1D of the ninth embodiment, the length L2a is preferably 5% to 95%, more preferably 50% to 90%, of the length L1a. In the particular example shown in FIG. 19, the length L1a is substantially equal to the width of the absorbent assembly 3.

Since the diaper 1D has the front and the rear extension portion 21a and 21b in the front and the rear outer cover 2A and 2B and the second elasticized portion G30 in each of the front and the rear extension portion 21a and 21b, the side edge 2a of the extension portion 21a of the front outer cover 2A and the side edge 2b of the extension portion 21b of the rear outer cover 2B on each side of the diaper 1D separate from each other toward the front and the rear along the leg circumference as shown in FIG. 17(b) when the diaper 1D is put on a wearer. This will help to put on the diaper. Furthermore, there is formed a downward concave edge line along the circumference of the wearer's leg to provide a good appearance and a good fit.

The pull-on absorbent article of the invention includes an embodiment in which one or both of the front and the rear outer cover has no extension portion 21a or 21b and, instead, has a first and a second elasticized region G20 and G30 in the main portion 20a or 20b in the same manner as with the diaper 1D. In such an embodiment, the advantage obtained by making the length L2b greater than the length L1b in the rear outer cover 2B and making the length L2a smaller than the length L1a in the front outer cover 2A is, for example, that the front and/or the rear outer cover are capable of conforming to the wearer's body to provide a better fit and help to put on the diaper.

It is preferred that the length L2a be smaller than the length L2b in order for the absorbent assembly 3 to fit more snugly against the wearer's crotch to exhibit improved absorbency.

The absorbent assembly 3 of the diaper 1D is fixed on its one end portion (i.e., the portion overlapping the front outer cover 2A) to a lateral middle part of the front outer cover 2A with an adhesive and on its other end portion (i.e., the portion overlapping the rear outer cover 2B) to a lateral middle part of the rear outer cover 3B with an adhesive. More specifically, the adhesion between the absorbent assembly 3 and the first elasticized region G20 of the front outer cover 2A is achieved with an adhesive applied in a width substantially equal to the distance between the opposite first assembly-side fixing parts 28 and 28, and the adhesion between the absorbent assembly 3 and the second elasticized region G30 of the front outer cover 2A is achieved with an adhesive applied in a width substantially equal to the distance between the opposite second assembly-side fixing parts 229 and 229.

The same manner of adhesion applies to the rear outer cover 2B. That is, the adhesion between the absorbent assembly 3 and the first elasticized region G20 of the rear outer cover 2B is achieved with an adhesive applied in a width substantially equal to the distance between the opposite first assembly-side fixing parts 28 and 28, and the adhesion between the absorbent assembly 3 and the second elasticized region G30 of the rear outer cover 2B is achieved with an adhesive applied in a width substantially equal to the distance between the opposite second assembly-side fixing parts 229 and 229.

Accordingly, in the front outer cover 2A, the inequality relation between the lengths L1a and L2a of the non-elasticized subregions G121 and G131 of the first and the second elasticized region G20 and G30, respectively, agrees with the inequality relation between the length (in the diaper lateral direction, i.e., direction Y) of the bonded region of the absorbent assembly 3 to the first elasticized region G20 and the length of the bonded region of the absorbent assembly 3 to the second elasticized region G30.

In the rear outer cover 2B, too, the inequality relation between the lengths L1b and L2b of the non-elasticized subregions G121 and G131 of the first and the second elasticized region G20 and G30, respectively, agrees with the inequality relation between the length (in the diaper lateral direction, i.e., direction Y) of the bonded region of the absorbent assembly 3 to the first elasticized region G20 and the length of the bonded region of the absorbent assembly 3 to the second elasticized region G30.

As used herein, the expression "an inequality relation agrees with another inequality relation" means that, when the length L1a (or L1b) of the non-elasticized subregion G121 of the first elasticized region G20 is larger than the length L2a (or L2b) of the non-elasticized subregion G131 of the second elasticized region G30, the length (in the diaper lateral direction, i.e., direction Y) of the bonded region between the first elasticized region G20 and the absorbent assembly 3 is larger than the length (in the diaper lateral direction, i.e., direction Y) of the bonded region between the second elasticized region G30 and the absorbent assembly 3; and, when the length L1a (or L1b) of the non-elasticized subregion G121 of the first elasticized region G20 is smaller than the length L2a (or L2b) of the non-elasticized subregion G131 of the second elasticized region G30, the length (in the diaper lateral direction, i.e., direction Y) of the bonded region between the first elasticized region G20 and the absorbent assembly 3 is smaller than the length (in the diaper lateral direction, i.e., direction Y) of the bonded region between the second elasticized region G30 and the absorbent assembly 3.

Since the absorbent assembly 3 is fixed to the front and/or the rear outer cover 2A and 2B in such bonded region geometry, the extension and contraction of the first elasticized region G20 and/or the elasticized subregions G122 and G132 of the second elasticized region G30 are hardly interfered with even in the regions overlapping the absorbent assembly 3, and the above described various effects are further ensured. The bonded region geometry and its effects described also apply to 10th to 12th embodiments hereinafter described.

In the diaper 1D, the outer sheet 22 and the inner sheet 23 are folded along the waist opening edge, i.e., the diaper end edge 2d over the inner sheet 23 to form folded-over panels 22a and 23a, respectively. The folded-over panels 22a and 23a are bonded to the facing inner sheet 23 at the side seals 4 and to the topsheet side of the facing absorbent assembly 3 with an adhesive.

Figure 22:
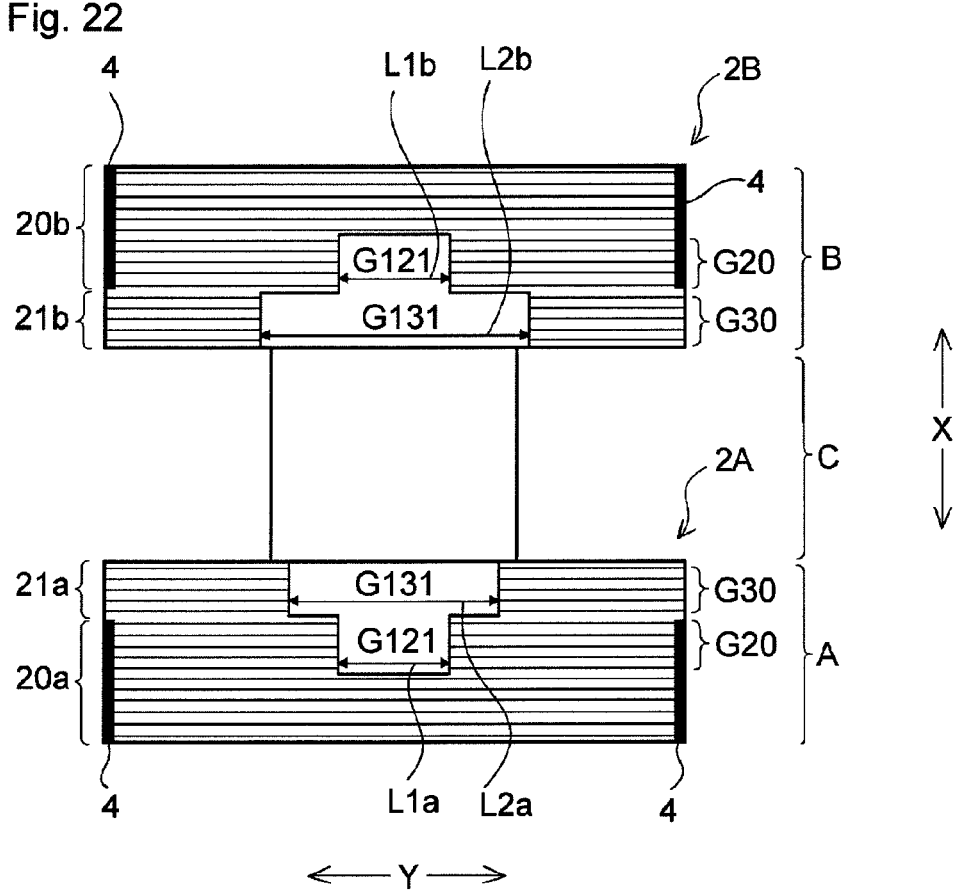
FIG. 22 is a schematic plan of a disposable pull-on diaper according to the 10th embodiment of the invention in its flat-out state.
Figure 23:
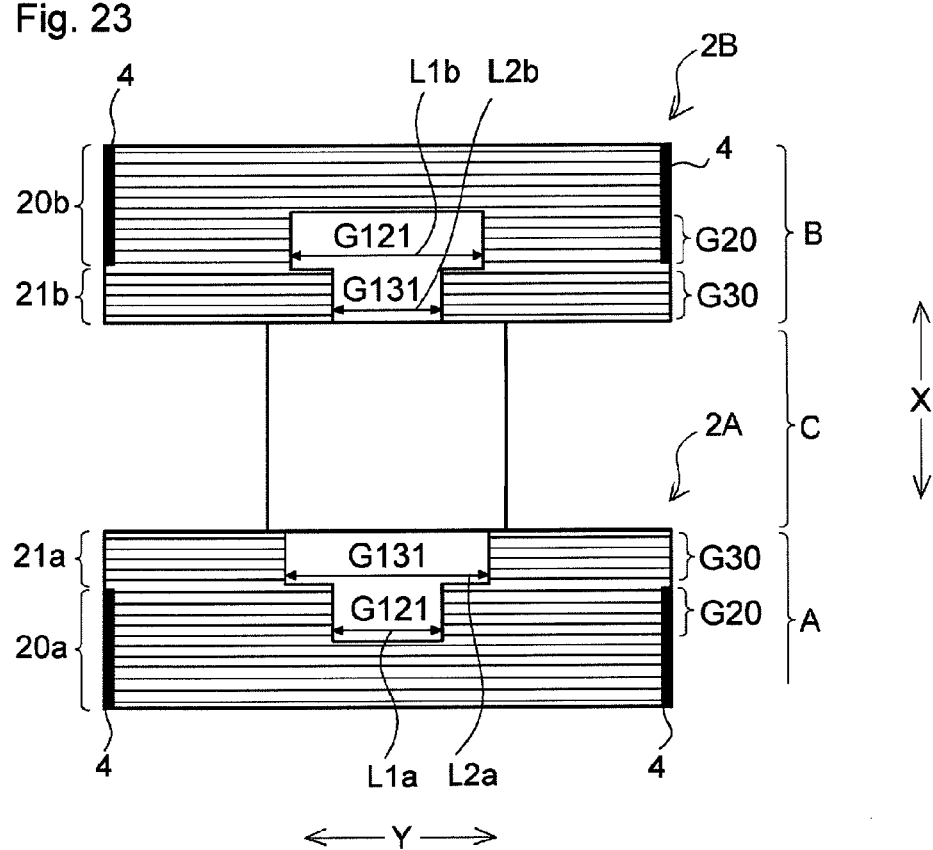
FIG. 23 is a schematic plan of a disposable pull-on diaper according to the 11th embodiment of the invention in its flat-out state.
Figure 24:
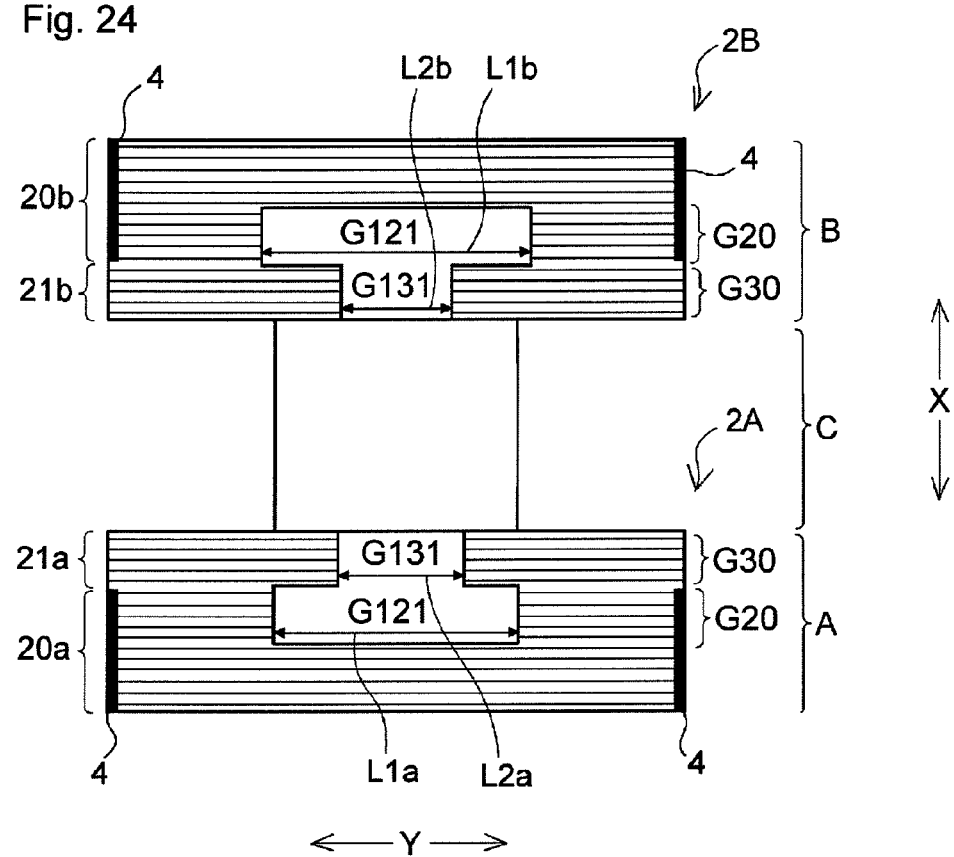
FIG. 24 is a schematic plan of a disposable pull-on diaper according to the 12th embodiment of the invention in its flat-out state.

FIGS. 22 through 24 schematically illustrate 10th to 12th embodiments of the invention (embodiments of the third aspect of the invention), respectively. Description of the disposable pull-on diapers of the 10th to 12th embodiments will generally be confined to the differences from the ninth embodiment, with the details in common omitted. The description of the ninth embodiment applies to the 10th to 12th embodiments with the exceptions noted hereunder. The elements or members shown in FIGS. 22 through 24 that are common to the ninth embodiment are identified with the same reference numerals as in the ninth embodiment.

In the 10th embodiment shown in FIG. 22, the length L2b (in the diaper lateral direction) of the non-elasticized subregion G131 of the second elasticized region G30 is larger than the length L1b (in the diaper lateral direction) of the non-elasticized subregion G121 of the first elasticized region G20 in the rear outer cover 2B similarly to the diaper 1D of the 9th embodiment. In the front outer cover 2A, the length L2a (in the diaper lateral direction) of the non-elasticized subregion G131 of the second elasticized region G30 is larger than the length L1a (in the diaper lateral direction) of the non-elasticized subregion G121 of the first elasticized region G20.

According to the 10th embodiment, the rear extension portion 21b is prevented from turning outward or reducing in buttock coverage, and the front extension portion 21a has a reduced contractive force in the diaper lateral direction (direction Y), which brings about prevention of skin troubles, such as red marks, and improvements on the diaper's fit, ease of putting on, and ease of moving around in. Furthermore, the diaper of the 10th embodiment is adaptable even to a relatively large wearer because the front extension portion is wide in the diaper lateral direction.

In the diaper of the 10th embodiment, the length L2b is preferably 105% to 200%, more preferably 110% to 150%, of the length L1b, and the length L2a is preferably 105% to 200%, more preferably 110% to 150%, of the length L1a.

The length L2a is preferably smaller than the length L2b in view of the fit of the absorbent assembly 3 against the wearer's crotch to have improved absorbency.

In the modification in which the absorbent article, such as a diaper, does not have a front and/or a rear extension portion 21a and/or 21b and instead has a first and a second elasticized region G2 G20 and G30 in the front and/or the rear main portion 20a and/or 20b, the advantage obtained by making the length L2b greater than the length L1b in the rear outer cover 2B and making the length L2a greater than the length L1a in the front outer cover 2A is, for example, that the front and/or the rear outer cover conform to the wearer's body to provide a better fit and ease of putting on the diaper.

In the 11th embodiment shown in FIG. 23, the length L2b (in the diaper lateral direction) of the non-elasticized subregion G131 of the second elasticized region G30 is smaller than the length L1b (in the diaper lateral direction) of the non-elasticized subregion G121 of the first elasticized region G20 in the rear outer cover 2B. In the front outer cover 2A, on the other hand, the length L2a (in the diaper lateral direction) of the non-elasticized subregion G131 of the second elasticized region G30 is larger than the length L1a (in the diaper lateral direction) of the non-elasticized subregion G121 of the first elasticized region G20.

The disposable pull-on diaper according to the 11th embodiment shows the following effect even when worn by a wearer with relatively slender buttocks and relatively thick thighs. The rear extension portion 21b is prevented from turning outward or reducing in coverage on the wearer's buttocks. The front extension portion 21a has a reduced contractive force in the diaper lateral direction (direction Y), which brings about prevention of skin troubles, such as red marks, and improvements on the diaper's fit and ease of putting on. Furthermore, the diaper is easy to move around in because the front extension portion is wide in the diaper lateral direction.

In the 11th embodiment, the length L2b is preferably 5% to 95%, more preferably 50% to 90%, of the length L1b, and the length L2a is preferably 105% to 200%, more preferably 110% to 150%, of the length L1a.

In the modification where the absorbent article, such as a diaper, does not have a front and/or a rear extension portion 21a and/or 21b and instead has a first and a second elasticized region G20 and G30 in the front and/or the rear main portion 20a and/or 20b, the advantage obtained by making the length L2b smaller than the length L1b in the rear outer cover 2B and making the length L2a greater than the length L1a in the front outer cover 2A is, for example, that the diaper conforms to the wearer's body to provide a better fit and ease of putting on.

In the 12th embodiment shown in FIG. 24, the length L2b (in the diaper lateral direction) of the non-elasticized subregion G131 of the second elasticized region G30 is smaller than the length L1b (in the diaper lateral direction) of the non-elasticized subregion G121 of the first elasticized region G20 in the rear outer cover 2B. In the front outer cover 2A, too, the length L2a (in the diaper lateral direction) of the non-elasticized subregion G131 of the second elasticized region G30 is smaller than the length L1a (in the diaper lateral direction) of the non-elasticized subregion G121 of the first elasticized region G20.

The disposable pull-on diaper according to the 12th embodiment shows the following effects even when worn by a relatively slender wearer. The rear extension portion 21b is prevented from turning outward or reducing in coverage on the wearer's buttocks. The front extension portion 21a is made to contract somewhat largely in the diaper lateral direction (direction Y) to be deformed in concert with the leg's circumference as depicted in FIG. 17, thereby to provide an improved fit and lessen the feeling of insecurity about leakage due to reduction in gap between the diaper and the wearer's body in the crotch.

In the 12th embodiment, the length L2b is preferably 5% to 95%, more preferably 50% to 90%, of the length L1b, and the length L2a is preferably 5% to 90%, more preferably 50% to 90%, of the length L1a.

In the modification where the absorbent article, such as a diaper, does not have a front and/or a rear extension portion 21a and/or 21b and instead has a first and a second elasticized region G2 and G3 in the front and/or the rear main portion 20a and/or 20b, the advantages obtained by making the length L2b smaller than the length L1b in the rear outer cover 2B and making the length L2a smaller than the length L1a in the front outer cover 2A include improvement in fit, prevention of diaper's sliding down, and adaptability to relatively slender bodies.

To further ensure one or more of the above described effects, it is preferred that the length L1' (see FIG. 19) of the first elasticized region G20 in the diaper longitudinal direction be 5% to 95% of the length La of the front outer cover 2A or the length Lb of the rear outer cover 2B in the diaper longitudinal direction (direction X) (see FIG. 18) and that the length L2' (see FIG. 19) of the second elasticized region G30 in the diaper longitudinal direction be 5% to 95% of the length La or Lb.

In the embodiments where the front outer cover 2A and/or the rear outer cover 2B has/have an extension portion 21a and/or 21b, the extension length L5 and L6 of the front and the rear extension portion 21a and 21b are each preferably 5% to 150%, more preferably 25% to 70%, of the length L4 of the side seals 4.

From the same standpoint, it is preferred that the extension length L5 of the front extension portion 21a be in the range of from 5% to 60%, more preferably 20% to 40%, of the length La of the front outer cover 2A and that the extension length L6 of the extension portion 21b in the rear outer cover 2B be in the range of from 5% to 60%, more preferably 20% to 40%, of the length Lb of the rear outer cover 2B.

Preferred ranges of the extension lengths L5 and L6 of the extension portions 21a and 21b, the reasons for the preference, the structure of the absorbent assembly, and the like are the same as in the first embodiment.

A preferred embodiment of a method for making the pull-on absorbent article according to the invention will be described by way of FIG. 25.

Figure 25:
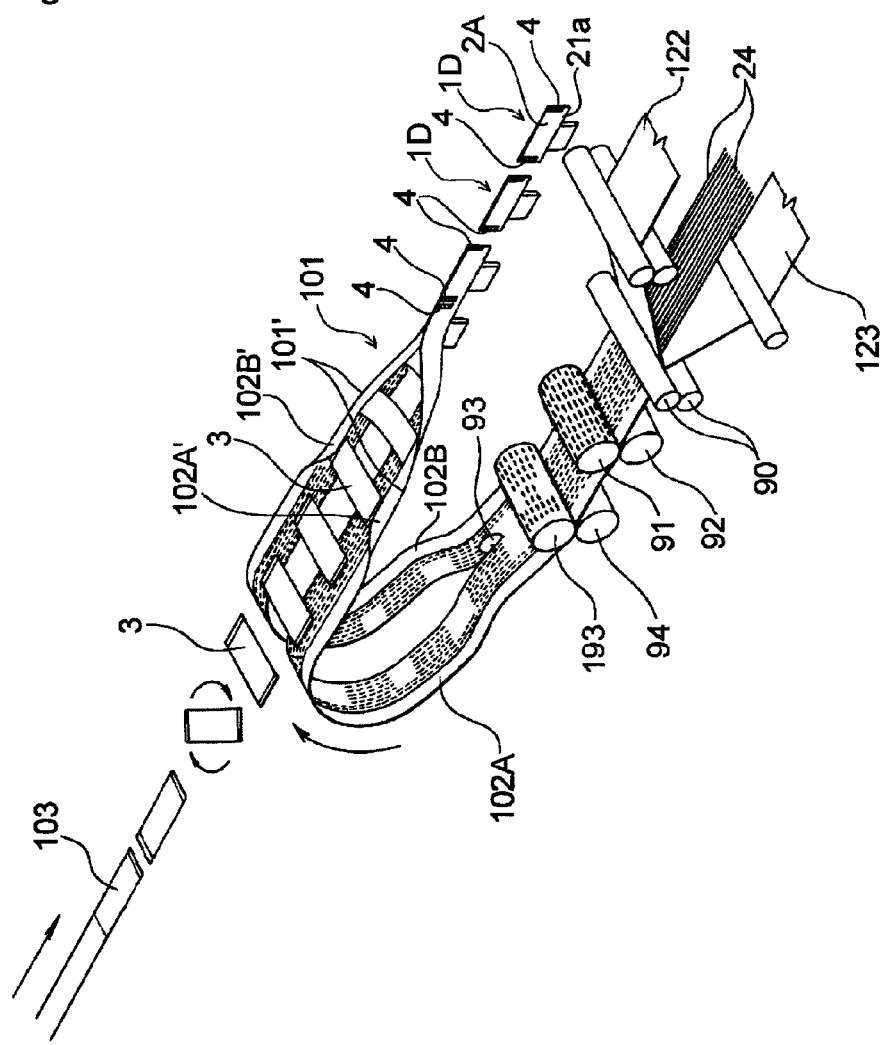
FIG. 25 illustrates an embodiment of a method for making a pull-on absorbent article according to the invention.

In the present embodiment of the method shown in FIG. 25, a wide continuous sheet 122 as an outer sheet precursor and a wide continuous sheet 123 as an inner sheet precursor are superposed on each other with elastic members 24 inserted therebetween in their stretched state. Before the continuous sheets 122 and 123 are joined, an adhesive for the formation of end fixing parts 27 and first and second assembly-side fixing parts 28 and 229 is applied intermittently to the continuous sheet 122 and/or the continuous sheet 123 by means of an unshown adhesive applicator. The two continuous sheets are pressed between a pair of nip rollers 90 to fix the elastic members 24 between the continuous sheets 122 and 123 at the fixing parts 27, 28, and 229.

The joined continuous sheets 122 and 123 are then introduced between a pressure roller 91 having, on its peripheral surface, projections for forming bonds 26 and a facing anvil roller 92 to be pressed in parts with heat thereby to form a large number of bonds 26. The laminate of the continuous sheets 122 and 123 with the elastic members 24 therebetween is then introduced between a roller 193 having, on its peripheral surface, projections for cutting the elastic members 24 and a facing anvil roller 94 to be pressed and/or heated thereby to cut the elastic members at positions within an area corresponding to the non-elasticized subregions G121 and G131 of the first and the second elasticized region G10 and G20, respectively, in each of the front and the rear outer cover 2A and 2B.

The distribution ranges of projections for cutting the elastic members 24 on the peripheral surface of the roller 193 used in the step of cutting the elastic members 24 have different circumferential lengths between the peripheral portion corresponding to the non-elasticized subregion G121 of the first elasticized region G20 and that corresponding to the non-elasticized subregion G131 of the second elasticized region G30 in the front outer cover 2A and also have different circumferential lengths between the peripheral portion corresponding to the non-elasticized subregion G121 of the first elasticized region G20 and that corresponding to the non-elasticized subregion G131 of the second elasticized region G30 in the rear outer cover 2B. The formation of the bonds 26 and the cutting of the elastic members 24 may be performed by using the same roller.

The laminate of the continuous sheets 122 and 123 with the elastic members 24 therebetween is then cut by a cutting unit 93 into two continuous sheets, 102A and 102B. The laminate is cut so that the continuous sheets 122 and 123 are divided along the border between the second elasticized region G30 of the front outer cover and that of the rear outer cover.

The two continuous sheets resulting from the cutting, i.e., 102A and 102B correspond to a continuous front outer cover 102A and a continuous rear outer cover 102B, respectively. The continuous front outer cover 102A has a structure generally corresponding to contiguously connected front outer covers 2A of a plurality of diapers 1D. The continuous rear outer cover 102B has a structure generally corresponding to contiguously connected rear outer covers 2B of a plurality of diapers 1D.

The line of cutting the continuous sheets 122 and 123 may be set not to pass through the bonds 26 or may be, and is preferably set to cut or divide bonds 26 arranged in a row along the machine direction (MD) of the sheets 122 and 123 in two (smaller bonds) in the direction perpendicular to the machine direction, i.e., the cross-machine direction (CD). In the latter case, because the crotch side edge 2c of each of the front and the rear outer cover 2A and 2B has an array of the smaller bonds resulting from dividing the row of bonds 26 in two, the vacant spaces 30 stably open along the edge 2c. As a result, the ventilation through the vacant spaces 30 or the valleys between the folds 29 is improved to provide effective prevention of skin overhydration and give better comfort to the wearer. The bond 26 may be cut into equal or unequal two smaller bonds. The resulting smaller bonds are preferably 0.5 mm or more, more preferably 2 mm or more, in the CD.

The cutting unit may be a known cutting device for continuously cutting a sheet material, for example, a cutter having a cutting blade on its upstream side, a cylindrical or disc-shaped cutter having an annular blade around its peripheral surface or edge, a laser cutter, or a water jet cutter. Cutting the sheet using a cutting unit is advantageous in that the axial length of the rollers, such as the pressure roller 91, is minimized since the step of separating the two continuous sheets apart from each other is preceded by the step of pressing.

While the continuous front outer cover 102A and the continuous rear outer cover 102B are advanced at a predetermined distance therebetween, an adsorbent assembly 3 is fixed to the continuous front outer cover 102A and the continuous rear outer cover 102B so as to bridge them. To achieve this, an adhesive is previously applied to the backsheet side of the adsorbent assembly 3 and/or the facing surface of the continuous outer covers 102A and 102B. In the present embodiment, side portions 102A' and 102B' along the moving edge of the continuous front and the outer cover 102A and 102B, respectively, are folded over and fixed to the respective end portions of the absorbent assembly 3.

The continuous-form diaper 101 thus obtained is then folded in two, followed by forming side seals 4 by heat sealing, ultrasonic sealing, high frequency sealing, adhesive application, or a combination of such means. The side seals 4 are preferably formed using an unshown sealing unit having a pair of sealing rollers. The continuous-form diaper 101 is folded in two with edges (i.e., the folded edges 101' resulting from folding over the side portions 102A' and 102B' of the continuous front and the rear outer cover 102A and 102B, respectively) even.

After the formation of the side seals 4 and 4, the continuous-form diaper 101 is cut to size using a known cutting means (not shown) to obtain individual disposable pull-on diapers 1D having the aforementioned structure. The side seals 4 and 4 are formed not to extend over the whole width of the continuous front outer cover 102A and the continuous rear outer cover 102B so that the diaper 1D may have the above-described front and rear extension portions 21a and 21b in the front and the rear outer cover 2A and 2B thereof.

In carrying out the method of the present embodiment, the undescribed details are the same as those in conventional production of disposable pull-on diapers in what we call a lateral feed system. For instance, the absorbent assembly 3 that is to be disposed on the continuous front outer cover 102A and the continuous rear outer cover 102B is obtained by making a continuous-form absorbent assembly 103 having absorbent assemblies contiguously connected end-to-end in a known manner and cutting the continuous form to provide an absorbent assembly for each diaper. The resulting individual absorbent assemblies 3 may be turned 90° and spacedly disposed on the continuous front outer cover 102A and the continuous rear outer cover 102B.

Thus, the method of the present embodiment achieves easy and efficient production of diapers having different lengths between the non-elasticized subregion G121 of the first elasticized region G20 and the non-elasticized subregion G131 of the second elasticized region G30 in the front and/or the rear outer cover 2A and 2B. Furthermore, the method completes without involving the step of trimming the outer cover-forming continuous sheets 122 and 123 to form the leg openings. Therefore, the steps associated with removal and recycling of trimmings are unnecessary, making the method efficient and economical. To produce no trimmings is environmentally friendly.

The pull-on absorbent article according to the third aspect of the invention may dispense with either one of the front and the rear extension portion or both the front and the rear extension portion.

Either one of the front outer cover 2A and the rear outer cover 2B may have the first elasticized region G20 and the second elasticized region 030 having the non-elasticized subregion G121 and G131, respectively, which are different in length, whereas the other may have an elasticized region having no such non-elasticized subregions. Either one of the front outer cover 2A and the rear outer cover 2B may have the first and the second elasticized region G20 and G30 having the non-elasticized subregion G121 and G131, respectively, which are different in length, whereas the other may have an elasticized region having a non-elasticized subregion having a uniform length in the diaper lateral direction and a width (in the diaper longitudinal direction) spanning from the end of the absorbent assembly 3 to the crotch side edge of the other outer cover.

Figure 21A:
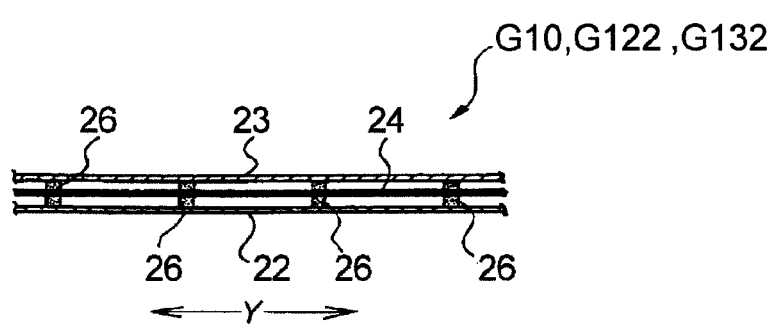
Figure 21B:
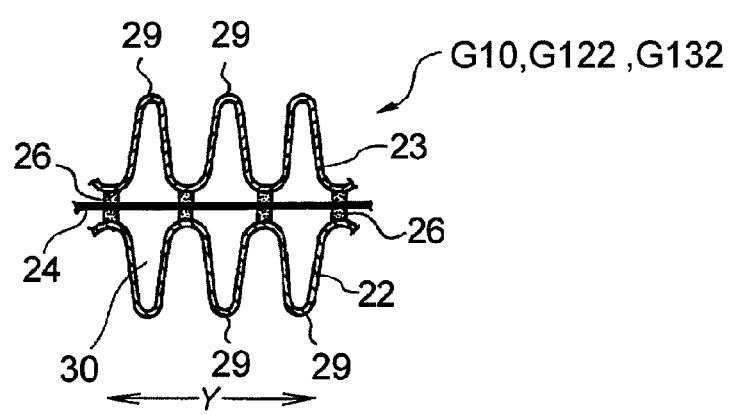

The elasticized waist region G10, the elasticized subregions G122 and G122 of the first elasticized region G20, and the elasticized subregions G132 and G132 of the second elasticized region G30, and the like may be formed of a laminate in which the outer sheet 22 and the inner sheet 23 are bonded together all over with the elastic members 24 fixed therebetween instead of being bonded discretely at bonds 26 as depicted in FIG. 21. When the outer sheet 22 and the inner sheet 23 are bonded at bonds 26 as in the case of the diaper 1D, the bonds 26 may be arranged in a staggered or other pattern in a plan view.

Figure 26:
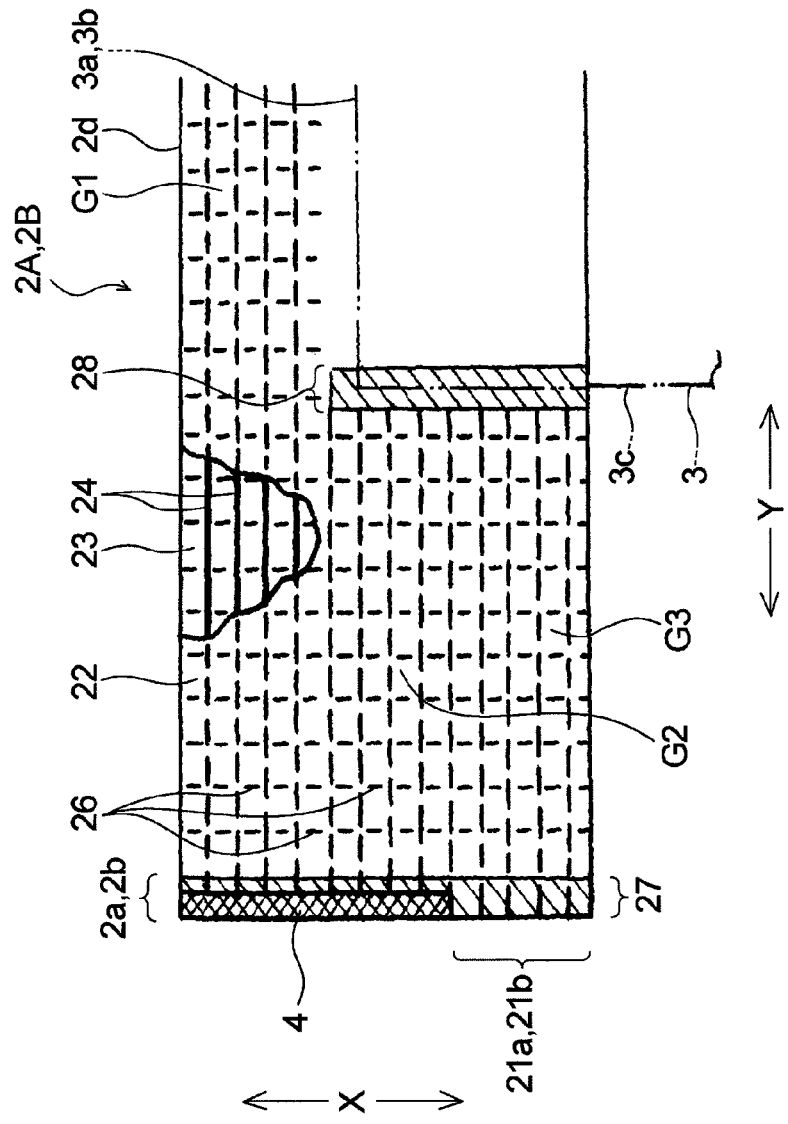
FIG. 26 is a fragmentary enlarged view of the front or the rear outer cover of a disposable pull-on diaper produced by an embodiment of the method for making a pull-on absorbent article according to the invention.

A more preferred embodiment of the method for producing the pull-on absorbent article of the invention will be described. This embodiment is one embodiment of the fourth aspect of the invention. The method according to the preset embodiment is a method for continuously producing the diaper 1 of the first embodiment of the invention, provided that the diaper 1 produced by the present embodiment slightly differs in the structure of the lower edge of the front outer cover 2A and/or the rear outer cover 2B as can be seen by comparing FIGS. 3 and 26.

The diaper 1 produced by the present embodiment has the bonds 26 discretely arranged in lines extending in the diaper longitudinal direction (direction X), which are longitudinally spaced and transversely disposed so that the positions in direction X of the bonds of a line coincide with those of the bonds of adjacent lines.

Figure 27:
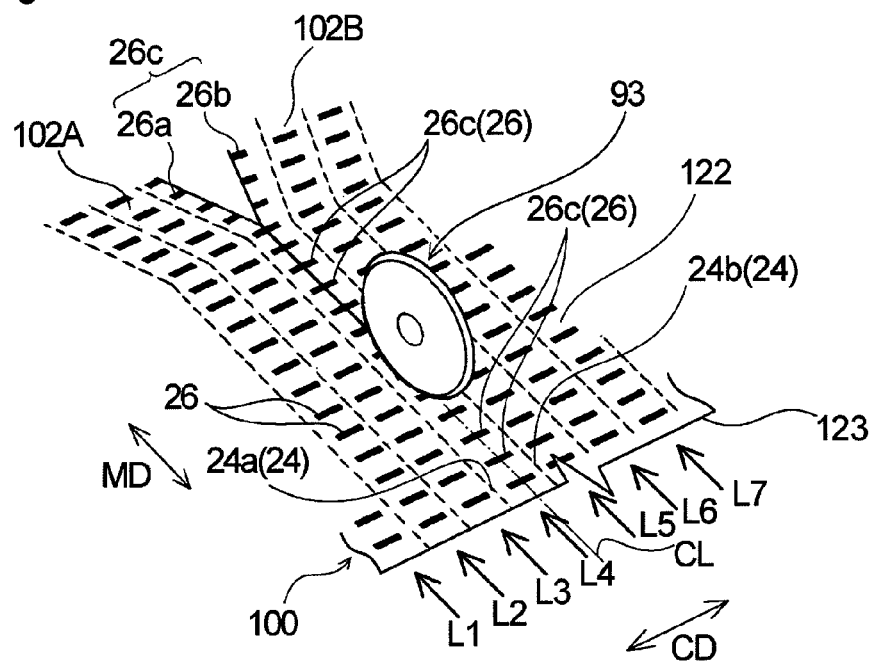
FIG. 27 is a perspective illustrating the detail of the step of cutting in an embodiment of the method for making a pull-on absorbent article according to the invention.

The method of the present embodiment includes the steps of superposing two continuous sheets 122 and 123 with a plurality of elastic members disposed therebetween as shown in FIG. 5 (superposing step), bonding the continuous sheets 122 and 123 to each other in parts to make a composite sheet 100 by forming bonds 26 such that the bonds 26 are discretely arranged in the MD to make, as shown in FIG. 27, at least three rows of bonds (L1 to L7) and that every elastic member 24 is sandwiched between adjacent two of the rows of bonds (bonding step), cutting the composite sheet 100 in half to obtain two narrower continuous sheets 102A and 102B in a way that every bond 26c making up one row of the bonds, L4, is cut in two in the CD as shown in FIG. 27 (cutting step), fixing an adsorbent assembly 3 to the continuous sheet 102A and the continuous sheet 102B so as to bridge them while advancing the two continuous sheets 102A and 102B at a predetermined distance from each other to make a continuous-form absorbent article 101 as shown in FIG. 5 (absorbent assembly fixing step), folding the continuous-form absorbent article 101 in two (folding step), and forming side seals 4 and 4 and cutting the continuous-form absorbent article 101 to obtain individual disposable pull-on diapers 1.

The method according to the present embodiment will further be illustrated with reference to FIGS. 5 and 27.

The method of the present embodiment includes the step of superposing in which, as shown in FIG. 5, a wide continuous sheet 122 as an outer sheet precursor and a wide continuous sheet 123 as an inner sheet precursor are superposed on each other with a plurality of elastic members 24 disposed therebetween in their stretched state. Before the continuous sheets 122 and 123 are superposed, an adhesive for the formation of end fixing parts 27 and absorbent assembly-side fixing parts 28 is applied intermittently to the continuous sheet 122 and/or the continuous sheet 123 by means of an unshown adhesive applicator. The two continuous sheets are pressed between a pair of nip rollers 90 to fix the elastic members 24 between the continuous sheets 122 and 123 at the fixing parts 27 and 28.

The joined continuous sheets 122 and 123 are then introduced between a pressure roller 91 having on its peripheral surface projections for forming bonds 26 and projections for cutting the elastic members 24 and a facing anvil roller 92 to be pressed in parts with heat. As a result, a large number of bonds 26 are formed, and the elastic members 24 are cut in regions where an absorbent assembly 3 is to be disposed.

By the formation of the bonds 26, the continuous sheets 122 and 123 are bonded together in parts (bonding step). As shown in FIG. 27, the bonds 26 are discretely arranged in a way to form at least three rows in the MD. In FIG. 27, only seven rows L1 to L7 are shown, which are formed on and around the cutting line CL along which the composite sheet 100 is to be cut. The bonds 26 are also arranged in a way that every elastic member 24 is sandwiched between adjacent two rows of bonds as shown in FIG. 27. In the particular example shown in FIG. 27, rows of bonds L3 and L4 are positioned on either side of an elastic member 24a, and rows of bonds L4 and L5 are positioned on either side of an elastic member 24b.

The continuous sheets 122 and 123 bonded together at the bonds 26 with the elastic members 24 therebetween (i.e., the composite sheet 100) are then cut by a cutting unit 93 into two narrower continuous sheets 102A and 102B (cutting step). The cutting step is effected in a way that, as shown in FIG. 27, every bond 26c making up one row of bonds, L4, is cut in two in the CD. Smaller bonds 26a and 26b shown in FIG. 27 are the results of cutting one bond 26c in two. The bond 26c may be cut into equal halves to create two smaller bonds 26a and 26b equal in length in the CD, or may be cut into unequal halves. It is preferred for each of the resulting smaller bonds 26a and 26b resulting from the cutting to have a length of 0.5 mm or more, more preferably 2 mm or more, in the CD. It is also preferred for each of the smaller bonds 26a and 26b resulting from the cutting to have a length of 10% to 90% of the length of the bond 26c (before being cut), more preferably 1 to 30 mm or more. The term "narrower" as used herein with respect to "continuous sheets" means to be narrower than the composite sheet 100 before being cut in two.

The bonds 26c to be cut in two may be equal to or smaller than the other bonds that are not cut in length in the CD, but are preferably larger than the other bonds in length in the CD. For example, the length of the bonds 26c is preferably about 1.5 to 10 times, more preferably about 2 to 5 times, the length of the other bonds not to be cut.

The two narrower continuous sheets 102A and 102B correspond to a continuous front outer cover 102A and a continuous rear outer cover 102B, respectively. The continuous front outer cover 102A has a structure generally corresponding to contiguously connected front outer covers 2A of a plurality of diapers 1. The continuous rear outer cover 102B has a structure generally corresponding to contiguously connected rear outer covers 2B of a plurality of diapers 1.

The cutting unit 93 may be any of known cutting devices for continuously cutting a sheet material, for example, a cutter having a cutting blade on its upstream side, a cylindrical or disc-shaped cutter having an annular blade around its peripheral surface or edge, a laser cutter, or a water jet cutter.

The cutting unit 93 shown in FIG. 27 is a disc cutter having a sharp blade around its peripheral edge, of which the axis of rotation is parallel to the MD. A counter support roller having a smooth surface is placed on the opposite side of the composite sheet 100 to the disc cutter. The disc cutter and the support roller may be positively driven by a motor, etc. at a predetermined rotational speed or may rotate by the action of the moving composite sheet 100.

While the continuous front outer cover (narrower continuous sheet) 102A and the continuous rear outer cover (narrower continuous sheet) 102B are advanced at a predetermined distance from each other, an adsorbent assembly 3 is fixed to the continuous front and outer covers 102A and 102B so as to bridge them (absorbent assembly fixing step).

The absorbent assembly fixing step and the subsequent steps are carried out in the same manner as in the above described method for producing the diaper 1. The continuous-form diaper 101 may be cut to size simultaneously with the formation of side seals 4 and 4.

Figure 28:
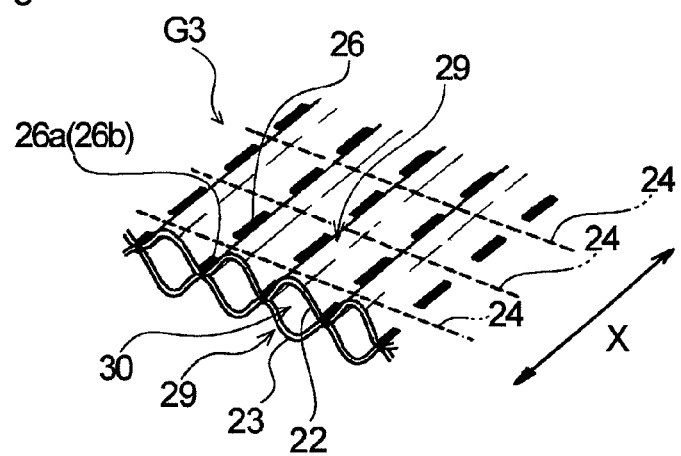
FIG. 28 is a perspective illustrating the lower edge of the front or the rear outer cove of a pull-on absorbent article obtained by an embodiment of the method for making a pull-on absorbent article according to the invention.

According to the method of the present embodiment, since the laminate of the continuous sheets 122 and 123 is cut to provide two narrower continuous sheets 102A and 102B, from which the front and rear outer covers 2A and 2B are obtained. Therefore, the lower edge (closer edge to the crotch portion) of the outer sheet 22 and that of the inner sheet 23 are even in both the front and the rear outer cover 2A and 2B, and, as shown in FIG. 28, vacant spaces 30 defined by the folds 29 of the outer sheet 22 and the folds 29 of the inner sheet open along the lower edge of the front and the rear outer cover 2A and 2B. As a result, a good appearance is provided. Because the vacant spaces 30 maintain the open state relatively stably so that the ventilation through the vacant spaces 30 or the valleys between the folds 29 is improved to provide effective prevention of skin overhydration and better wearer comfort. The skin overhydration preventive effect is further ensured when both the inner and the outer sheet 23 and 22 are breathable sheets.

The method of the present embodiment enables production of disposable pull-on diapers without trimming the outer cover-forming continuous sheets 122 and 123 to form leg openings. Therefore, the steps associated with removal and recycling of trimmings are unnecessary, and disposable pull-on diapers can be produced efficiently and economically. To produce no trimmings is environmentally friendly.

While the fourth aspect of the invention has been described with reference to its preferred embodiment, the method of making pull-on absorbent articles according to the fourth aspect of the invention is not construed as being limited thereto.

For example, in the above described embodiment, the side seals 4 and 4 are formed not to extend the whole width of the continuous front outer cover 102A and the continuous rear outer cover 102B to make the disposable pull-on diaper 1 of which the front and the rear outer cover 2A and 2B have the extension portions 21a and 21b, respectively, extending downward from the side seals. Instead of this, the side seals 4 and 4 may be formed to extend the whole width of the continuous front and rear outer covers 102A and 102B to make a disposable pull-on diaper of which the front and the rear outer cover 2A and 2B do not have such extension portions 21a and 21b.

While in the above embodiment the rows of bonds L1 to L7 are formed in the continuous sheets 122 and 123 in a pattern in which the positions in the MD of the individual bonds of a row coincide with those of the bonds of adjacent rows as shown in FIG. 27, the bonds 26 may be arranged in a staggered pattern in which the bonds 26 of adjacent rows may be offset by half a pitch. The individual bonds 26 may have any shape, such as an elongated circle, ellipse, circle, or rhombus, as well as a rectangle.

The side portions 102A' and/or 102B' extending in the MD along one edge of the continuous front outer cover 102A and/or the continuous rear outer cover 102B may (as shown in FIG. 5) or may not be folded over before being cut into the front and the rear outer cover 2A and 2B.

The pull-on absorbent articles of the invention and the methods of making them have been described with reference to their preferred embodiments, but the invention is not deemed to be limited to the embodiments described.

For example, while the side seal 4 is formed along the side edges 2a and 2b of the outer covers, there may be a non-bonded region outboard of the side seal 4. That is, there may be a non-bonded region in which the front outer cover 2A and/or the rear outer cover 2B are not bonded together outside each side seal 4 that is formed by bonding the front and the outer cover 2A and 2B near the side edges 2a and 2b.

The end fixing parts 27 in the diapers 1, 1A, 1B, 1D, and so on may be formed at a certain distance, e.g., of up to 20 mm from the lateral side edges of the front and the rear outer cover 2A and 2B.

The pull-on absorbent article may be a pull-on sanitary napkin and the like as well as a disposable pull-on diaper for children or adults.

In the description given above, particulars of a certain embodiment that have been omitted to avoid redundancy can appropriately be complemented by the corresponding description of other embodiments. Particulars described as being characteristic of a certain embodiment can apply to other embodiments appropriately.

Particulars of every embodiment are appropriately interchangeable between embodiments.

For instance, the absorbent assembly shown in FIGS. 7 and 8 used in the fifth embodiment may be used in other embodiments. The method for producing a pull-on absorbent article according to the fourth aspect of the invention may be used to make disposable pull-on diapers of other than the first embodiment.

INDUSTRIAL APPLICABILITY

The pull-on absorbent article of the invention (first aspect) is of the type wherein the outer cover is separated into a front outer cover to be worn around the front of a wearer and a rear outer cover to be worn around the rear of the wearer and yet has a good appearance, is successfully prevented from sliding down, and provides excellent wearer comfort.

The pull-on absorbent article of the invention (second aspect) is of the type wherein the outer cover is separated into a front outer cover to be worn around the front of a wearer and a rear outer cover to be worn around the rear of the wearer and yet has a good appearance.

The pull-on absorbent article of the invention (third aspect) is of the type wherein the outer cover is separated into a front outer cover to be worn around the front of a wearer and a rear outer cover to be worn around the rear of the wearer and yet provides an improved appearance and/or fit around the crotch portion.

The method of producing a pull-on absorbent article according to the invention (fourth aspect) enables efficient production of pull-on absorbent articles providing a good appearance, good protection against skin overhydration, and a good fit.

The invention claimed is:

1. A pull-on absorbent article comprising a front outer cover adapted to be worn around a wearer's front side, a rear outer cover adapted to be worn around the wearer's rear side, and an absorbent assembly fixed to the front and the outer cover so as to bridge them, the article having a longitudinal direction and a lateral direction, and the article having a pair of side seals formed by joining the front outer cover and the rear outer cover along their lateral side edges,
   each of the front and the outer cover having a laterally uniform length in the longitudinal direction, being longer than the side seals in the longitudinal direction, and having an extension portion extending downward from the side seals, and
   the extension portion of the front outer cover and/or the extension portion of the rear outer cover having an elasticized region exhibiting extensibility and contractibility in the lateral direction in a region located laterally outward of each side edge of the absorbent assembly,
   wherein the absorbent assembly has opposite side edge portions along the lateral side edges thereof and an elastic member disposed in each side edge portion, and each of the side edge portions where the elastic member is provided is not bonded to the extension portion of the front outer cover and/or the rear outer cover.

2. The pull-on absorbent article according to claim 1, wherein the extension portion of the front outer cover and the extension portion of the rear outer cover have substantially the same extension length.

3. The pull-on absorbent article according to claim 1, wherein the front and the rear outer cover each comprise an outer sheet, an inner sheet laid on an inner side of the outer sheet, and a plurality of elastic members therebetween,
   the elasticized region having the outer sheet and the inner sheet bonded to each other at a large number of bonds, the bonds being discretely arranged in the longitudinal direction to form a plurality of lines of bonds, and each of the elastic members in the elasticized region being arranged to pass between the bonds adjacent in the longitudinal direction.

4. The pull-on absorbent article according to claim 1, the absorbent assembly is bonded to the front and the rear outer cover in respective bonded regions, the bonded region of the front outer cover being smaller than that of the rear outer cover in width.

5. The pull-on absorbent article according claim 1, wherein each of the extension portions of the front and the rear outer cover has an extension length of 5% to 150% of the length of the side seals.

6. The method for producing the pull-on absorbent article according to claim 1, comprising the steps of fixing an adsorbent assembly to a continuous front outer cover and a continuous rear outer cover so as to bridge them while advancing the continuous front outer cover and the continuous rear outer cover at a predetermined distance from each other to make a continuous-form diaper, folding the continuous-form diaper in two, forming side seals extending short of the whole width of the continuous front outer cover and the continuous rear outer cover in the folded continuous-form diaper, and cutting the continuous-form diaper having the side seals into individual diapers.

7. A pull-on absorbent article comprising a front outer cover adapted to be worn around a wearer's front side, a rear outer cover adapted to be worn around the wearer's rear side, and an absorbent assembly fixed to the front outer cover and the rear outer cover so as to bridge them, the article having a longitudinal direction and a lateral direction, and the article having a pair of side seals formed by joining the front outer cover and the rear outer cover along their lateral side edges,
   each of the front and the outer cover being longer than the side seals in the longitudinal direction and having an extension portion extending downward from the side seals, and
   the extension portion of the front outer cover comprising two sheets and at least one elastic member therebetween,
   the front outer cover having opposite fixing parts each at or near the respective lateral side edges thereof, and the at least one elastic member being fixed to the two sheets at the opposite fixing parts and not being fixed to either of the two sheets between the opposite fixing parts, and
   the two sheets of the extension portion of the front outer cover being bonded to each other in a region that overlaps the absorbent assembly at a linear bond extending in the lateral direction.

8. The pull-on absorbent article according to claim 7, wherein the linear bond comprises a plurality of linear bonds spaced in the longitudinal direction.

9. The pull-on absorbent article according to claim 8, wherein the length of the linear bonds in the lateral direction decreases downward.

10. A pull-on absorbent article comprising a front outer cover adapted to be worn around the wearer's front, a rear outer cover adapted to be worn around the wearer's rear, and an absorbent assembly fixed to the front outer cover and the rear outer cover so as to bridge them, the front outer cover and the rear outer cover being connected to each other to make a loop, the article having a longitudinal direction and a lateral direction,
   at least one of the front and the rear outer cover having a first elasticized region extensible in the lateral direction and located closer to the crotch portion of the absorbent article than the respective longitudinal end of the absorbent assembly and a second elasticized region extensible in the lateral direction and located closer to the crotch portion than the first elasticized region,
   each of the first and the second elasticized region comprising two sheets and an elastic member disposed between the two sheets in its stretched state and having a non-elasticized subregion formed by cutting the elastic member in an area overlapping the absorbent assembly and a pair of elasticized subregions located one on each side of the non-elasticized subregion, and
   the non-elasticized subregion of the first elasticized region and the non-elasticized subregion of the second elasticized region being different in length in the lateral direction.

11. The pull-on absorbent article according to claim 10, wherein the absorbent article has a pair of side seals formed by joining the front outer cover and the rear outer cover along their lateral side edges, each of the front and the outer cover is longer than the side seals in the longitudinal direction and has an extension portion extending downward from the side seals, and the second elasticized region is in the extension portion.

12. The pull-on absorbent article according to claim 10, wherein the rear outer cover has the first and the second elasticized region, and, in the rear outer cover, the non-elasticized subregion of the second elasticized region is longer in the lateral direction than the non-elasticized subregion of the first elasticized region.

13. The pull-on absorbent article according to claim 12, wherein the front outer cover has the first and the second elasticized region, and, in the front outer cover, the non-elasticized subregion of the second elasticized region is shorter in the lateral direction than the non-elasticized subregion of the first elasticized region.

14. The pull-on absorbent article according to claim 12, wherein the front outer cover has the first and the second elasticized region, and, in the front outer cover, the non-elasticized subregion of the second elasticized region is longer in the lateral direction than the non-elasticized subregion of the first elasticized region.

15. The pull-on absorbent article according to claim 10, wherein both the front and the rear outer cover have the first and the second elasticized region, the non-elasticized subregion of the second elasticized region is shorter in the lateral direction than the non-elasticized subregion of the first elasticized region in the rear outer cover, and the non-elasticized subregion of the second elasticized region is longer in the lateral direction than the non-elasticized subregion of the first elasticized region in the front outer cover.

16. The pull-on absorbent article according to claim 10, wherein both the front and the rear outer cover have the first and the second elasticized region, and the non-elasticized subregion of the second elasticized region is shorter in the lateral direction than the non-elasticized subregion of the first elasticized region in each of the front and the rear outer cover.

17. The pull-on absorbent article according to claim 10, wherein, in the front and/or the rear outer cover, the inequality relation between the lengths of the non-elasticized subregions of the first and the second elasticized region in the lateral direction agrees with the inequality relation between the lengths of the bonded regions between the absorbent assembly and the first and the second elasticized region.

18. A method for producing the pull-on absorbent article according to claim 10, comprising the steps of superposing two continuous sheets, one as a precursor of the front outer cover and the other as a precursor of the rear outer cover, with elastic members disposed therebetween, introducing the superposed continuous sheets between a roller having, on its peripheral surface, projections for cutting elastic members and a facing roller to cut the elastic members at positions within an area corresponding to the non-elasticized subregions of the first and the second elasticized region in each of the front and the rear outer cover, and, after the step of cutting the elastic members, cutting the two continuous sheets into the front outer cover and the rear outer cover.

19. A method for producing a pull-on absorbent article comprising a front outer cover adapted to be worn around a wearer's front side, a rear outer cover adapted to be worn around the wearer's rear side, and an absorbent assembly fixed to the front outer cover and the rear outer cover so as to bridge them, the article having a pair of side seals formed by joining the front outer cover and the rear outer cover along their lateral side edges, the method comprising the steps of:

superposing two continuous sheets with a plurality of elastic members disposed therebetween, bonding the continuous sheets to each other in parts to make a composite sheet by forming bonds such that the bonds are discretely arranged in the machine direction to make at least three rows of bonds and that every elastic member is sandwiched between adjacent two of the rows of bonds, cutting the composite sheet in half to obtain two narrower continuous sheets in a way that every bond making up one of the rows of bonds is cut in two in the cross-machine direction, fixing an adsorbent assembly to the narrower continuous sheets so as to bridge them while advancing the narrower continuous sheets at a predetermined distance from each other to make a continuous-form absorbent article, folding the continuous-form absorbent article in two, and forming side seals in the continuous-form absorbent article and cutting the continuous-form absorbent article to obtain individual pull-on absorbent articles.

20. The method for producing a pull-on disposable diaper according to claim 19, further comprising the step of pressing the superposed two continuous sheets to cut the elastic members at positions within a region where the absorbent assembly is to be disposed.

* * * * *